US012414559B2

(12) United States Patent
Shabtai et al.

(10) Patent No.: US 12,414,559 B2
(45) Date of Patent: Sep. 16, 2025

(54) MIXTURES AND COMPOSITIONS COMPRISING 5-FLUORO-4-IMINO-3-METHYL-1-TOSYL-3,4-DIHYDROPYRIMIDIN-2-ONE, AND METHODS OF USE THEREOF

(71) Applicant: Adama Makhteshim Ltd., Beer Sheva (IL)

(72) Inventors: Sami Shabtai, Omer (IL); Noam Sheffer, Herzliya (IL); Jenny Lerner Yardeni, Mishmar Hanegev (IL); James Sloan, Southsea (GB)

(73) Assignee: ADAMA MAKHTESHIM LTD., Beer Sheva (IL)

( * ) Notice: Subject to any disclaimer, the term of this patent is extended or adjusted under 35 U.S.C. 154(b) by 1004 days.

(21) Appl. No.: 17/291,042

(22) PCT Filed: Nov. 4, 2019

(86) PCT No.: PCT/IB2019/059456
§ 371 (c)(1),
(2) Date: May 4, 2021

(87) PCT Pub. No.: WO2020/095181
PCT Pub. Date: May 14, 2020

(65) Prior Publication Data
US 2021/0378235 A1 Dec. 9, 2021

Related U.S. Application Data

(60) Provisional application No. 62/755,866, filed on Nov. 5, 2018.

(51) Int. Cl.
| | |
|---|---|
| *C07D 239/47* | (2006.01) |
| *A01N 25/02* | (2006.01) |
| *A01N 25/04* | (2006.01) |
| *A01N 25/12* | (2006.01) |
| *A01N 25/30* | (2006.01) |
| *A01N 43/54* | (2006.01) |
| *A01P 3/00* | (2006.01) |

(52) U.S. Cl.
CPC ............ *A01N 25/02* (2013.01); *A01N 25/04* (2013.01); *A01N 25/30* (2013.01); *A01N 43/54* (2013.01); *A01P 3/00* (2021.08); *C07D 239/47* (2013.01)

(58) Field of Classification Search
CPC ...... C07D 239/47; A01N 43/54; A01N 25/02; A01N 25/04; A01N 25/12; A01N 25/30; A01P 3/00
See application file for complete search history.

(56) References Cited

U.S. PATENT DOCUMENTS

| | | |
|---|---|---|
| 8,263,603 B2 | 9/2012 | Boebel |
| 8,318,758 B2 | 11/2012 | Boebel |
| 8,470,839 B2 | 6/2013 | Boebel |
| 8,552,020 B2 | 10/2013 | Boebel |
| 8,658,660 B2 | 2/2014 | Boebel |
| 8,916,579 B2 | 12/2014 | Boebel |
| 9,000,002 B2 | 4/2015 | Boebel |
| 9,006,259 B2 | 4/2015 | Boebel |
| 9,271,497 B2 | 3/2016 | Lorsbach |
| 9,321,734 B2 | 4/2016 | Lorsbach |
| 9,526,245 B2 | 12/2016 | Owen |
| 9,532,570 B2 | 1/2017 | Owen |
| 9,538,753 B2 | 1/2017 | Owen |
| 9,622,474 B2 | 4/2017 | Lorsbach |
| 9,642,368 B2 | 5/2017 | Lorsbach |
| 9,840,475 B2 | 12/2017 | Lorsbach |
| 9,850,215 B2 | 12/2017 | Choy et al. |
| 9,862,686 B2 | 1/2018 | Boebel |
| 9,908,855 B2 | 3/2018 | Lorsbach |
| 10,045,533 B2 | 8/2018 | Owen |
| 10,045,534 B2 | 8/2018 | Owen |
| 10,051,862 B2 | 8/2018 | Owen |
| 10,059,703 B2 | 8/2018 | Lorsbach |
| 10,426,165 B2 | 10/2019 | Owen |
| 10,426,166 B2 | 10/2019 | Owen |
| 10,426,167 B2 | 10/2019 | Owen |

(Continued)

FOREIGN PATENT DOCUMENTS

| | | |
|---|---|---|
| WO | WO 2015/103261 A1 | 7/2015 |
| WO | WO 2017/017055 A1 | 2/2017 |

(Continued)

OTHER PUBLICATIONS

Jan. 11, 2022 First Office Action issued by the China National Intellectual Property Administration in connection with Chinese Application No. 201980087412.4 (including English translation).

(Continued)

*Primary Examiner* — Joseph K McKane
*Assistant Examiner* — Sagar Patel
(74) *Attorney, Agent, or Firm* — Gary J. Gershik

(57) ABSTRACT

The present invention provides stable, liquid compositions comprising (a) a fungicidally effective amount of a compound of Formula I and (b) a liquid carrier. The present invention also provides mixtures and compositions comprising (a) a fungicidally effective amount of a compound of Formula I and (b) at least one adjuvant selected from the group consisting of: (i) polyalkylene oxide alkyl ether: (ii) siloxane polyalkyleneoxide copolymer; (iii) esters of fatty acid; (iv) vinylpyrrolidones and derivatives thereof; and (v) sugar-based surfactants. The present invention also provides methods of use of the mixtures and compositions disclosed herein and processes of preparing the mixtures and compositions disclosed herein.

20 Claims, 10 Drawing Sheets

(56) References Cited

U.S. PATENT DOCUMENTS

| | | |
|---|---|---|
| 10,919,864 B2 | 2/2021 | Choy |
| 11,632,954 B2 | 4/2023 | Grabarnick |
| 2016/0280662 A1 | 9/2016 | Choy |
| 2022/0104489 A1 | 4/2022 | Klittich |
| 2022/0104490 A1 | 4/2022 | Owen |
| 2022/0110323 A1 | 4/2022 | Owen |
| 2022/0117229 A1 | 4/2022 | Owen |
| 2022/0248673 A1 | 8/2022 | Shabtai |
| 2023/0104954 A1 | 4/2023 | Alasibi |
| 2023/0143040 A1 | 5/2023 | Suez |
| 2023/0292746 A1 | 9/2023 | Yardeni |

FOREIGN PATENT DOCUMENTS

| | | | |
|---|---|---|---|
| WO | WO 2017/072166 A1 | 5/2017 | |
| WO | WO 2017/155090 A1 | 9/2017 | |
| WO | WO 2017/155091 A1 | 9/2017 | |
| WO | WO 2022/162591 A1 | 8/2022 | |
| WO | WO 2022/234487 A9 | 11/2022 | |
| WO | WO 2023/042126 A1 | 3/2023 | |
| WO | WO 2023/166485 A1 | 9/2023 | |
| WO | WO 2023/228148 A1 | 11/2023 | |
| WO | WO 2024/028812 A1 | 2/2024 | |

OTHER PUBLICATIONS

Feb. 21, 2022 Office Action issued by the Argentinian Patent Office in connection with Argentinian Patent Application No. 20190103240.
Jul. 20, 2022 Response to Office Action filed in connection with Argentinian Patent Application No. 20190103240.
Jul. 26, 2022 Response to First Office Action filed in connection with Chinese Application No. 201980087412.4.
Sep. 5, 2022 Second Office Action issued by the China National Intellectual Property Administration in connection with Chinese Application No. 201980087412.4 (including English translation).
Oct. 18, 2022 First Examination Report issued by the Indian Patent Office in connection with Indian Patent Application No. 202117023928.
Dec. 2, 2022 Substantive Examination Stage 1 issued by the Indonesian Patent Office in connection with Indonesian Patent Application No. P00202104091 (including English translation).
Dec. 6, 2022 First Office Action issued by the National Institute of Industrial Property of Chile in connection with Chilean Patent Application No. 202101173 (including English translation).
Jan. 20, 2023 Response to Second Office Action filed in connection with the Chinese Application No. 201980087412.4.
Feb. 15, 2023 Decision of Rejection issued by the China National Intellectual Property Administration in connection with Chinese Application No. 201980087412.4 (including English translation).
Mar. 22, 2023 Official Action issued by the Eurasian Patent Office in connection with Eurasian Patent Application No. 202191250 (including English translation).
May 1, 2023 Response to Substantive Examination Stage 1 filed in connection with Indonesian Patent Application No. P00202104091.
May 26, 2023 Preliminary Office Action issued by the Brazilian Patent and Trademark Office in connection with Brazilian Patent Application No. BR 11 2021 008755 9 (including English translation).
May 31, 2023 Response to First Office Action filed in connection with Chilean Patent Application No. 202101173.
Jun. 2, 2023 Response to Decision of Rejection filed in connection with Chinese Application No. 201980087412.4.
Jul. 19, 2023 Response to First Examination Report filed in connection with Indian Patent Application No. 202117023928.
Aug. 23, 2023 First Office Action issued by the Colombian Patent Office in connection with Colombian Patent Application No. NC2021/0007328 (including English summary).
Sep. 1, 2023 Response to Preliminary Office Action filed in connection with Brazilian Patent Application No. BR 11 2021 008755 9.
Sep. 4, 2023 Second Office Action issued by the National Institute of Industrial Property of Chile in connection with Chilean Patent Application No. 202101173 (including English summary).
Sep. 22, 2023 Response to Official Action filed in connection with Eurasian Patent Application No. 202191250.
Oct. 12, 2023 Office Action issued by the Israeli Patent Office in connection with Israeli Patent Application No. 282939 (including English translation).
Oct. 25, 2023 Office Action issued by the Taiwanese Intellectual Property Office in connection with Taiwanese Patent Application No. 108139931 (including English translation).
Oct. 31, 2023 Notice of Reason for Rejection issued by the Japanese Patent Office in connection with Japanese Patent Application No. 2021-524181 (including English translation).
Dec. 7, 2023 Response to Second Office Action filed in connection with Chilean Patent Application No. 202101173.
Dec. 25, 2023 Office Action issued by the Eurasian Patent Office in connection with Eurasian Patent Application No. 202191250 (including English translation).
Jan. 12, 2024 Response to First Office Action filed in connection with Colombian Patent Application No. NC2021/0007328.
Jan. 25, 2024 Response to Oct. 25, 2023 Office Action filed in connection with Taiwanese Patent Application No. 108139931.
Feb. 13, 2024 Response to Office Action filed in connection with Israeli Patent Application No. 282939.
Feb. 23, 2024 Communication Pursuant to Article 94 (3) EPC issued by the European Patent Office in connection with European Patent Application No. 19802276.6.
Mar. 27, 2024 Hearing Notice issued by the Indian Patent Office in connection with Indian Patent Application No. 202117023928.
Apr. 1, 2024 Response to Notice of Reason for Rejection filed in connection with Japanese Patent Application No. 2021-524181.
International Preliminary Report on Patentability issued May 11, 2021 in connection with PCT International Application No. PCT/IB2019/059456.
International Search Report issued Jan. 28, 2020 in connection with PCT International Application No. PCT/IB2019/059456.
Written Opinion of the International Searching Authority issued Jan. 28, 2020 in connection with PCT International Application No. PCT/IB2019/059456.
Jan. 30, 2024 Second Office Action issued by the Taiwanese Patent Office in connection with Taiwanese U.S. Appl. No. 10/831,993 (including English translation).
Jul. 10, 2024 Written Submission filed in connection with Indian Patent Application No. 202117023928.
Aug. 6, 2024 Notice of Reason for Rejection issued by the Japanese Patent Office in connection with Japanese Patent Application No. 2021-524181 (including English translation).
Sep. 2, 2024 Patent Certificate issued by the Israeli Patent Office in connection with Israeli Patent No. 282939.
Oct. 11, 2024 Second Office Action issued by the Bolivian Patent Office in connection with Bolivian Patent Application No. SP 188-2019 (including English summary).
Oct. 21, 2024 Notice of Non-Final Rejection issued by the Korean Intellectual Property Office in connection with Korean Patent Application No. 10-2021-7016434 (including English translation).
Oct. 28, 2024 Patent Certificate issued by the Indian Patent Office in connection with Indian Patent No. 553289.
Nov. 5, 2024 First Office Action issued by the Costa Rican Patent Office in connection with Costa Rican Patent Application No. 2021-0270 (including English summary).
Nov. 6, 2024 Office Action issued by the Canadian Intellectual Property Office in connection with Canadian Patent Application No. 3118729.
Nov. 26, 2024 First Examination Report issued by the Australian Patent Office in connection with Australian Patent Application No. 2019374510.
Jan. 7, 2025 First Office Action issued by the Chilean Patent Office in connection with Chilean Patent Application No. 202301663 (including English translation).

MIXTURES AND COMPOSITIONS COMPRISING 5-FLUORO-4-IMINO-3-METHYL-1-TOSYL-3,4-DIHYDROPYRIMIDIN-2-ONE, AND METHODS OF USE THEREOF

CROSS-REFERENCE TO RELATED APPLICATIONS

This application is a § 371 national stage of PCT International Application No. PCT/IB2019/059456, filed Nov. 4, 2019, claiming the benefit of U.S. Provisional Application No. 62/755,866, filed Nov. 5, 2018, the contents of each of which are hereby incorporated by reference into the application.

Throughout this application various publications are referenced. The disclosures of these documents in their entireties are hereby incorporated by reference into this application in order to more fully describe the state of the art to which this invention pertains.

BACKGROUND

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop, and consequently, increase the value of the crop. In most situations, the increase in value of the crop is worth at least three times the cost of the use of the fungicide.

5-fluoro-4-imino-3-methyl-1-tosyl-3,4-dihydropyrimidin-2(1H)-one (compound of Formula I) is a fungicide which provides control of a variety of pathogens affecting economically important crops including, but not limited to, the causal agent of leaf blotch in wheat, *Zymoseptoria tritici*, (SEPTTR) and diseases caused by fungi of the classes Ascomycetes and Basidiomycetes.

Uses of N3-substituted-N1-sulfonyl-5-fluoropyrimidinone derivatives as fungicides were described in U.S. Pat. No. 8,263,603, issued Sep. 11, 2012, the content of which is incorporated herein by reference in its entirety. Methods of preparation of 5-fluoro-4-imino-3-methyl-1-tosyl-3,4-dihydropyrimidin-2(1H)-one were described in U.S. Pat. No. 9,850,215, issued Dec. 26, 2017 and U.S. Pat. No. 9,840,476, issued Dec. 12, 2017, the contents of each of which are incorporated herein by reference in their entirety.

U.S. Pat. No. 8,263,603 also described fungicidal compositions for the control or prevention of fungal attack comprising N3-substituted-N1-sulfonyl-5-fluoropyrimidinone derivatives and a phytologically acceptable carrier material, and methods of use thereof.

Fungicidal compositions are frequently applied under various conditions and/or with other additives such as adjuvant and fertilizer. Therefore, fungicidal compositions must exhibit excellent chemical stability and a high level of physical stability during the preparation, storage and application process.

Often in agriculture, the compositions are diluted with water prior to use. Liquid compositions are much easier to dilute and disperse in water.

There is currently no stable liquid composition available in the art for 5-fluoro-4-imino-3-methyl-1-tosyl-3,4-dihydropyrimidin-2(1H)-one. In view of the exceptional efficacy of 5-fluoro-4-imino-3-methyl-1-tosyl-3,4-dihydropyrimidin-2(1H)-one in controlling and/or preventing fungal attack on a plant, there is a significant need in the art for a stable liquid composition comprising 5-fluoro-4-imino-3-methyl-1-tosyl-3,4-dihydropyrimidin-2(1H)-one.

Sometimes, the biological activity and efficacy of the fungicide is limited for various reasons such as rapid drifting, limited penetration into leaves and high surface tension/low spreading. The efficacy of the active compound can be influenced and enhanced by adding adjuvant(s).

Adjuvants are inert chemicals which are added for increasing performance of the active ingredient and composition thereof. Adjuvants affect the condition for absorption of the active ingredient and the delivery properties thereof which leads to increased efficacy and enhanced activity of the active ingredient. For example, an adjuvant can enhance the efficacy of active ingredients; e.g, modifies properties of the spray solution to improve deposition on the leaf of the fungicide.

The use of adjuvant suitable for the active ingredient and composition thereof often determines whether or not the active ingredient can be used and can act in its full efficacy after application. The adjuvant is required to increase the reservoir of "available" material for uptake on the leaf surface. Such adjuvants are often non-ionic surfactants or various types of oil.

U.S. Pat. No. 8,263,603 disclosed that the formulations comprising N3-substituted-N1-sulfonyl-5-fluoropyrimidinone derivatives described therein may additionally contain adjuvant surfactants to enhance deposition, wetting and penetration of the compounds onto the target crop and organism. Improving on U.S. Pat. No. 8,263,603, the inventors of the subject application found selected adjuvants that are particularly effective for enhancing the fungicidal efficacy of 5-fluoro-4-imino-3-methyl-1-tosyl-3,4-dihydropyrimidin-2(1H)-one.

SUMMARY OF THE INVENTION

The present invention provides a stable, liquid composition comprising:
(a) a fungicidally effective amount of a compound of Formula I:

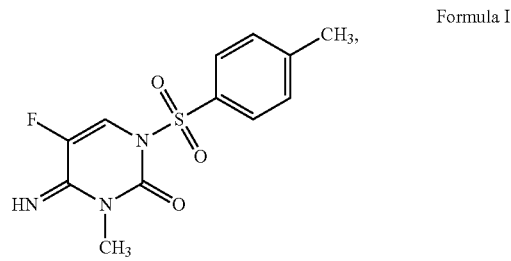 [SMILES: Cc1ccc(S(=O)(=O)n2cc(F)c(=N)n(C)c2=O)cc1]

Formula I and (b) a liquid carrier.

In some embodiments, the solubility of the compound of Formula I in the liquid carrier is less than 5000 ppm. In some embodiments, the solubility of the compound of Formula I in the liquid carrier is less than 1000 ppm. In some embodiments, the composition comprises at least one stabilizing surfactant. In some embodiments, the pH value of the composition in the presence of water is in the range of 5 to 7.5. In some embodiments, the composition has a water content of less than 0.5% by weight based on the total weight of the composition. In some embodiments, the composition has a viscosity of at least 500 cP (or in mPa·s units). In some embodiments, the composition has a viscosity of 500 cP-3000 cP.

The present invention provides a fungicidal mixture comprising:
(a) a fungicidally effective amount of a compound of Formula I:

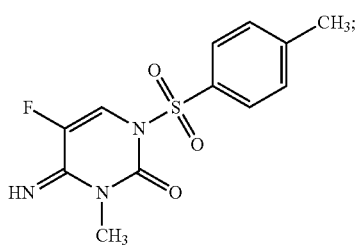

Formula I and
(b) at least one adjuvant selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof; and
(v) sugar-based surfactants.

The present invention also provides a method for the control and/or prevention of fungal pathogen attack on a plant comprising applying any one of the compositions or mixtures described herein to soil, plant, root, foliage, seed, locus of the fungus, and/or a locus in which the infestation is to be prevented so as to thereby control and/or prevent fungal pathogen attack on a plant.

The present invention also provides a method for the control and/or prevention of plant and/or soil fungal diseases comprising applying any one of the compositions or mixtures described herein to soil, plant, root, foliage, seed, locus of the fungus, and/or a locus in which the infestation is to be prevented so as to thereby control and/or prevent plant and/or soil fungal diseases.

The present invention also provides a method of controlling and/or preventing fungal pathogen attack on a plant comprising applying a fungicidally effective amount of a compound having Formula (I):

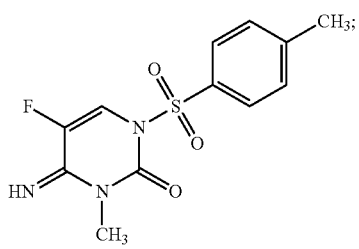

Formula I and at least one adjuvant to soil, plant, root, foliage, seed, locus of the fungus, and/or a locus in which the infestation is to be prevented so as to thereby control and/or prevent fungal pathogen attack on the plant, wherein the adjuvant is selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof; and
(v) sugar-based surfactants.

The present invention also provides a method of controlling and/or preventing plant and/or soil fungal diseases comprising applying a fungicidally effective amount of a compound having Formula (I):

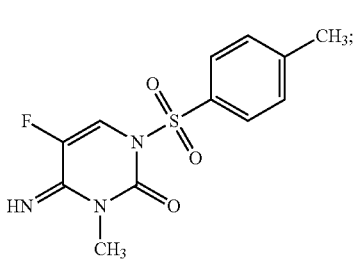

Formula I and at least one adjuvant to soil, plant, root, foliage, seed, locus of the fungus, and/or a locus in which the infestation is to be prevented so as to thereby control and/or prevent plant and/or soil fungal diseases, wherein the adjuvant is selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof; and
(v) sugar-based surfactants.

The present invention provides a method for improving biological activity of a compound of Formula I against fungal pathogen, the method comprising applying the compound of Formula I:

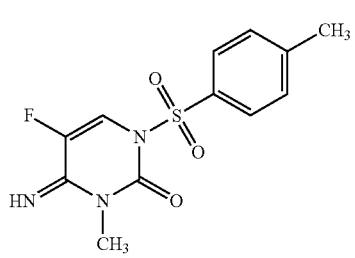

Formula I in presence of at least one adjuvant, wherein the adjuvant is selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof; and
(v) sugar-based surfactants so as to thereby improve biological activity of the compound of Formula I.

The present invention also provides a method for increasing stability of a liquid composition comprising a compound of Formula I:

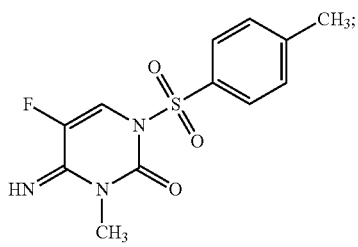
Formula I and a liquid carrier, wherein the method comprises selecting a liquid carrier wherein the solubility of the compound of Formula I in the liquid carrier is less than 5000 ppm. In some embodiments, the solubility of compound of Formula I in the liquid carrier is less than 1000 ppm.

The present invention also provides a method for increasing stability of a liquid composition comprising a compound of Formula I:

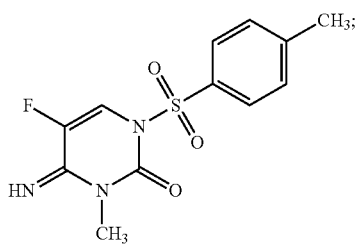
Formula I and a liquid carrier, wherein the method comprises maintaining the pH value of the composition in the range of 5 to 7.5.

The present invention also provides use of pH adjuster for increasing the stability of an aqueous suspension concentrate (SC) composition comprising a compound of Formula I:

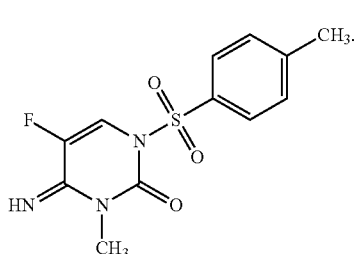
Formula I

The present invention also provides use of pH adjuster for increasing the stability of an aqueous suspoemulsion (SE) composition comprising a compound of Formula I:

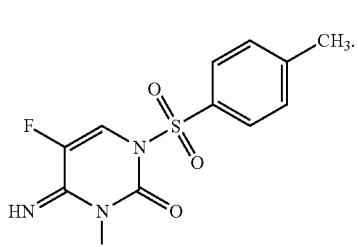
Formula I

The present invention also provides a method for increasing stability of a non-aqueous liquid composition comprising a compound of Formula I:

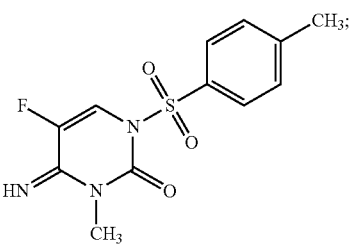
Formula I and a liquid carrier, wherein the method comprises maintaining the water content of the composition to less than 0.5% by weight based on the total weight of the composition.

The present invention also provides a method for increasing stability of a non-aqueous liquid composition comprising a compound of Formula I:

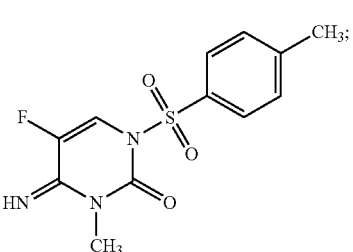
Formula I and a liquid carrier, wherein the method comprises maintaining the water content of the composition to less than 0.2% by weight based on the total weight of the composition.

The present invention also provides a method for increasing stability of a liquid composition comprising a compound of Formula I:

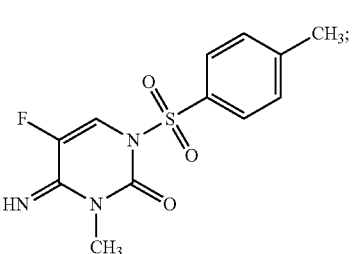
Formula I and a liquid carrier, wherein the method comprises adding (i) at least one stabilizing surfactant having crystal growth inhibiting property or (ii) a stabilizing system having a crystal growth inhibiting property to the liquid composition.

The present invention also provides use of at least one stabilizing surfactant having structure of polyalkylene oxide polyaryl ether for controlling solubility and/or degradation of compound of Formula I:

Formula I

[Chemical structure of Formula I]

The present invention also provides a method for increasing stability of a liquid composition comprising a compound of Formula I:

Formula I

[Chemical structure of Formula I]

and a liquid carrier, wherein the method comprises formulating the composition to have a viscosity of at least 500 cP.

The present invention provides a process for preparing the suspension concentrate (SC) composition disclosed herein, the process comprises the steps:
(1) mixing the agriculturally acceptable inert additives and an aqueous liquid carrier to obtain a premix;
(2) adding the compound of Formula I to the premix obtained in step (1) to obtain a mixture: and
(3) milling the resulting mixture of step (2) to obtain the desired composition.

In some embodiments, the process comprises adding additional additive to the mixture of step (2) prior to milling the mixture.

The present invention provides a process for preparing the suspoemulsion (SE) composition disclosed herein, the process comprises the steps:
(1) mixing the agriculturally acceptable inert additives and an aqueous liquid carrier to obtain a premix;
(2) adding the compound of Formula I and at least one adjuvant to the premix obtained in step (1) to obtain a mixture; and
(3) milling the resulting mixture of step (2) to obtain the desired composition.

The present invention provides a process for preparing the oil dispersion (OD) composition disclosed herein, the process comprises the steps:
(1) mixing the agriculturally acceptable inert additives and a non-aqueous liquid carrier to obtain a premix;
(2) adding the compound of Formula I to the premix obtained in step (1) to obtain a mixture; and
(3) milling the resulting mixture of step (2) to obtain the desired composition.

The present invention provides a process for preparing the emulsifiable concentrate (EC) composition disclosed herein, the process comprises the steps:
(1) mixing the agriculturally acceptable inert additives and a non-aqueous liquid carrier to obtain a premix;
(2) adding the compound of Formula I to the premix obtained in step (1) to obtain a mixture; and
(3) filtering the solution of step (2) to obtain the desired composition.

DETAILED DESCRIPTION OF THE INVENTION

Definitions

Figure 1:
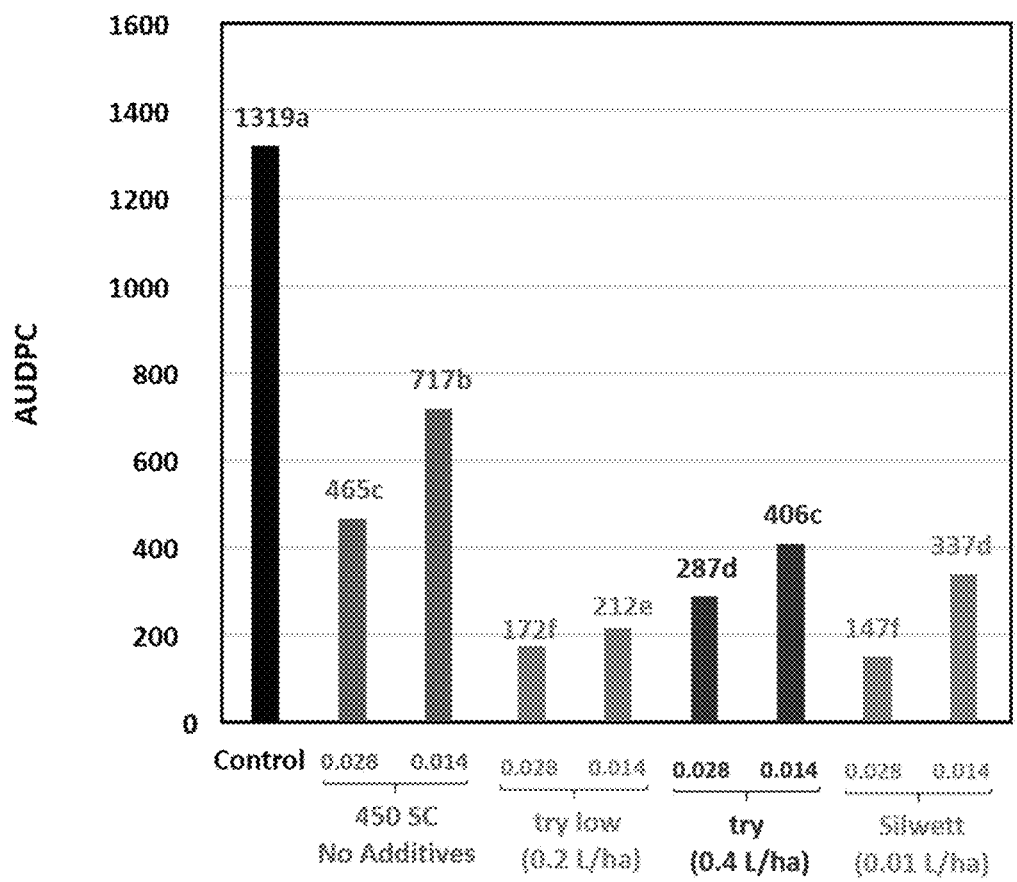
FIG. 1. Effect of Trycol® low (refers to 0.2 L/ha), Trycol® (refers to 0.4 L/ha) or Silwett as adjuvant on the activity of compound of Formula I. Comparison of the Area Under Disease Progress Curve (AUDPC) determined from the intensity of infection measured 21 dpi (days post infection) of $Z.$ $tritici$ strain Mg Tri-R6 moderately resistant to DMI fungicides and highly resistant to QoI fungicides of wheat plants cv. Alixan untreated or treated with compound of Formula I 450 suspension concentrate composition used at 2 rates (0.028 and 0.014 L/ha) alone (no adjuvant) or with adjuvant as tank mix. Values of the same timing of observation followed by the same letter are not significantly different according to the Newman and Keuls test ($p<0.05$).

Unless defined otherwise, all technical and scientific terms used herein have the meaning commonly understood by persons of ordinary skill in the art to which this subject matter pertains.

The term "a" or "an" as used herein includes the singular and the plural, unless specifically stated otherwise. Therefore, the terms "a," "an," or "at least one" can be used interchangeably in this application.

As used herein, the term "about" when used in connection with a numerical value includes ±10% from the indicated value. In addition, all ranges directed to the same component or property herein are inclusive of the endpoints, are independently combinable, and include all intermediate points and ranges. It is understood that where a parameter range is provided, all integers within that range, and tenths thereof, are also provided by the invention. For example, "0.1-80%" includes 0.1%, 0.2%, 0.3%, etc, up to 80%.

As used herein the term "plant" or "crop" includes reference to whole plants, plant organs (e.g, leaves, stems, twigs, roots, trunks, limbs, shoots, fruits etc.), plant cells, or plant seeds. This term also encompasses plant crops such as fruits. In yet another embodiment, the term "plant" may include the propagation material thereof, which may include all the generative parts of the plant such as seeds and vegetative plant material such as cuttings and tubers, which can be used for the multiplication of the plant. This includes seeds, tubers, spores, corms, bulbs, rhizomes, sprouts basal shoots, stolons, and buds and other parts of plants, including seedlings and young plants, which are to be transplanted after germination or after emergence from soil.

As used herein, the term "locus" includes not only areas in which the infestation is to be controlled, but also areas in which the infestation is to be prevented and also to areas under cultivation.

As used herein, the term "mixture" or "combination" refers, but is not limited to, a combination in any physical form, e.g., blend, solution, alloy, or the like.

As used herein, the term "effective amount" refers to an amount of the compound that, when applied, is sufficient to achieve a good level of control.

As used herein, the phrase "agrochemically acceptable" means which is known and accepted in the art for use in agricultural/pesticidal use.

As used herein, the term "adjuvant" is broadly defined as any substance that itself is not a fungicide but which enhances or is intended to enhance the effectiveness of the fungicide with which it is used. Adjuvants may be understood to include, but are not limited to, spreading agents, penetrants, compatibility agents, and drift retardants. As used herein, the term "additive" is defined as any substance that itself is not a fungicide but is added to the composition such as sticking agents, surfactants, synergists, buffers, acidifiers, defoaming agents and thickeners.

As used herein, the term "built-in" means that all components such as pesticide, adjuvant and other additives are in the same composition.

As used herein, the term "tank mix" means that at least one pesticide and/or additive and/or adjuvant are mixed in the spray tank prior to the application or at the time of spray application.

As used herein, the phrase "agriculturally acceptable carrier" means carriers which are known and accepted in the art for the formation of compositions for agricultural or horticultural use.

As used herein, the term "thickener" refers to an agent that increases the viscosity of a liquid composition without essentially changing other properties of the composition.

As used herein, the term "stable" refers to chemical stability, physical stability, or both.

As used herein, the term "stable" when used in connection with chemical stability, e.g, chemically stable, means that the composition meets the chemical stability standards set forth by the Food and Agriculture Organization of the United Nations (FAO) in the Manual on Development and Use of FAO and WHO Specification for Pesticides (First Edition—Third Revision) (the "FAO/WHO Manual") (available at http://www.fao.gov/agriculture/crops/thematic-sitemap/theme/pests/jmps/manual/en/), the entire content of which is hereby incorporate by reference into the subject application. As described in the FAO/WHO Manual, a composition is stable if no significant degradation of the active ingredients in the composition is observable after 14 days of storage at a temperature of 54±2° C., after 4 weeks of storage at a temperature of 50±2° C., after 6 weeks of storage at a temperature of 45±2° C., after 8 weeks of storage at a temperature of 40±2° C., after 12 weeks of storage at a temperature of 35±2° C., or after 18 weeks of storage at a temperature of 30±2° C. The amount of degradation permitted before the degradation is considered to be significant depends on the concentration of the active ingredients in the composition. As described in the FAO/WHO Manual, for a composition comprising above 25 up to 100 g/L of active ingredients, degradation of up to 10% of the active ingredients is considered no significant degradation; for a composition comprising above 100 up to 250 g/L of active ingredients, degradation of up to 6% of the active ingredients is considered no significant degradation; for a composition comprising above 250 up to 500 g/L of active ingredients, degradation of up to 5% of the active ingredients is considered no significant degradation; and for a composition comprising above 500 g/L of active ingredients, degradation of up to 25 g/L of the active ingredients is considered no significant degradation.

As used herein, the term "stable" when used in connection with physical stability, e.g, physically stable, and when used in connection with a composition, means that the composition meets the physical stability standards set forth by the Collaborative International Pesticides Analytical Council (CIPAC). The CIPAC is an international, organization that promote international agreements on methods for the analysis of pesticides and physico-chemical test methods for formulations. Methods adopted by the CIPAC are published in the CIPAC Handbooks, available online at https://www.cipac.org/index.php/methods-publications, the entire content of each method is hereby incorporated by reference into the subject application.

As used herein, the term "stabilizing surfactant" is defined as any surfactant that increases the physical and/or chemical stability of the compound of Formula I when added to a liquid composition comprising the compound of Formula I. In some embodiments, the stabilizing surfactant is effective for inhibiting crystal growth.

As used herein, the term "low water content" when used in connection with a surfactant or carrier means that the surfactant or carrier solubilizes water in an amount of less than 25 g/L.

As used herein, the term "w/w" means percentage by weight based on the total weight of the composition or mixture.

As used herein, the term "liquid" means a liquid that is not a gas.

The compound of Formula I is a pro-pesticide derivative of N3-Me-5-FU comprising sensitive groups such as sulfonyl group and imine on positions N1 and C4 accordingly. These "groups" lead to highly sensitive unstable structures which require development of specific conditions for stabilizing the compound of Formula I in a liquid composition. In addition, the compound of Formula I has several crystal forms and has a tendency to form crystals which are less available and affect the penetration rate into the target.

Formulating compositions comprising active ingredient often requires adding an agriculturally acceptable inert additive. Such as surfactants, dispersants, emulsifiers, wetting agents, antifoams, solvents, co-solvent, light stabilizers, UV absorbers, radical scavengers and antioxidants, adhesives, neutralizers, thickeners, binders, sequestrates, biocides, buffers preservatives, and anti-freeze agents. The addition of an additive affects the solubility of the active ingredient and leads to chemically and physically unstable compositions.

Solvent and additives, which can be used for the compound of Formula I, should be neutral, i.e. without an active functional group which can affect the stability of and cause degradation of the compound of Formula I. Solvent and/or additive used for formulating the compound for Formula I should not be reactive towards the compound of Formula I.

Functional groups which can affect the stability of the compound of Formula I are groups containing N and/or O, such as S—O, OH and non-sterically hindered amide and amine. It was found that chemical stability of the compound of Formula I in amide solvent depends on the substitute on the amide. The reactivity of the solvent and/or the additive is critical in formulating a stable composition comprising the compound of Formula I. Reactive nucleophilic groups are groups such as hydroxyl group with bond dissociation energies less than 120 Kcal/mol, a weak dissociate hydrogen bond, or an acidic functional group.

The concentration of water in the composition is another critical factor for chemical and/or physical stability.

For the abovementioned reasons, formulating compound of Formula I in a liquid composition is particularly challenging.

It was found that the stability of the compound of Formula I in liquid carrier may be improved by controlling the solubility of the compound of Formula I in the liquid carrier, controlling the pH of the composition in water environment, controlling the water content of the composition, adding surfactants effective for preventing crystals growth, and/or controlling the viscosity of the composition.

Stable liquid compositions comprising the compound of Formula I, as well as their methods of use and processes of preparation, are described below.

Stable Liquid Compositions:

The present invention provides a stable, liquid composition comprising:

(a) a fungicidally effective amount of a compound of Formula I:

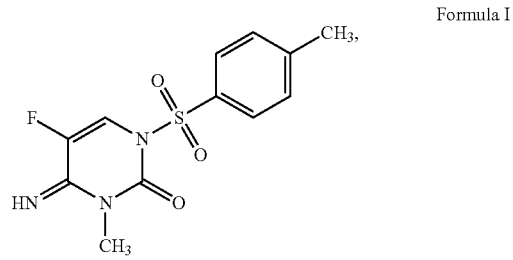 [SMILES: Cc1ccc(S(=O)(=O)n2cc(F)c(=N)n(C)c2=O)cc1]

and (b) a liquid carrier.

In some embodiments, the solubility of the compound of Formula I in the liquid carrier is less than 5000 ppm. In some embodiments, the solubility of the compound of Formula I in the liquid carrier is less than 1000 ppm. In some embodiments, the solubility of compound of Formula I in the liquid carrier is in the range of 50 to 500 ppm. In some embodiments, the solubility of compound of Formula I in the liquid carrier is about 200 ppm. In some embodiments, the solubility of compound of Formula I in the liquid carrier is about 80 ppm.

In some embodiments, the composition comprises at least one stabilizing surfactant. In some embodiments, the composition comprises at least two stabilizing surfactants. In some embodiments, the composition comprises two stabilizing surfactants. In some embodiments, the composition further comprises a stabilizing system.

In some embodiments, the composition comprises at least one anionic stabilizing surfactant. In some embodiments, the composition comprises at least one non-ionic stabilizing surfactant. In some embodiments, the composition comprises two stabilizing surfactants. In some embodiments, the composition comprises a stabilizing system. In some embodiments, the composition comprises combination of a non-ionic stabilizing surfactant and an ionic stabilizing surfactant.

In some embodiments, the stabilizing surfactant(s) affects the solubility of the compound of Formula I in the liquid carrier.

In some embodiments, the pH of the composition is in the range of 5 to 7.5. In some embodiments, the pH of the composition is in the range of 6 to 7. In some embodiment, the pH of the composition is about 5. In some embodiments, the pH of the composition is about 5.5. In some embodiments, the pH of the composition is about 5.8. In some embodiments, the pH of the composition is about 6. In some embodiments, the pH of the composition is about 6.5. In some embodiments, the pH of the composition is about 7. In some embodiments, the pH of the composition is about 7.5.

In some embodiments, the pH of the composition is measured when the composition is in the presence of water. Water may be present in the composition as the liquid carrier. Water may also be present in the composition as a result of dilution or wetting.

In some embodiments, the pH of the composition is measured without further dilution and/or wetting. In some embodiments, the pH of the composition is measured after dilution and/or wetting.

In some embodiments, the liquid carrier is water and the pH of the composition is measured without further dilution and/or wetting. In some embodiments, wherein the liquid carrier is a non-aqueous carrier and the pH of the composition is measured after dilution and/or wetting.

In some embodiments, the composition comprises a pH adjuster.

The chemical stability of the composition is affected by the pH of the composition.

When the liquid carrier is non-aqueous, the amount of water in the composition should be less than 0.5% by weight based on the total weight of the composition, preferably, less than 0.2% by weight based on the total weight of the composition.

In some embodiments, the non-aqueous composition has a water content of less than 0.5% by weight based on the total weight of the composition. In some embodiments, the non-aqueous composition has a water content of less than 0.4% by weight based on the total weight of the composition. In some embodiments, the non-aqueous composition has a water content of less than 0.3% by weight based on the total weight of the composition. In some embodiments, the non-aqueous composition has a water content of less than 0.2% by weight based on the total weight of the composition. In some embodiments, the non-aqueous composition has a water content of less than 0.1% by weight based on the total weight of the composition.

An amount of water less than 0.5% by weight based on the total weight of the composition, preferably less than 0.2% by weight based on the total weight of the composition, can be achieved using methods including but not limited to drying component(s) of the composition prior to adding it to the composition and/or lowering the water content of the components in the composition (both active and non-active components). The water content of the composition may be also be controlled by using low water content surfactants, low water content carrier, water scavenger and/or drying agent.

In some embodiments, the composition comprises a low water content surfactant. In some embodiments, the composition comprises a low water content carrier. In some embodiments, the composition comprises at least one water scavenger. In some embodiments, the composition comprises at least one drying agent. In some embodiments, the low water content surfactant, low water content carrier, water scavenger and/or drying agent are added to the composition after the composition is dried.

In some embodiments, the water scavenger is selected from the group consisting of tetraethyl orthosilicate, Dynasylan® and a combination thereof. In some embodiments, the Dynasylan® is Dynasylan® P. These water scavengers reduce the water content of non-aqueous liquid composition to below 0.5% by weight which improves the composition's stability. These water scavengers reduce the water content of the OD composition to below 0.5% by weight which improves the composition's stability. These water scavengers reduce the water content of the EC composition to below 0.5% by weight which improves the composition's stability.

In some embodiments, the amount of water scavenger in the composition is between about 0.5-7.5% by weight based on the total weight of the composition.

In some embodiments, the composition has a viscosity of at least 500 cP. In some embodiments, the composition has a viscosity of 500 cP-3000 cP. In some embodiments, the composition has a viscosity of 500 cP-2500 cP. In some embodiments, the composition has a viscosity of 800 cP-3000 cP. In some embodiments, the composition has a viscosity of 1600 cP-2200 cP. In some embodiments, the composition has a viscosity of equal to or less than 3000 cP.

In some embodiments, the composition has a viscosity of about 500 cP-1000 cP. In some embodiments, the composition has a viscosity of about 1000 cP-1500 cP. In some embodiments, the composition has a viscosity of about 1500 cP-2000 cP. In some embodiments, the composition has a viscosity of about 2000 cP-2500 cP. In some embodiments, the composition has a viscosity of about 2500 cP-3000 cP.

In some embodiments, the composition has a viscosity of about 500 cP, about 600 cP, about 700 cP, about 800 cP, about 900 cP, about 1000 cP, about 1100 cP, about 1200 cP, about 1300 cP, about 1400 cP, about 1500 cP, about 1600 cP, about 1700 cP, about 1800 cP, about 1900 cP about 2000 cP, about 2100 cP, about 2200 cP, about 2300 cP, about 2400 cP about 2500 cP, about 2600 cP, about 2700 cP, about 2800 cP, about 2900 cP, about 3000 cP.

In some embodiments, the liquid carrier is an aqueous liquid carrier. In some embodiments, the aqueous liquid carrier is water.

In some embodiments, the liquid carrier is a non-aqueous liquid carrier.

In some embodiments, the solubility of the compound of Formula I in the aqueous liquid carrier is less than 5000 ppm. In some embodiments, the solubility of the compound of Formula I in the non-aqueous carrier is less than 5000 ppm.

In some embodiments, the compound of Formula I is in the form of solid particles. In some embodiments, the solid particles of the compound of Formula I is suspended in the aqueous carrier. In some embodiments, the solid particles of the compound of Formula I is suspended in the non-aqueous carrier.

In some embodiments, the compound of Formula I is dissolved in the non-aqueous carrier.

When the solid particles of the compound of Formula I is suspended in the aqueous carrier, the composition is suspension concentrate (SC).

When the SC composition comprising an aqueous carrier further comprises a non-aqueous liquid component, the SC composition is a suspoemulsion (SE). When solid particles of the compound of Formula I is suspended in the aqueous carrier and the composition further comprises a non-aqueous liquid component, the composition is a suspoemulsion (SE). The non-aqueous liquid component may be but is not limited to adjuvant, carrier of the adjuvant and/or any additive. In some embodiment, the non-aqueous liquid component is an adjuvant. The SC composition is an SE composition when the SC composition further comprises a non-aqueous liquid component in the aqueous carrier.

When the solid particles of the compound of Formula I is suspended in the non-aqueous carrier, the composition is oil dispersion (OD).

When the compound of Formula I is dissolved in the non-aqueous carrier the composition is an emulsifiable concentrate (EC).

In some embodiments, the stable liquid composition is a suspension concentrate (SC) composition. In some embodiments, the composition is a suspoemulsion. (SE), composition. In some embodiments, the composition is an oil dispersion (OD) composition. In some embodiments, the composition is an emulsifiable concentrate (EC) composition.

In some embodiments, the stable liquid composition is a suspension concentrate (SC) composition comprising at least one stabilizing surfactant. In some embodiments, the stable liquid composition is a suspension concentrate (SC) composition comprising two stabilizing surfactants.

In some embodiments, the stable liquid composition is a suspoemulsion (SE) composition comprising at least one stabilizing surfactant. In some embodiments, the stable liquid composition is a suspoemulsion (SE) composition comprising two stabilizing surfactants.

In some embodiments, the stable liquid composition is a suspension concentrate (SC) composition having a pH in the range of 5 to 7.5.

In some embodiments, the stable liquid composition is a suspoemulsion (SE) composition having a pH in the range of 5 to 7.5.

In some embodiments, the stable liquid composition is an oil dispersion (OD) composition with a water content of less than 0.5% by weight based on the total weight of the composition.

In some embodiments, the stable liquid composition is an emulsifiable concentrate (EC) composition with a water content of less than 0.5% by weight based on the total weight of the composition.

In some embodiments, the composition comprises an aqueous carrier and the aqueous composition has a viscosity of at least 500 cP. In some embodiments, the composition comprises an aqueous carrier and the aqueous composition has a viscosity of equal to or less than 3000 cP.

In some embodiments, the stable liquid composition is a suspension concentrate (SC) composition and the SC composition has a viscosity of at least 500 cP. In some embodiments, the stable liquid composition is a suspension concentrate (SC) composition and the SC composition has a viscosity of 800 cP-3000 cP. In some embodiments, the stable liquid composition is a suspension concentrate (SC) composition and the SC composition has a viscosity of 1600 cP-2200 cP. In some embodiments, the stable liquid composition is a suspension concentrate (SC) composition and the SC composition has a viscosity of equal to or less than 3000 cP.

In some embodiments, the composition comprises a non-aqueous liquid carrier and the non-aqueous composition has a viscosity of at least 500 cP. In some embodiments, the composition comprises a non-aqueous liquid carrier and the non-aqueous composition has a viscosity of equal to or less than 3000 cP.

In some embodiments, the stable liquid composition is an oil dispersion (OD) composition and the OD composition has a viscosity of at least 500 cP. In some embodiments, the stable liquid composition is an oil dispersion (OD) composition and the OD composition has a viscosity of 500 cP-2500 cP. In some embodiments, the stable liquid composition is an oil dispersion (OD) composition and the OD composition has a viscosity of equal to or less than 2500 cP.

Viscosity may be measured using Collaborative International Pesticides Analytical Council (CIPAC) MT192—viscosity of liquids by rotational viscometer, the entire content of which is hereby incorporated by reference into this application. When viscosity is described in the subject application, the viscosity is measured using CIPAC MT192 using spindle 62 at 12 rpm or spindle 63 at 12 rpm.

In some embodiments, viscosity is measured using spindle 62 at 12 rpm. In some embodiments, viscosity is measured using spindle 63 at 12 rpm. In some embodiments, the composition has a viscosity of at least 500 cP when measured using CIPAC MT192 using spindle 62 at 12 rpm or using spindle 63 at 12 rpm. In some embodiments, the composition has a viscosity of 500 cP-3000 cP when measured using CIPAC MT192 using spindle 62 at 12 rpm or using spindle 63 at 12 rpm. In some embodiments, the composition has a viscosity of 500 cP-2500 cP when measured using CIPAC MT192 using spindle 62 at 12 rpm or using spindle 63 at 12 rpm. In some embodiments, the composition has a viscosity of 800 cP-3000 cP when measured using CIPAC MT192 using spindle 62 at 12 rpm or using spindle 63 at 12 rpm. In some embodiments, the composition has a viscosity of 1600 cP-2200 cP when measured using CIPAC MT192 using spindle 62 at 12 rpm or using spindle 63 at 12 rpm. In some embodiments, the composition has a viscosity of equal to or less than 3000 cP when measured using CIPAC MT192 using spindle 62 at 12 rpm or using spindle 63 at 12 rpm.

In some embodiments, the total amount of aqueous carrier in the composition ranges from about 30% to about 70% by weight based on the total weight of the composition. In some embodiments, the total amount of aqueous carrier in the composition ranges from about 40% to about 60% by weight based on the total weight of the composition. In some embodiments, the total amount of aqueous carrier in the composition ranges from about 40% to about 50% by weight based on the total weight of the composition.

In some embodiments, the total amount of aqueous carrier in the SC composition ranges from about 30% to about 70% by weight based on the total weight of the composition. In some embodiments, the total amount of aqueous carrier in the SC composition ranges from about 40% to about 60% by weight based on the total weight of the composition. In some embodiments, the total amount of aqueous carrier in the SC composition ranges from about 40% to about 50% by weight based on the total weight of the composition.

In some embodiments, the total amount of aqueous carrier in the SE composition ranges from about 30% to about 70% by weight based on the total weight of the composition. In some embodiments, the total amount of aqueous carrier in the SE composition ranges from about 40% to about 60% by weight based on the total weight of the composition. In some embodiments, the total amount of aqueous carrier in the SE composition ranges from about 40% to about 50% by weight based on the total weight of the composition.

In some embodiments, the total amount of non-aqueous carrier in the composition ranges from about 30 to about 80% by weight based on the total weight of the composition. In some embodiments, the total amount of non-aqueous carrier in the composition ranges from about 40% to about 70% by weight based on the total weight of the composition. In some embodiments, the total amount of non-aqueous carrier in the composition is about 50% by weight based on the total weight of the composition.

In some embodiments, the total amount of non-aqueous carrier in the OD composition ranges from about 30 to about 80% by weight based on the total weight of the composition. In some embodiments, the total amount of non-aqueous carrier in the OD composition ranges from about 40% to about 70% by weight based on the total weight of the composition. In some embodiments, the total amount of non-aqueous carrier in the OD composition is about 50% by weight based on the total weight of the composition.

In some embodiments, the total amount of non-aqueous carrier in the EC composition ranges from about 30 to about 80% by weight based on the total weight of the composition. In some embodiments, the total amount of non-aqueous carrier in the EC composition ranges from about 40% to about 70% by weight based on the total weight of the composition. In some embodiments, the total amount of non-aqueous carrier in the EC composition ranges from about 40% to about 80% by weight based on the total weight of the composition. In some embodiments, the total amount of non-aqueous carrier in the EC composition is about 80% by weight based on the total weight of the composition.

In some embodiments, the concentration of the compound of Formula I in the stable liquid composition is 150 g/L to 750 g/L. In some embodiments, the concentration of the compound of Formula I in the stable liquid composition is 300 g/L to 750 g/L. In some embodiments, the concentration of the compound of Formula I in the stable liquid composition is 450 g/L. In some embodiments, the concentration of the compound of Formula I in the stable liquid composition is 660 g/L.

In some embodiments, the concentration of compound of Formula I in the composition is greater than 5% by weight based on the total weight of the stable composition. In some embodiments, the concentration of compound of Formula I in the composition is greater than 10% by weight based on the total weight of the stable composition. In some embodiments, the concentration of compound of Formula I in the composition is greater than 25% by weight based on the total weight of the stable composition. In some embodiments, the concentration of compound of Formula I in the composition is greater than 50% by weight based on the total weight of the stable liquid composition.

In some embodiments, the concentration of compound of Formula I in the SC composition is greater than 25% by weight based on the total weight of the stable composition. In some embodiments, the concentration of compound of Formula I in the SC composition is greater than 50% by weight based on the total weight of the stable liquid composition.

In some embodiments, the concentration of compound of Formula I in the SE composition is greater than 25% by weight based on the total weight of the stable composition. In some embodiments, the concentration of compound of Formula I in the SE composition is greater than 50% by weight based on the total weight of the stable liquid composition.

In some embodiments, the concentration of the compound of Formula I in the OD composition is greater than 25% by weight based on the total weight of the stable composition. In some embodiments, the concentration of compound of Formula I in the OD composition is greater than 50% by weight based on the total weight of the stable liquid composition.

In some embodiments, the concentration of compound of Formula I in the EC composition is greater than 5% by weight based on the total weight of the stable liquid composition. In some embodiments, the concentration of compound of Formula I in the EC composition is greater than 10% by weight based on the total weight of the stable liquid composition. In some embodiments, the concentration of compound of Formula I in the EC composition is greater than 25% by weight based on the total weight of the stable liquid composition.

In some embodiments, the composition comprising non-aqueous carrier is free of phosphoric acid. In some embodiments, the composition is free of phosphoric acid at 2% or 5%. In some embodiments, the composition comprises 2% or less by weight of phosphoric acid. In some embodiments, the composition comprises 5% or less by weight of phosphoric acid.

In some embodiments, the composition comprising non-aqueous carrier is free of urea. In some embodiments, the composition is free of urea at 1% or 2%. In some embodiments, the composition comprises 1% or less by weight of urea. In some embodiments, the composition comprises 2% or less by weight of urea.

In some embodiments, the composition comprising non-aqueous carrier is free of propyl gallate.

In some embodiments, the composition comprising non-aqueous carrier is free of dimethyl sulfoxide (DMSO).

In some embodiments, the composition comprising non-aqueous carrier is free of morpholine.

In some embodiments, the composition comprising non-aqueous carrier is free of N-methyl pyrrolidone.

The present invention provides a stable suspension concentrate (SC) composition comprising:
  (a) a fungicidally effective amount of a compound of Formula I:

Formula I (b) an aqueous liquid carrier, and
  (c) at least one stabilizing surfactant,
wherein the composition has a pH in the range of 5 to 7.5.

The present invention provides a suspoemulsion (SE) composition comprising:
  (a) a fungicidally effective amount of a compound of Formula I:

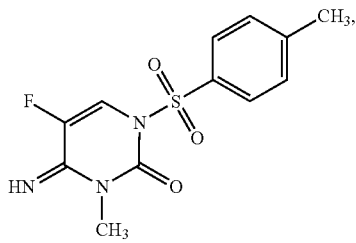

Formula I (b) an aqueous liquid carrier, and
(c) at least one stabilizing surfactant,
wherein the composition has a pH in the range of 5 to 7.5.

The present invention provides an oil dispersion (OD) composition comprising:
(a) a fungicidally effective amount of a compound of Formula I:

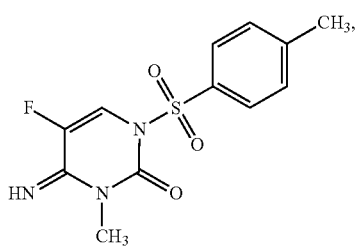

Formula I (b) non-aqueous liquid carrier, and
(c) at least one stabilizing surfactant,
wherein the water content in the composition is less than 0.5% by weight based on the total weight of the composition and/or the viscosity of the composition is at least 500 cP.

The present invention provides an emulsifiable concentrate (EC) composition comprising:
(a) a fungicidally effective amount of a compound of Formula I:

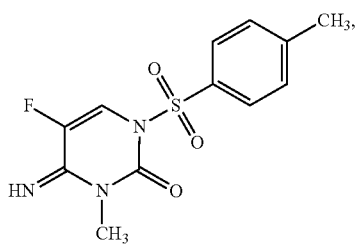

Formula I (b) non-aqueous liquid carrier, and
(c) at least one stabilizing surfactant,
wherein the water content in the composition is less than 0.5% by weight based on the total weight of the composition.

In some embodiments, the non-aqueous liquid carrier is used as an adjuvant.

(i) Compound of Formula I

The compound of Formula I of the present invention refers to any solid form including but not limited to amorphous, crystalline, solvate or hydrate.

The compound of Formula I includes crystalline forms of the compound of Formula I.

In some embodiments, the crystalline form is an anhydrous crystalline form. In some embodiments, the anhydrous crystalline form is a polymorph. In some embodiments, the anhydrous crystalline form is a pseudopolymorph.

Polymorphs of the compound of Formula I is described in PCT International Application Publication No. WO/2019/038583 (published Feb. 28, 2019), the entire content of which is hereby incorporated by reference into this application.

In some embodiments, the crystalline form is a hydrate.

In some embodiments, the crystalline form is a solvate. In some embodiments, the solvate contains 1,4-dioxane. In some embodiments, the solvate contains tetrahydrofuran. In some embodiments, the solvate contains ethyl acetate.

In some embodiments, the crystalline polymorphic form (Form I) exhibits an X-ray powder diffraction pattern having characteristic peaks at 2-theta angles of 9.08, 10.98, 14.05, 17.51, 18.75, 21.63, 23.33, 24.70, 24.83, 25.37, 26.51 and 29.23. In one embodiment, the powder X-ray diffraction pattern of Form I comprises characteristic peaks at 2-theta angles of 14.05, 17.51, 18.75, 21.63 and 26.51. In one embodiment, the powder X-ray diffraction pattern of Form I comprises characteristic peaks at 2-theta angles of 14.05, 17.51, 18.75 and 21.63.

In some embodiments, the crystalline polymorphic form (Form I) is characterized by decomposition beginning at a temperature greater than 210° C.

In some embodiments, the crystalline polymorphic form (Form I) exhibits a Differential Scanning Calorimetry (DSC) thermogram characterized by a predominant endothermic peak with a peak temperature of about 160° C., a predominant endothermic peak with an onset temperature of about 159° C., and a predominant endothermic peak with a melting enthalpy of about 110 J/g.

In one embodiment, the crystalline polymorphic form (Form II) exhibits an X-ray powder diffraction pattern having characteristic peaks at 2-theta angles of 7.98, 9.20, 9.96, 11.88, 15.99, 18.49, 21.23, 22.33, 22.59, 26.73. In one embodiment, the powder X-ray diffraction pattern of Form II comprises characteristic peaks at 2-theta angles of 9.20, 9.96, 11.88, 22.33 and 22.59. In one embodiment, the powder X-ray diffraction pattern of Form II comprises characteristic peaks at 2-theta angles of 9.20, 11.88, 22.33 and 22.59.

In one embodiment, the crystalline polymorphic form (Form II) exhibits a TG-FTIR thermogram characterized by decomposition beginning at a temperature greater than 210° C.

In one embodiment, the crystalline polymorphic form (Form II) exhibits a Differential Scanning Calorimetry (DSC) thermogram characterized by a predominant endothermic peak with a peak temperature of about 157° C., a predominant endothermic peak with an onset temperature of about 156° C., and a predominant endothermic peak with a melting enthalpy of about 112 J/g.

In one embodiment, the crystalline hydrate form (Hydrate) exhibits an X-ray powder diffraction pattern having characteristic peaks at 2-theta 5.34, 7.48, 10.68, 16.05, 21.79, 22.99, 23.19, 24.95, 26.95, 27.63. In one embodiment, the powder X-ray diffraction pattern of Hydrate comprises characteristic peaks at 2-theta angles of 5.34, 7.48, 10.68, 16.05 and 21.79. In one embodiment, the powder X-ray diffraction pattern of Hydrate comprises characteristic peaks at 2-theta angles of 5.34, 7.48, 10.68 and 16.05.

In one embodiment, the crystalline hydrate form (Hydrate) exhibits a TG-FTIR thermogram characterized by decomposition beginning at a temperature greater than 190° C.

In one embodiment, the crystalline hydrate form (Hydrate) exhibits a Differential Scanning Calorimetry (DSC) thermogram characterized by a predominant endothermic peak with a peak temperature of about 139.5° C., a predominant endothermic peak with an onset temperature of about 139° C., and a predominant endothermic peak with a melting enthalpy of about 115 J/g, wherein the DSC is measured in a sealed pan.

In one embodiment, the crystalline hydrate form (Hydrate) exhibits a Differential Scanning Calorimetry (DSC) thermogram characterized by a predominant endothermic peak with a peak temperature of about 160° C., a predominant endothermic peak with an onset temperature of about 159° C., and a predominant endothermic peak with a melting enthalpy of about 98 J/g, wherein the DSC is measured in an open pan.

In one embodiment, the crystalline solvate form (Form S5) exhibits an X-ray powder diffraction pattern having characteristic peaks at 2-theta 5.42, 7.50, 10.06, 10.82, 12.80, 16.91, 21.55, 23.13, 24.83, 26.81, 27.77. In one embodiment, the powder X-ray diffraction pattern of Form S5 comprises characteristic peaks at 2-theta angles of 5.42, 7.50, 10.06, 10.82, and 16.91. In one embodiment, the powder X-ray diffraction pattern of Form S5 comprises characteristic peaks at 2-theta angles of 5.42, 7.50, 10.82 and 16.91.

In one embodiment, the crystalline solvate form (Form S5) exhibits a TG-FTIR thermogram characterized by decomposition beginning at a temperature greater than 180° C.

In one embodiment, the crystalline solvate form (Form S8) exhibits an X-ray powder diffraction pattern as shown in FIG. 13, having characteristic peaks at 2-theta 4.7, 5.00, 5.38, 6.26, 9.66, 15.93, 21.05, 23.97, 24.69. In one embodiment, the powder X-ray diffraction pattern of Form S8 comprises characteristic peaks at 2-theta angles of 4.7, 5.00, 5.38, 6.26, 9.66 and 23.97. In one embodiment, the powder X-ray diffraction pattern of Form S8 comprises characteristic peaks at 2-theta angles of 4.7, 5.00, 9.66 and 23.97.

In one embodiment, the crystalline solvate form (Form S8) exhibits a TG-FTIR thermogram characterized by decomposition beginning at a temperature greater than 180° C.

In one embodiment, the crystalline solvate form (Form S1) exhibits an X-ray powder diffraction pattern having characteristic peaks at 2-theta 5.34, 7.48, 10.10, 10.68, 12.90, 16.07, 21.83, 23.09, 24.91, 26.93. In one embodiment, the powder X-ray diffraction pattern of Form S1 comprises characteristic peaks at 2-theta angles of 5.34, 7.48, and 10.68. In one embodiment, the powder X-ray diffraction pattern of Form S1 comprises characteristic peaks at 2-theta angles of 5.34, 7.48, 10.68 and 21.83. In one embodiment, the powder X-ray diffraction pattern of Form S1 comprises characteristic peaks at 2-theta angles of 5.34, 7.48, 10.68, 16.07 and 21.83.

In one embodiment, the crystalline solvate form (Form S1) exhibits a TG-FTIR thermogram characterized by decomposition beginning at a temperature greater than 200° C.

In some embodiments, the compound of Formula I is a mixture of crystalline forms of the compound of Formula I.

In some embodiments, the mixture is a mixture of one or more anhydrous crystalline forms.

In some embodiments, the mixture is a mixture of the crystalline Form I and the crystalline Form II. In some embodiments, the mixture is at least 25% the crystalline Form I. In some embodiments, the mixture is at least 50% the crystalline Form I. In some embodiments, the mixture is at least 75% the crystalline Form I.

In some embodiments, the mixture is a mixture of the crystalline Form I and the crystalline Hydrate form. In some embodiments, the mixture is at least 25% the crystalline Form I. In some embodiments, the mixture is at least 50% the crystalline Form I. In some embodiments, the mixture is at least 75% the crystalline Form I.

In some embodiments, the mixture is a mixture of the crystalline Form II and the crystalline Hydrate form. In some embodiments, the mixture is at least 25% the crystalline Form II. In some embodiments, the mixture is at least 50% the crystalline Form II. In some embodiments, the mixture is at least 75% the crystalline Form II.

(ii) Suitable Stabilizing Surfactants

In some embodiments, the composition comprises at least one stabilizing surfactant. In some embodiments, the composition comprises at least two stabilizing surfactants. In some embodiments, the composition comprises a stabilizing system.

In some embodiments, the composition comprises a non-ionic stabilizing surfactant. In some embodiments, the composition comprises an anionic stabilizing surfactant. In some embodiments, the composition comprises a combination of anon-ionic stabilizing surfactant and an anionic stabilizing surfactant.

In some embodiments, the suspension concentrate (SC) composition comprises at least one stabilizing surfactant. In some embodiments, the suspension concentrate (SC) composition comprises at least two stabilizing surfactants. In some embodiments, the suspension concentrate (SC) composition comprises two stabilizing surfactants.

In some embodiments, the composition is a suspoemulsion (SE) composition. In some embodiments, the SE composition comprises at least one stabilizing surfactant. In some embodiments, the SE composition comprises at least two stabilizing surfactants. In some embodiments, the SE composition comprises two stabilizing surfactants.

In some embodiments, the stabilizing surfactant is a physical stabilizer.

In some embodiments, the stabilizing surfactant affects the crystals growth rate of the compound of Formula I in the liquid carrier. In some embodiments, the stabilizing surfactant decreases the crystals growth rate of the compound of Formula I in the liquid carrier. In some embodiments, the stabilizing surfactant have a crystal growth inhibiting property. In some embodiments, the stabilizing surfactant is a crystal growth inhibitor.

In some embodiments, one of the stabilizing surfactants is a non-ionic stabilizing surfactant. In some embodiments, the non-ionic stabilizing surfactant is selected from the group consisting of polymers, ester alkoxylated amine, ester of alkoxylated diethylethanolamine, poly alkylene oxide alcohol ether, and alcohols.

In some embodiments, the polymer is a block polymer of random polymer. In some embodiments, the polymer is a tri-block polymer. In some embodiments, the tri-block polymer is an ABA block polymer. In some embodiments, the polymer has a low HLB (hydrophile-lpophile balance) value, preferably an HLB value of 5. In some embodiments, the polymer is Atlox™ 4912 (manufactured and sold by Croda).

In some embodiments, the non-ionic stabilizing surfactant is an ester alkoxylated amine. In some embodiments, the ester alkoxylated amine is Atlox™ 4915 (manufactured and sold by Croda). In some embodiments, the non-ionic stabilizing surfactant is Atlox™ 4915 (manufactured and sold by Croda). In some embodiments, the non-ionic stabilizing surfactant is alkoxylated diethylethanolamine. In some embodiments, the non-ionic stabilizing surfactant is di-ethyl ethanol amine mono-trimerate. In some embodiments, the non-ionic stabilizing surfactant is Atlox™ 4915 (manufactured and sold by Croda).

In some embodiments, the poly alkylene oxide alcohol ether is a fatty alcohol ether and/or a non-fatty alcohol ether.

In some embodiments, the non-ionic stabilizing surfactant is an alkoxylated fatty alcohol.

In some embodiments, the alkoxylated fatty alcohol is Genapol® X080 (manufactured and sold by Clariant), Genapol® X 050 (manufactured and sold by Clariant), tridecyl alcohol polyglycol ether, Rhodasurf® LA 30 (manufactured and sold by Solvay), Aerosol® OT-SE or Aerosol® OT-100 (manufactured and sold by Solvay), Rhodacal®70/B (manufactured and sold by Solvay), Arlatone™ TV (manufactured and sold by Croda). Alkamuls® A (manufactured and sold by Solvay), or Alkamuls® BR (manufactured and sold by Solvay).

In some embodiments, the alkoxylated fatty alcohol is Genapol® X080 (manufactured and sold by Clariant), Genapol® X 050 (manufactured and sold by Clariant), tridecyl alcohol polyglycol ether, or Rhodasurf® LA 30 (manufactured and sold by Solvay).

In some embodiments, the alkoxylated fatty alcohol is Atlas™ 5002L.

In some embodiments, the alcohol has a short carbon chain of C1-C6. In some embodiments, the alcohol has a long carbon chain of C7-C20.

In some embodiments, the non-ionic stabilizing surfactant is a non-ionic derivative of polyalkylene oxide polyaryl ether.

In some embodiments, one of the stabilizing surfactants is an ionic surfactant. In some embodiments, one of the stabilizing surfactants is an ionic stabilizing surfactant.

In some embodiments, the ionic stabilizing surfactant is selected from the group consisting of Aerosol® OT-SE or Aerosol® OT-100 (manufactured and sold by Solvay), Rhodacal® 70/B (manufactured and sold by Solvay), and a combination thereof.

In some embodiments, the ionic stabilizing surfactant is an anionic stabilizing surfactant. Anionic stabilizing surfactant refers to compounds which have an anionic group such as phosphonic salt and sulfonic salt. An example of an ionic surfactant that may be used is sodium dioctyl sulfosuccinate which is manufactured and sold by Solvay as Aerosol® OT-SE.

In some embodiments, the anionic stabilizing surfactant is anionic derivative of polyalkylene oxide polyaryl ether.

In some embodiments, the composition comprises at least one non-ionic stabilizing surfactant and at least one anionic stabilizing surfactant. In some embodiments, the stabilizing system comprises at least one non-ionic stabilizing surfactant and at least one anionic stabilizing surfactant.

In some embodiments, the composition comprising a non-ionic stabilizing surfactant and an anionic stabilizing surfactant is a SC composition. In some embodiments, the composition comprising a non-ionic stabilizing surfactant and an anionic stabilizing surfactant is a SE composition.

In some embodiments, one of the stabilizing surfactants is a derivative of polyalkylene oxide polyaryl ether. In some embodiments, the derivative of polyalkylene oxide polyaryl ether is a nonionic derivative of polyalkylene oxide polyaryl ether. In some embodiments, the derivative of polyalkylene oxide polyaryl ether surfactant is an anionic derivative of polyalkylene oxide polyaryl ether.

In some embodiments, the composition comprises at least two stabilizing surfactants. In some embodiments, the two stabilizing surfactants comprise two derivatives of polyalkylene oxide polyaryl ether. In some embodiments, the two stabilizing surfactants comprise a non-ionic derivative of polyalkylene oxide polyaryl ether and an anionic derivative of polyalkylene oxide polyaryl ether.

In some embodiments, the non-ionic derivative of polyalkylene oxide polyaryl ether is a compound having an aryl group substituted with at least two aromatic groups.

In some embodiments, the non-ionic derivative of polyalkylene oxide polyaryl ether has the following structure:

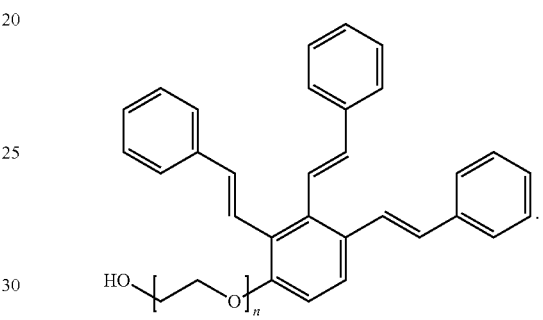

In some embodiments, the non-ionic derivative of polyalkylene oxide polyaryl ether has the following structure:

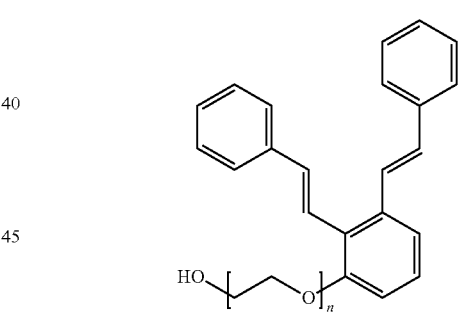

In some embodiments, the anionic derivative of polyalkylene oxide polyaryl ether is a compound having an aryl group substituted with at least two aromatic groups.

In some embodiments, the anionic derivative of polyalkylene oxide polyaryl ether comprises an anionic group selected from phosphate ($PO_4$), phosphonate ($PO_3$), sulfonate ($SO_3$), and sulfate ($SO_4$). In some embodiment, the anionic group of the anionic derivative of polyalkylene oxide polyaryl ether has an anionic group selected from phosphate ($PO_4$), phosphonate ($PO_3$), sulfonate ($SO_3$), and sulfate ($SO_4$).

In some embodiments, the polyalkylene oxide polyaryl ether comprises a polyalkylene oxide group selected from the group consisting of polyethylene oxide group, polypropylene oxide, polybutylene oxide and any combination thereof. In some embodiments, the polyalkylene oxide group is a polyethylene oxide. In some embodiments, the polyalkylene oxide group is a polypropylene oxide.

Polyalkylene oxides may include but are not limited to copolymers and homogenous polymers. Copolymers may include but are not limited to random polymer and block polymer. In some embodiments, the polyalkylene oxide group is a di block copolymer. In some embodiments, the polyalkylene oxide group is a tri block copolymer.

In some embodiments, the polyalkylene oxide polyaryl ether is a polyalkylene oxide styryl phenyl ether. In some embodiments, the polyalkylene oxide polyaryl ether is a polyalkylene oxide benzyl phenyl ether. In some embodiments, the polyalkylene oxide polyaryl ether is a polyalkylene oxide bisphenyl ether. In some embodiments, the polyalkylene oxide polyaryl ether is a polyalkylene oxide tristyryl phenyl ether. In some embodiments, the polyalkylene oxide polyaryl ether is a polyalkylene oxide distyryl phenyl ether. In some embodiments, the polyalkylene oxide distyryl phenyl ether is polyoxyethylene distyryl phenyl ether.

In some embodiments, the polyalkylene oxide polyaryl ether is an anionic stabilizing surfactant. Anionic stabilizing surfactant refers to compounds which have an anionic group such as phosphonic salt and sulfonic salt.

In some embodiments, the salt comprises a cation. In some embodiments, the cation is selected from a group consisting of sodium, potassium, ammonium, calcium, magnesium and combinations thereof.

In some embodiments, the anionic derivative of polyalkylene oxide polyaryl ether has the following structure:

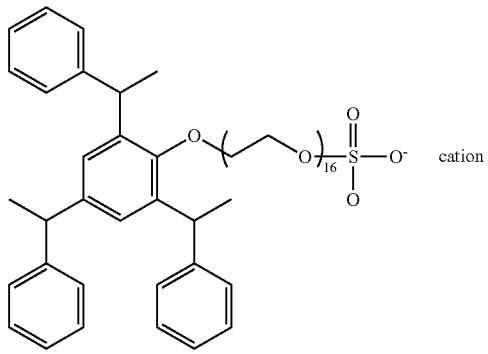

In some embodiments, the anionic derivative of polyalkylene oxide polyaryl ether is tristyrylphenol ethoxylate phosphate ester.

In some embodiments, the polyalkylene oxide polyaryl ether is tristyrylphenol ethoxylate phosphate ester. Preferably, the tristyrylphenol ethoxylate phosphate ester is Soprophor®, 3D33 manufactured and sold by Solvay.

In some embodiments, the polyalkylene oxide polyaryl ether is 2,4,6-Tri-(1-phenylethyl)-phenol polyglycol ether with 54 EO. Preferably, the 2,4,6-Tri-(1-phenylethyl)-phenol polyglycol ether with 54 EO is Emulsogen® TS 540 manufactured and sold by Clariant.

In some embodiments, the polyalkylene oxide polyaryl ether is ethoxylated tristyrylphenol. Preferably, the ethoxylated tristyrylphenol is Soprophor® TS/54 manufactured and sold by Solvay.

In some embodiments, the salt comprises at least one cation selected from group consisting of sodium, potassium, ammonium, calcium, magnesium and combination thereof.

Polyalkylene oxide polyaryl ether surfactants may include but is not limited to poly phenyl ethyl phenol and tristyrylphenol.

Polyalkylene oxide polyaryl ethers surfactant may include but is not limited to non-capped surfactants, end-capped surfactants or combination thereof.

In some embodiments, the composition comprises a combination of stabilizing surfactants and the combination of stabilizing surfactants comprises a mixture of a nonionic polyalkylene oxide polyaryl ether surfactant and an anionic polyalkylene oxide polyaryl ether surfactant. In some embodiments, the nonionic surfactant is tristyrylphenol ethoxylate. In some embodiments, the anionic surfactant is tristyrylphenol ethoxylate phosphate ether.

In some embodiments, the combination of stabilizing surfactants comprises tristyrylphenol ethoxylate and tristyrylphenol ethoxylate phosphate ether.

In some embodiments, the nonionic polyalkylene oxide polyaryl ether is a compound having an ether group substituted with at least two groups comprising aromatic rings.

In some embodiments, the polyalkylene oxide group is a polyoxyethylene. In some embodiments, the polyalkylene oxide group is a polyoxypropylene. In some embodiments, the polyalkylene oxide group is a block copolymer of polyoxyethylene. In some embodiments, the polyalkylene oxide group is a block copolymer of polyoxypropylene.

Polyalkylene oxides may include but are not limited to poly ethoxylated group, poly propoxylated group, poly butoxylated group and any combination thereof.

Polyalkylene oxides may include but are not limited to copolymers and homogenous polymers.

Copolymers may include but are not limited to random polymer and block polymer.

In some embodiments, the polyalkylene oxide polyaryl ether is a polyalkylene oxide tristyryl phenyl ether. In some embodiments the polyalkylene oxide tristyryl phenyl ether is polyoxyethylene tristyryl phenyl ether. In some embodiments, the polyalkylene oxide tristyryl phenyl ether is polyoxyethylene polyoxypropylene tristyryl phenyl ether.

In some embodiments, the polyalkylene oxide polyaryl ether is a polyalkylene oxide distyryl phenyl ether. In some embodiments, the polyalkylene oxide distyryl phenyl ether is polyoxyethylene distyryl phenyl ether.

In some embodiments, non-ionic derivative of a polyalkylene oxide polyaryl ether is tristyrylphenol ethoxylate phosphate ester.

In some embodiments, the stabilizing surfactant is a derivative of tristyryl phenol-polyethylene glycol ether.

In some embodiments, the stabilizing surfactant is an anionic derivative of tristyryl phenol-polyethylene glycol ether.

In some embodiments, the stabilizing surfactant is a non-ionic derivative of tristyryl phenol-polyethylene glycol ether.

In some embodiments, the composition comprises two stabilizing surfactants and the two stabilizing surfactants are Soprophor® 3D33 and Soprophor® TS/54 (TSP 54).

In some embodiments, the composition comprises two stabilizing surfactants and both stabilizing surfactants are derivatives of polyalkylene oxide polyaryl ether. In some embodiments, the composition comprises two stabilizing surfactants wherein one stabilizing surfactant is a non-ionic derivative of polyalkylene oxide polyaryl ether and one stabilizing surfactant is an anionic derivative of polyalkylene oxide polyaryl ether.

In some embodiments, the composition comprises at least two stabilizing surfactants wherein at least one stabilizing surfactant is a non-ionic derivative of polyalkylene oxide polyaryl ether and at least one stabilizing surfactant is an anionic derivative of polyalkylene oxide polyaryl ether.

In some embodiments, the SC composition comprises two stabilizing surfactants and the two stabilizing surfactants are Soprophor® 3D33 and Soprophor® TS/54 (TSP 54).

In some embodiments, the SC composition comprises two stabilizing surfactants and both stabilizing surfactants are derivatives of polyalkylene oxide polyaryl ether. In some embodiments, the composition comprises two stabilizing surfactants wherein one stabilizing surfactant is a non-ionic derivative of polyalkylene oxide polyaryl ether and one stabilizing surfactant is an anionic derivative of polyalkylene oxide polyaryl ether.

In some embodiments, the SC composition comprises at least two stabilizing surfactants wherein at least one stabilizing surfactant is a non-ionic derivative of polyalkylene oxide polyaryl ether and at least one stabilizing surfactant is an anionic derivative of polyalkylene oxide polyaryl ether.

In some embodiments, the SE composition comprises two stabilizing surfactants and the two stabilizing surfactants are Soprophor® 3D33 and Soprophor® TS/54 (TSP 54).

In some embodiments, the SE composition comprises two stabilizing surfactants and both stabilizing surfactants are derivatives of polyalkylene oxide polyaryl ether. In some embodiments, the composition comprises two stabilizing surfactants wherein one stabilizing surfactant is a non-ionic derivative of polyalkylene oxide polyaryl ether and one stabilizing surfactant is an anionic derivative of polyalkylene oxide polyaryl ether.

In some embodiments, the SE composition comprises at least two stabilizing surfactants wherein at least one stabilizing surfactant is a non-ionic derivative of polyalkylene oxide polyaryl ether and at least one stabilizing surfactant is an anionic derivative of polyalkylene oxide polyaryl ether.

In some embodiments, stabilizing surfactant is Soprophor® 3D33.

In some embodiments, stabilizing surfactant is tristyrylphenol ethoxylate phosphate ester.

In some embodiments, the polyalkylene oxide polyaryl ether is Soprophor® 3D 33 from Solvay.

In some embodiments, the polyalkylene oxide polyaryl ether is Emulsogen® TS 540 from Clariant.

In some embodiments, the polyalkylene oxide polyaryl ether is Soprophor®, TS/54 from Solvay.

In some embodiments, the salt comprising cation is selected from group consisting of sodium, potassium ammonium, calcium, magnesium and combination thereof.

Polyaryl may refer to but is not limited to poly phenyl ethyl phenol and tristyrylphenol.

Polyalkylene oxide polyaryl ethers surfactant refer to non-capped surfactants, end-capped surfactants or combination thereof.

In some embodiments, the combination of surfactants comprises a mixture of a nonionic polyalkylene oxide polyaryl ether surfactant and an anionic polyalkylene oxide polyaryl ether surfactant. In some embodiments, the non-ionic surfactant is tristyrylphenol ethoxylate. In some embodiments, the anionic surfactant is tristyrylphenol ethoxylate phosphate ether.

In some embodiments, the combination of surfactants comprises tristyrylphenol ethoxylate and tristyrylphenol ethoxylate phosphate ether.

In some embodiments, the nonionic polyalkylene oxide polyaryl ether is a compound having an ether group substituted with at least two groups comprising aromatic rings.

In some embodiments, the polyalkylene oxide group is a polyoxyethylene. In some embodiments, the polyalkylene oxide group is a polyoxypropylene. In some embodiments, the polyalkylene oxide group is a block copolymer of polyoxyethylene.

In some embodiments, the polyalkylene oxide group is a block copolymer of polyoxypropylene.

Polyalkylene oxides may include but are not limited to poly ethoxylated group, poly propoxylated group, poly butoxylated group and any combination thereof.

Polyalkylene oxides may include but ae not limited to copolymers and homogenous polymers.

Copolymers may include but are not limited to random polymer and block polymer.

In some embodiments, the polyalkylene oxide polyaryl ether is a polyalkylene oxide tristyryl phenyl ether. In some embodiments the polyalkylene oxide tristyryl phenyl ether is polyoxyethylene tristyryl phenyl ether. In some embodiments, the polyalkylene oxide tristyryl phenyl ether is polyoxyethylene polyoxypropylene tristyryl phenyl ether.

In some embodiments, the polyalkylene oxide polyaryl ether is a polyalkylene oxide distyryl phenyl ether. In some embodiments, the polyalkylene oxide distyryl phenyl ether is polyoxyethylene distyryl phenyl ether.

In some embodiments, nonionic derivative of a polyalkylene oxide polyaryl ether is tristyrylphenol ethoxylate phosphate ester In some embodiments, stabilizing surfactant is Emulsogen®, TS 540.

In some embodiments, nonionic derivative of surfactant is Emulsogen® TS 540.

In some embodiments, stabilizing surfactant is Soprophor® TS/54.

In some embodiments, nonionic derivative of a polyalkylene oxide polyaryl ether is Soprophor® TS/54.

In some embodiments, stabilizing surfactant is anionic derivative of tristyryl phenol-polyethylene glycol ether.

In some embodiments, stabilizing surfactant is nonionic derivative of tristyryl phenol-polyethylene glycol ether.

In some embodiments, the composition comprises a stabilizing system.

In some embodiments, the weight ratio of the non-ionic derivative of polyalkylene oxide polyaryl ether and the anionic derivative of polyalkylene oxide polyaryl ether is in the range of 0.25:1 to 1:1. In some embodiments, the weight ratio-of the non-ionic derivative of polyalkylene oxide polyaryl ether and the anionic derivative of polyalkylene oxide polyaryl ether is in the range of 0.25:1 to 0.5:1. In some embodiments, the weight ratio of the non-ionic derivative of polyalkylene oxide polyaryl ether and the anionic derivative of polyalkylene oxide polyaryl ether is about 0.36:1.

In some embodiments, the stable composition comprises at least 0.5% by weight based on the total weight of the composition of the polyalkylene oxide polyaryl ether stabilizing surfactant(s). In some embodiments, the stable composition comprises from 0.5% to 7% by weight based on the total weight of the composition of the polyalkylene oxide polyaryl ether stabilizing surfactant(s). In some embodiments, the stable composition comprises from 0.5% to 15% by weight based on the total weight of the composition of the polyalkylene oxide polyaryl ether stabilizing surfactant(s). In some embodiments, the stable composition comprises from 0.5% to 25% by weight based on the total weight of the composition of the polyalkylene oxide polyaryl ether stabilizing surfactant(s).

In some embodiments, the weight ratio of the compound of Formula I to the non-ionic derivative of polyalkylene oxide polyaryl ether is from 25:1 to 10:1. In some embodiments, the weight ratio of the compound of Formula I to the anionic derivative of polyalkylene oxide polyaryl ether is from 25:1 to 10:1.

In embodiments, the stabilizing surfactant(s) is effective for increasing stability of the compound of Formula I in the compositions described herein compared to liquid composition wherein the compound of Formula I is soluble. In some embodiments, the stability is chemical stability. In some embodiments, the stability is physical stability.

(iii) Suitable pH Adjusters

In some embodiments, the composition comprises a pH adjuster.

In some embodiments, the pH adjusters may include but are not limited to buffers, bases and/or acidifiers.

In some embodiments the pH adjuster is an acid. In some embodiments the pH adjuster is a base.

In some embodiments the pH adjuster is a mixture of at least one base and at least one acid.

In some embodiments the pH adjuster is a buffer.

Buffers refer to combinations of acids and bases. Acids include but are not limited to organic and inorganic acids. Bases include but are not limited to organic and inorganic bases.

Organic acids may include but are not limited to citric acid, formic acid, acetic acid, propionic acid, butyric acid, oxalic acid, lactic acid, malic acid, and benzoic acid.

Inorganic acids may include but are not limited to hydrochloric acid, nitric acid, phosphoric acid, sulfuric acid and boric acid.

Organic bases may include but are not limited to primary and secondary amines, pyridines, imidazole and any combination thereof.

In some embodiments, the pH adjuster is potassium hydrogen phosphate.

In some embodiments, the pH adjuster is combination of disodium mono hydrogen phosphate and potassium hydrogen phosphate.

In some embodiments, the stable liquid composition further comprises a buffer. In some embodiments, the amount of the buffer in the stable composition is 1 g/L to 20 g/L. In some embodiments, the stable liquid composition further comprises a buffer. In some embodiments, the amount of the buffer in the stable composition is 6 g/L to 15 g/L. In some embodiments, the stable liquid composition further comprises a buffer. In some embodiments, the amount of the buffer in the stable composition is 7 g/L to 10 g/L. In some embodiments, the concentration of the buffer in the stable composition is about 8.6 g/L.

In some embodiments the buffer is potassium dihydrogenorthophosphate. In some embodiments, the concentration of potassium dihydrogenorthophosphate in the stable liquid composition is 1 g/L to 5 g/L. In some embodiments, the concentration of potassium dihydrogenorthophosphate in the stable liquid composition is 1 g/L to 3 g/L. In some embodiments, the concentration of potassium dihydrogenorthophosphate in the stable liquid composition is about 1.7 g/L.

In some embodiments the buffer is disodium phosphate anhydrous. In some embodiments, the concentration of disodium phosphate anhydrous in the stable liquid composition is 1 g/L to 10 g/L. In some embodiments, the concentration of disodium phosphate anhydrous in the stable liquid composition is 5 g/L to 10 g/L. In some embodiments, the concentration of disodium phosphate anhydrous in the stable liquid composition is 5 g/L to 8 g/L. In some embodiments, the concentration of disodium phosphate anhydrous in the stable liquid composition is about 6.9 g/L.

(iv) Suitable Non-Aqueous Liquid Carriers

In some embodiments, the non-aqueous liquid carrier comprises one organic solvent.

In some embodiments, the non-aqueous liquid carrier comprises at least two organic solvents.

In some embodiments, the organic solvent is a non-aromatic solvent. In some embodiments, non-aromatic solvent is an aprotic solvent.

In some embodiments, organic solvent refers to co-solvent.

The solubility of the compound of Formula I in the solvent depends on the polarity of the solvent. In some embodiments, the polarity of the solvent between 25-50 (if water is 1M). Solvents (non-aqueous liquid carriers) can be combined if the polarity of the combination of solvents is between 25-50. In some embodiments, the solubility of water in the solvent less than 25 g/l. In some embodiments, the solvent has a dipole (D) at 20° C., of less than 10, preferably less than 5. In some embodiments, the solvent has a Log P value of higher than 1.

In some embodiments, the non-aqueous carrier is selected from a group consisting of aromatic hydrocarbons, paraffins, petroleum, diesel, mineral oil, ester and/or amide of fatty acids, tall oil fatty acids, and any combination thereof.

In some embodiments, the non-aqueous carrier is an aromatic hydrocarbon.

In some embodiments, the aromatic hydrocarbon is selected from a group consisting of toluene, o-xylene, m-xylene, p-xylene, ethylbenzene, isopropylbenzene, tert-butylbenzene, naphthalenes, and mono- or polyalkyl-substituted naphthalenes.

In some embodiments, the organic solvent is a paraffin.

In some embodiments, the non-aqueous liquid carrier is a vegetable oil. In some embodiments, the vegetable oil is selected from a group consisting of olive oil, kapok oil, castor oil, papaya oil, camellia oil, Canola oil, palm oil, sesame oil, corn oil, rice bran oil, peanut oil, cotton seed oil, soybean oil, rapeseed oil, linseed oil, tung oil, sunflower oil, safflower oil, and tall oil.

In some embodiments, the non-aqueous carrier is an ester of a fatty acid. In some embodiments, the alkyl ester of the fatty acid is C18 methyl canolate ester. In some embodiments, the C18 methyl canolate ester is Agnique® ME 18RD-F (manufactured and sold by BASF).

In some embodiments, the non-aqueous carrier is an amide of a fatty acid. In some embodiments, the amide of the fatty acid is selected from a group consisting of $C_1$-$C_3$ amines, alkylamines and alkanolamines with $C_6$-$C_{18}$ carboxylic acids.

In some embodiments, the non-aqueous carrier is an alkyl ester of a fatty acid. In some embodiments, the alkyl ester of the fatty acid is selected from a group consisting of $C_1$-$C_4$ monohydric alcohol esters of $C_8$ to $C_{22}$ fatty acids such as methyl oleate and ethyl oleate.

Other examples of non-aqueous carriers are methyl fatty acid ester, plant oil alkyl ester, xylene, octanol, acetophenone, cyclohexanone, Solvesso™ (manufactured and sold by ExxonMobil Chemical), N-methyl pyrrolidone, tributyl sulphate (TBP), ethyl hexyl lactate (EHL), alkyl (linear or cyclic) amide of fatty acid (natural or synthetic), aryl acetate (benzyl acetate), polyethylene carbonate, benzyl acetate, and propylene carbonate. In some embodiments, the non-aqueous carrier is cyclohexanone. In some embodiments, the non-aqueous carrier is acetophenone. In some embodiments, the non-aqueous carrier is benzyl acetate. In some embodiments, the non-aqueous carrier is propylene carbonate.

(v) Other Additives

Compositions of the present invention may further comprise one or more additional agriculturally acceptable inert additives, as known in the art, including but not limited to solid diluents, liquid diluents, wetting agents, adhesives, thickening agents, antifoaming agent, preservative, wetting agent, anti-oxidation agent, binders, fertilizers, or anti-freeze agents. In addition, the present composition may also further comprise additional crop protection agents known in the art, for example pesticides, safeners, agents for controlling phytopathogenic fungi or bacteria, and the like In some embodiments, the liquid stable liquid composition further comprises a rheology modifier. Rheology modifiers may be used to reduce phases separation, to increase the physical stability, and to increase the viscosity which affect the chemical stability.

In some embodiments, the rheology modifier is Bentone SD®-1 (modified bentonite) or Bentone SD®-3 (modified hectorite) (manufactured by Elementis). In some embodiments, the amount of Bentone SD®-1 or Bentone SD®-3 in the composition is between 0.5 to 1.0% by weight. In some embodiments, the rheology modifier is Attagel® 50 (manufactured by BASF) and Bentone SD®-1. In some embodiments, the amount of Attagel® 50 in the composition is 0.5% by weight and the amount of Bentone SDX-1 in the composition is 0.5% by weight. Use of Attagel® 50 (0.5% by weight based on the total weight of the composition) and Bentone SD®-1 (0.5% by weight based on the total weight of the composition) decreased degradation of the compound of Formula I from 7-8% to 4% after 8 weeks of storage at 40° C. The water concentration of the composition should be maintained at less than 0.5%, including when Bentone SD®-1 is used as rheology modifier.

In some embodiments, the rheology modifier is xanthan gum.

In some embodiments, the rheology modifier is a thickener.

In some embodiments, the thickener is a silica thickener.

In some embodiments, the thickener is selected from the group consisting of Aerosil® 200, Aerosil® R972, Aerosil® R202 and any combination thereof.

In some embodiments, the silica thickener is selected from the group consisting of Aerosil® R202, Aerosil® R812 and any combination thereof.

In some embodiments, the amount of Aerosil® R202 in the composition is between 1% to 5% by weight based on the total weight of the composition. In some embodiments, the amount of Aerosil® R202 in the composition is between 1.7% to 2.5% by weight based on the total weight of the composition.

In some embodiments, the amount of Aerosil® R812 in the composition is between 1% to 5% by weight based on the total weight of the composition. In some embodiments, the amount of Aerosil®, R812 in the composition is between 3.0% to 3.5% by weight based on the total weight of the composition.

In some embodiments, the amount of Bentone SD®-1 or Bentone SD®-3 in the composition is between 0.5 to 1.0% by weight based on the total weight of the composition.

In some embodiments, the concentration of rheology modifier in the stable liquid composition is 1 g/L to 150 g/L. In some embodiments, the concentration of rheology modifier in the stable liquid composition is 1 g/L to 5 g/L. In some embodiments, the concentration of rheology modifier in the stable liquid composition is 2.3 g/L. In some embodiments, the concentration of rheology modifier in the stable liquid composition is from 0.5 g/L to 130 g/L. In some embodiments, the concentration of rheology modifier in the stable liquid composition is 3 g/L.

In some embodiments, the composition further comprises at least one adjuvant. In some embodiments, the adjuvant is selected from the group consisting of:
  (i) polyalkylene oxide alkyl ether;
  (ii) siloxane polyalkyleneoxide copolymer;
  (iii) esters of fatty acid;
  (iv) vinylpyrrolidones and derivatives thereof; and
  (v) sugar-based surfactants.

Preferred adjuvants are described in more detail below.

In some embodiments, the present invention composition further comprises additionally acceptable inert additives. In some embodiments, the agriculturally acceptable inert additives refer but are not limited to anti-oxidation agents, de-foaming agents, dye, pigment, flavoring agent, dispersing agent, synergists, encapsulates, photo-stabilizer, Binder, sticker, water soluble fertilizers, repellents and sensitizers.

In some embodiments, the process further comprises adding least one dispersant.

In some embodiments, the stable liquid composition further comprises a dispersant agent. In some embodiments, the concentration of the dispersing agent in the stable liquid composition is from 1 g/L to 200 g/L.

In some embodiments, the stable liquid composition further comprises a wetting agent. In some embodiments, the wetting agent is sodium diisopropylnaphthalene sulphonate. In some embodiments, the concentration of the wetting agent in the stable composition is from 1 g/L to 10 g/L. In some embodiments, the concentration of the wetting agent in the stable composition is 5.5 g/L.

In some embodiments, the stable liquid composition further comprises a thickener agent. In some embodiments, the thickener agent is Xanthan gum. In some embodiments, the concentration of the thickener agent in the stable composition is from 0.25 g/L to 10 g/L. In some embodiments, the concentration of the thickener agent in the stable composition is 2 g/L.

In some embodiments, the stable liquid composition further comprises an anti-freeze agent. In some embodiments, the anti-freeze agent is 1,2-propanediol. In some embodiments, the concentration of anti-freeze agent in the stable composition is from 20 g/L to 70 g/L. In some embodiments, the concentration of antifreeze agent in the composition is 57.5 g/L.

In some embodiments, the stable liquid composition further comprises an antifoaming agent. In some embodiments, the concentration of antifoaming agent in the stable composition is from 1 g/L to 5 g/L. In some embodiments the concentration of antifoaming agent in the composition is 2 g/L.

In some embodiments, the stable liquid composition further comprises an anti-oxidation agents. Anti-oxidation agents include but are not limited to clay, BHA, BHT, TBH, Propyl gallate, Sodium thiosulphate, Tocopherol, Pyrogallol and Epichlorohydrin.

In some embodiments, the stable liquid composition further comprises a defoaming agent. Defoaming agents include but are not limited to organosilicones, EO/PO based defoamers, alkyl polyacrylates.

In some embodiments, the stable liquid composition further comprises a dyes. Dyes include but are not limited to acid dye, basic dye, natural dye, synthetic dye and azo dye.

In some embodiments, the stable liquid composition further comprises a wetting agent. Examples of a wetting agent include but are not limited to di alkyl naphthalene sulfonate, di alkyl sulfosuccinate, metal salt of alkyl ether sulfonate, alpha olefin sulfonate, N-acyl N-alkyl taurate, linear alkyl benzene sulfonates, carboxylates, sulphates, phosphate esters, polyoxyethylene surfactants, ethoxylated alkyl phenols, ethoxylated aliphatic alcohols, anhydrosorbitol esters and cetyltrimethylammonium bromide.

In some embodiments, the stable liquid composition further comprises a surfactant.

Surfactants may include but are not limited to alcohol polyglycol ether, alkyl-end-capped ethoxylate glycol, alkyl-end-capped alkyl block alkoxylate glycol, dialkyl sulfosuccinate, phosphated esters, alkyl sulfonates, alkyl aryl sulfonates, tristyrylphenol alkoxylates, natural or synthetic fatty acid alkoxylates, natural or synthetic fatty alcohols alkoxylates, alkoxylated alcohols (such as n-butyl alcohol poly glycol ether), block copolymers (such as ethylene oxide-propylene oxide block copolymers and ethylene oxide-butylene oxide block copolymers) or combinations thereof.

In some embodiments, the surfactant is an alkyl-end-capped alkoxylate. In some embodiments, the adjuvant is a methyl-end-capped ethoxylate. In some embodiments, the adjuvant is a methyl-end-capped tridecyl ethoxylate. In some embodiments, the adjuvant is a methyl-end-capped tridecyl ethoxylate with six ethylene oxides.

In some embodiments the surfactant is di isopropyl naphthalene sulfonate.

In some embodiments the composition disclosed herein may include additional pesticide.

The disclosed compositions may optionally include combinations that can comprise at least 1% by weight of one or more of the compositions with another pesticidal compound. Such additional pesticidal compounds may be fungicides, insecticides, nematocides, miticides, arthropodicides, bactericides or combinations thereof that are compatible with the synergistic compositions of the present disclosure in the medium selected for application, and not antagonistic to the activity of the present compounds. Accordingly, in such embodiments the other pesticidal compound of Formula I s employed as a supplemental toxicant for the same or for a different pesticidal use. The pesticidal compound and the synergistic composition can generally be mixed together in a weight ratio of from 1:100 to 100:1.

Mixtures Comprising Compound of Formula I and Adjuvant(s):

Adjuvants are inert chemicals which are added for increasing performance of the active ingredient and composition thereof. Enhancing the activity of the compound of Formula I is particularly challenging because many drawbacks were observed such as rapidly drifting, high surface tension of the drops on the leaf, which dramatically affected and limited penetration into the plant.

It was found that applying at least one of the selected adjuvants with the compound of Formula (I) enhances efficacy of the compound of Formula (I) in controlling fungal attack on a plant. The selected adjuvant(s) may be built-into the compositions comprising the compound for Formula I. The selected adjuvant(s) may also be added into a tank mix comprising the compound for Formula I. Additionally, if more than one adjuvant is used, one or more of the adjuvant(s) may be built-into the composition while other adjuvant(s) are added to the tank mix.

The present invention provides a fungicidal mixture comprising:
  (a) a fungicidally effective amount of a compound of Formula I:

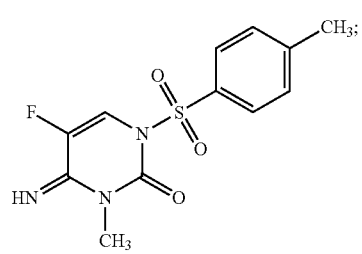

Formula I and
  (b) at least one adjuvant selected from the group consisting of:
    (i) polyalkylene oxide alkyl ether;
    (ii) siloxane polyalkyleneoxide copolymer;
    (iii) esters of fatty acid;
    (iv) vinylpyrrolidones and derivatives thereof; and
    (v) sugar-based surfactants.

In some embodiments, the fungicidal mixture is a composition. In some embodiments, the fungicidal mixture is a tank mix.

In some embodiments, the compound of Formula I is in a composition. In some embodiments, the compound of Formula I is in a stable, liquid composition. The stable, liquid composition of the compound of Formula I includes, but is not limited to, the stable, liquid compositions disclosed herein. In some embodiments, the stable, liquid composition is a suspension concentrate (SC) composition. In some embodiments, the stable, liquid composition is a suspoemulsion (SE) composition. In some embodiments, the stable, liquid composition is an oil dispersion (OD) composition. In some embodiments, the stable, liquid composition is an emulsifiable concentrate (EC) composition.

In some embodiments, the polyalkylene oxide alkyl ether is poly alkoxylated alcohol.

In some embodiments, the alkyl of the polyalkylene oxide alkyl ether comprises, but is not limited to, carbohydrate chain comprising C1-C26.

In some embodiments, the alcohol of the poly alkoxylated alcohol comprises, but is not limited to, carbohydrate chain of C1-C26.

In some embodiments, the alkyl of the polyalkylene oxide alkyl ethers comprises, but is not limited to, short carbohydrate chain and long carbohydrate chain.

Carbohydrate chains may refer, but are not limited, to saturated, unsaturated, branched and unbranched chains.

In some embodiments, short chain refers to C1-C8. In some embodiments, long chain refers to C9-C26.

In some embodiments, the polyalkylene oxide refers but is not limited to polyethylene oxide, polypropylene oxide, polybutylene oxide or combinations thereof.

In some embodiments, the polyalkylene oxide includes but is not limited to copolymers. Copolymer refers to block co-polymers, such as polyethylene oxide-polypropylene oxide, and/or random co-polymers, such as ethylene oxide-propylene oxide. In some embodiments, the polyalkylene oxide block copolymer is di block copolymer. In some embodiments, the polyalkylene oxide block copolymer is tri block copolymer.

In some embodiments, the tri block copolymer is polyethylene oxide/polypropylene oxide/polyethylene oxide.

In some embodiments, the polyalkylene oxide alkyl ether is alkyl end capped. In some embodiments, the alkyl includes but is not limited to short carbohydrate chain and long carbohydrate chain. Carbohydrate chains may refer but are not limited to saturated, unsaturated, branched and unbranched chains. In some embodiments, short chain refers to C1-C8.

In some embodiments, polyalkylene oxide alkyl ether is isotridecyl alcohol polyglycol ether.

In some embodiments, the polyalkylene oxide alkyl ether is C16-C18 alcohol ethoxylate propoxylate ether.

In some embodiments, the C16-C18 alcohol ethoxylate propoxylate ether is Ethylan™ 995 manufactured and sold by Akzo Nobel Agrochemicals. In some embodiments, the C16-C18 alcohol ethoxylate propoxylate ether is Agnique® BP420 manufactured and sold by BASF.

In some embodiments, the polyalkylene oxide alkyl ether is ethoxylate propoxylate alcohol.

In some embodiments, the ethoxylate propoxylate alcohol is Synperonic™ 13/9 manufactured and sold by Croda. In some embodiments, the ethoxylate propoxylate alcohol is Atplus™ PFA manufactured and sold by Croda.

In some embodiments, the polyalkylene oxide alkyl ether is iso-tridecyl alcohol polyglycol ether.

In some embodiments, the iso-tridecyl alcohol polyglycol ether is Genapol® X80 manufactured and sold by Clariant. In some embodiments, the iso-tridecyl alcohol polyglycol ether is Trycol® manufactured and sold by BASF.

In some embodiments, the polyalkylene oxide alkyl ether is effective for reducing surface tension of the composition and improving spreading of the compound of Formula I on plant leaf. Reducing the surface tension leads to reduced drifting from the leaf.

In some embodiments, the siloxane polyalkylene oxide copolymer refers to organo modified trisiloxane.

In some embodiments, the siloxane polyalkylene oxide copolymer is Break-Thru® S233 from Evonik. In some embodiments, the siloxane polyalkylene oxide copolymer is Silwett® 077 from Momentive.

In some embodiments, the siloxane polyalkylene oxide copolymer is effective for reducing surface tension of the composition. Silicone surfactant was found efficient agent for reducing surface tension and rapidly spread on of the composition over lipophilic surfaces.

In some embodiments, the ester of fatty acid may include but is not limited to alkyl ester of fatty acid and plant oil.

In some embodiments, the alky ester comprising carbohydrate chain comprising C10-C20.

In some embodiments, the alkyl includes but is not limited to short carbohydrate chain Carbohydrate chains may refer but are not limited to saturated, unsaturated, branched and unbranched chains.

In some embodiments, short chain refers to C1-C8. In some embodiments, fatty acid alkyl ester is Rhodaphac® PA/23 from Solvay (phosphate ester of ethoxylated fatty alcohol) or Alkamuls® VO/2003 (ethoxylated (18EO) fatty acid) from Solvay.

In some embodiments, the adjuvant is tridecyl alcohol ethoxylated or polyoxyethylene (9) isotridecanol.

In some embodiments, plant oil includes but is not limited to vegetable oil and derivatives thereof.

In some embodiments, vegetable oil includes but is not limited to seed oil, coconut oil, rape seed oil, castor oil, soybean oil, palm oil and corn oil.

In some embodiments, derivative of vegetable oil refers to alkyl ester, poly alkylene oxide.

Polyalkylene oxide refers to polyethylene oxide, polypropylene oxide, polybutylene oxide and combination thereof.

In some embodiments, vegetable oil and derivatives thereof include but is not limited to rapeseed oil methylated ester and coconut fatty acid ester of polyglycerol ether.

In some embodiments, the adjuvant is a mixture of methylated seed oil and polyglycerol ester.

In some embodiments, the rapeseed oil methylated ester is Agnique® ME 18 RDF manufactured and sold by BASF.

In some embodiments, the polyalkylene oxide derivative of vegetable oil is coconut fatty acid ester of polyglycerol ether.

In some embodiments, the coconut fatty acid ester of polyglycerol ether is Synergen® GL5 manufactured and sold by Clariant.

In some embodiments, the ester of fatty acid soften the leafs surface properties for better and efficient penetration of the compound of Formula I.

In some embodiments, the derivative of vinylpyrrolidones is a block copolymer of vinylpyrrolidone and vinyl acetate (VP/VA).

In some embodiments, the block copolymer of vinylpyrrolidone and vinyl acetate is Sokalan® VA 64 P manufactured and sold by Ashland.

In some embodiments, the block copolymer of vinylpyrrolidone and vinyl acetate is Agrimer™ VA 6 manufactured and sold by Ashland.

In some embodiments, the vinylpyrrolidones (PVP) and derivatives thereof are effective for increasing adherence of the compound of Formula I to plant leaves, for improvement of adhesive and retention properties (e.g, for rain fastness).

Sugar-based surfactants may include but are not limited to sorbitan esters, sucrose esters, alkyl polyglycosides, and fatty acid glucamides.

In some embodiments, the sugar-based surfactant is alkyl or fatty acid derivative of lglucamides.

In some embodiments, the sugar-based surfactant is alkylglucamides.

In some embodiments, the fatty acid glucamide is C8/C10 fatty acid glucose amide.

In some embodiments, the C8/C10 fatty acid glucose amide is Synergen® GA from Clariant.

In some embodiments, the sugar-based surfactant is sorbitan and derivatives thereof.

In some embodiments, the derivative of sorbitan is poly ethylene oxide derivative and fatty acid ester.

In some embodiments, the sorbitan is di or tri fatty acid ester. In some embodiments, the derivative of sorbitan is poly ethylene oxide derivative comprising 20 to 80 groups of ethylene oxide.

In some embodiments, the derivative of sorbitan is Tween® 80.

In some embodiments, the sugar-based surfactant affects the leaf surface for improving the penetration of the compound of Formula I through the leaf surface.

In some embodiments, the fungicidal mixture comprises a multi adjuvants system. Multi adjuvants system refers to blend or any combination of adjuvants.

In some embodiments, the fungicidal mixture comprises at least two adjuvants. In some embodiments, the fungicidal mixture comprises at least three adjuvants.

In some embodiments, the adjuvants affect the penetration in different manner. In some embodiments, the adjuvants affect the penetration in the same manner.

In some embodiments, blend of adjuvant includes but is not limited to combination of alkyl fatty acid ester and fatty alcohol alkoxylate.

In some embodiments, the combination of alkyl fatty acid ester and fatty alcohol alkoxylate is Synergen® SOC manufactured and sold by Clariant.

In some embodiments, the combination of alkyl fatty acid ester and fatty alcohol alkoxylate is FOP manufactured and sold by Clariant.

In some embodiments, a blend of adjuvant includes but is not limited to combination of plant oil and/or derivative thereof and sugar-based surfactant.

In some embodiments, the amount of compound (I) in the mixture is between 1-99.99% by weight.

In some embodiments, the amount of the adjuvant(s) in the mixture is between 0.01-95% by weight.

In some embodiments, the range of weight ratio of the compound of Formula I to the adjuvant(s) is 50:1 to 1:50. In some embodiments, the range of the weight ratio of the compound of Formula I to the adjuvant(s) is 10:1 to 1:10. In some embodiments, the range of the weight ratio of the compound of Formula I to the adjuvant(s) is 5:1 to 1:5. In some embodiments, the weight ratio of the compound of Formula I to the adjuvant(s) is 1:1.

In some embodiments, the range of the volume ratio of the compound of Formula I to the adjuvant(s) is 50:1 to 1:50. In some embodiments, the range of the volume ratio of the compound of Formula I to the adjuvant(s) is 10:1 to 1:10. In some embodiments, the range of the volume ratio of the compound of Formula I to the adjuvant(s) is 5:1 to 1:5. In some embodiments, the volume ratio of the compound of Formula I to the adjuvant(s) is 1:1.

In some embodiments, the weight ratio of the compound of Formula I to the adjuvant having the vinylpyrrolidones and derivative thereof structure is 25:1.

In some embodiments, the weight ratio of the compound of Formula I to the adjuvant having the siloxane polyalkyleneoxide copolymer structure is 50:1.

In one embodiment, the weight ratio between the polyalkylene oxide alkyl ether and compound of Formula I in the mixture is 1:90.

In one embodiment, the weight ratio between the plant oils and derivatives thereof and compound of Formula I in the mixture is 1:90.

In one embodiment, the weight ratio between the vinylpyrrolidones and derivative thereof and compound of Formula I in the mixture is 1:90.

In one embodiment, the weight ratio between the sugar-based surfactants and compound of Formula I in the mixture is 1:90.

In some embodiments, the range of the weight ratio between the two adjuvants is 5:1 to 1:5. In some embodiments, the weight ratio of between the two adjuvants is 2:1 to 1:2. In some embodiments, the weight ratio of between the two adjuvants is 1:1.

In some embodiments, the range of the weight ratio between the adjuvant having the vinylpyrrolidones and derivative thereof structure to the adjuvant having the siloxane polyalkyleneoxide copolymer structure is 5:1 to 1:5, In some embodiments, the weight ratio between the adjuvant having the vinylpyrrolidones and derivative thereof structure to the adjuvant having the siloxane polyalkyleneoxide copolymer structure is 2:1. In some embodiments, the weight ratio between the adjuvant having the vinylpyrrolidones and derivative thereof structure to the adjuvant having the siloxane polyalkyleneoxide copolymer structure is 1.4:1.

In some embodiments, the range of the weight ratio between the adjuvant having the vinylpyrrolidones and derivative thereof structure to the adjuvant having the polyalkylene oxide alkyl ether structure is 10:1 to 1:10. In some embodiments, the weight ratio between the adjuvant having the vinylpyrrolidones and derivative thereof structure to the adjuvant having the polyalkylene oxide alkyl ether structure is 1:5.5.

In some embodiments, the range of the weight ratio between the adjuvant having the vinylpyrrolidones and derivative thereof structure to the adjuvant having the ester of fatty acid structure is 5:1 to 1:5. In some embodiments, the weight ratio between the adjuvant having the vinylpyrrolidones and derivative thereof structure to the adjuvant having the ester of fatty acid structure is 1:3.7.

In some embodiments, the range of the weight ratio between the adjuvant having the polyalkylene oxide alkyl ether structure to the adjuvant having the ester of fatty acid structure is 5:1 to 1:5. In some embodiments, the range of the weight ratio between the adjuvant having the polyalkylene oxide alkyl ether structure to the adjuvant having the ester of fatty acid structure is 1.5:1.

In some embodiments, the range of the weight ratio between the adjuvant having the polyalkylene oxide alkyl ether structure to the adjuvant having the ester of fatty acid to the adjuvant having the vinylpyrrolidones and derivative thereof structure is 10:5:1 to 1:5:10. In some embodiments, the range of the weight ratio between the adjuvant having the polyalkylene oxide alkyl ether structure to the adjuvant having the ester of fatty acid to the adjuvant having the vinylpyrrolidones and derivative thereof structure is 5.7:3.76:1.

In some embodiments, the weight ratio range of the two adjuvants in the multi adjuvants system is between 5:1 to 1:5, or 1:3 to 3:1, or 1:2 to 2:1 or 1:1.

In some embodiments, the weight ratio of the compound of Formula I and the adjuvant(s) is 5:1 to 1:5, or 1:3 to 3:1, or 1:2 to 2:1 or 1:1.

In some embodiments, the weight ratio of the compound of Formula I and the adjuvant(s) in the mixture is 5:1 to 1:5, or 1:3 to 3:1, or 1:2 to 2:1 or 1:1.

In some embodiments, in built-in the adjuvant is present in an amount of at least 0.1% by weight based on the total weight of the composition. In some embodiments, the adjuvant is present in an amount of at least 10% by weight based on the total weight of the composition. In some embodiments, the adjuvant is present in an amount of at least 15% by weight based on the total weight of the composition. In some embodiments, the adjuvant is present in an amount of up to 30% by weight based on the total weight of the composition.

In some embodiments, the mixture of the present invention formulated as one composition, called built-in composition. In some embodiments, the mixture is formulated into two separate compositions and the composition are added in tank mix.

In some embodiments the ratio of adjuvant to compound (I) in tank mix is from 50:1 to 1:50.

In some embodiments, the range of the volume ratio of the compound of formula I to the adjuvant(s) is 50:1 to 1:50. In some embodiments, the range of the volume ratio of the compound of formula I to the adjuvant(s) is 10:1 to 1:10. In some embodiments, the range of the volume ratio of the compound of formula I to the adjuvant(s) is 5:1 to 1:5.

In some embodiments, the volume ratio of the compound of formula I to the adjuvant(s) is 1:1.

In some embodiments, the concentration of the adjuvant having the structure of polyalkylene oxide alkyl ether in the composition/mixture is at least 3% by weight based on the total weight of the composition.

In some embodiments, the concentration of the adjuvant having the structure of siloxane polyalkyleneoxide copolymer in the composition/mixture is at least 5% by weight based on the total weight of the composition.

In some embodiments, the concentration of the adjuvant having the structure of ester of fatty acid in the composition/mixture is at least 3% by weight based on the total weight of the composition.

In some embodiments, the concentration of the adjuvant having the structure of vinylpyrrolidones and derivative thereof in the composition/mixture is between 0.1% to 2.5% by weight based on the total weight of the composition.

In some embodiments, the concentration of the adjuvant having the structure of sugar-based surfactant in the composition/mixture is at least 3% by weight based on the total weight of the composition.

In some embodiments, when a polyalkylene oxide alkyl ether concentration in the composition is less than 3% by weight based on the total weight of the composition, the polyalkylene oxide alkyl ether is used as the surfactant/emulsifier.

In this connection, when a siloxane polyalkyleneoxide copolymer concentration in the composition less than 5% by weight based on the total weight of the composition, the siloxane polyalkyleneoxide copolymer is used as the surfactant/emulsifier.

In this connection, when an ester of fatty acid concentration in the composition is less than 3% by weight based on the total weight of the composition, the ester of fatty acid is used as the surfactant/emulsifier.

In this connection, when a sugar-based surfactant concentration in the composition less than 3% by weight based on the total weight of the composition, the sugar-based surfactant is used as the surfactant/emulsifier.

In some embodiment the compositions of compound (I) and/or adjuvant are liquid compositions, solid composition or combination thereof.

Example for liquid composition is a suspension concentration (SC) composition, an oil dispersion (OD) composition or an emulsifiable concentrate (EC) composition.

In one embodiment, the amount of polyalkylene oxide alkyl ether in the mixture of compound of Formula I with adjuvant(s) or in composition, ranges from about 1% to about 5% by weight based on the total weight of the composition.

In one embodiment, the amount of siloxane polyalkyleneoxide copolymer in the mixture of compound of Formula I with adjuvant(s) or in composition, ranges from about 1% to about 5% by weight based on the total weight of the composition.

In one embodiment, the amount of fatty acid alkyl esters in the mixture of compound of Formula I with adjuvant(s) or in composition, ranges from about 1% to about 5% by weight based on the total weight of the composition.

In one embodiment, the amount of plant oils and derivatives thereof in the mixture of compound of Formula I with adjuvant(s) or in composition, ranges from about 1% to about 5% by weight based on the total weight of the composition.

In one embodiment, the amount of vinylpyrrolidones and derivative thereof in the mixture of compound of Formula I with adjuvant(s) or in composition, ranges from about 1% to about 5% by weight based on the total weight of the composition.

In one embodiment, the amount of sugar-based surfactants in the mixture of compound of Formula I with adjuvant(s) or in composition, ranges from about 1% to about 5% by weight based on the total weight of the composition.

In one embodiment, the amount of polyalkylene oxide alkyl ether in the mixture of compound of Formula I with adjuvant(s) or in composition, ranges from about 1% to about 5% by weight based on the total weight of the composition.

In one embodiment, the amount of siloxane polyalkyleneoxide copolymer in the mixture of compound of Formula I with adjuvant(s) or in composition, ranges from about 1% to about 5% by weight based on the total weight of the composition.

In one embodiment, the amount of fatty acid alkyl esters in the mixture of compound of Formula I with adjuvant(s) or in composition, ranges from about 1% to about 5% by weight based on the total weight of the composition.

In one embodiment, the amount of plant oils and derivatives thereof in the mixture of compound of Formula I with adjuvant(s) or in composition, ranges from about 1% to about 5% by weight based on the total weight of the composition.

In one embodiment, the amount of vinylpyrrolidones and derivative thereof in the mixture of compound of Formula I with adjuvant(s) or in composition, ranges from about 1% to about 5% by weight based on the total weight of the composition.

In one embodiment, the amount of sugar-based surfactants in the mixture of compound of Formula I with adjuvant(s) or in composition, ranges from about 1% to about 5% by weight based on the total weight of the composition.

In one embodiment, the concentration of polyalkylene oxide alkyl ether in composition comprising compound of Formula I is 5% by weight based on the total weight of the composition.

In one embodiment, the concentration of siloxane polyalkyleneoxide copolymer in composition comprising compound of Formula I is 0.1% by weight based on the total weight of the composition.

In one embodiment, the concentration of fatty acid alkyl esters in composition of compound of Formula I is 5% by weight based on the total weight of the composition.

In one embodiment, the concentration of plant oils and derivatives thereof in composition comprising compound of Formula I is 6% by weight based on the total weight of the composition.

In one embodiment, the concentration of vinylpyrrolidones and derivative thereof in composition comprising compound of Formula I is 1.5% by weight based on the total weight of the composition.

In one embodiment, the concentration of sugar-based surfactant in composition comprising compound of Formula I is 5% by weight based on the total weight of the composition.

In one embodiment, the amount of polyalkylene oxide alkyl ether in the mixture of compound of Formula I with adjuvant(s) or in composition, ranges from about 1% to about 5% by weight based on the total weight of the composition In one embodiment, the amount of siloxane polyalkyleneoxide copolymer in the mixture of compound of Formula I with adjuvant(s) or in composition, ranges from about 1% to about 5% by weight based on the total weight of the composition In one embodiment, the amount of fatty acid alkyl esters in the mixture of compound of Formula I with adjuvant(s) or in composition, ranges from about 1% to about 5% by weight based on the total weight of the composition In one embodiment, the amount of plant oils and derivatives thereof in the mixture of compound of Formula I with adjuvant(s) or in composition, ranges from about 1% to about 5% by weight based on the total weight of the composition In one embodiment, the amount of vinylpyrrolidones and derivative thereof in the mixture of compound of Formula I with adjuvant(s) or in composition, ranges from about 1% to about 5% by weight based on the total weight of the composition In one embodiment, the amount of sugar-based surfactants in the mixture of compound of Formula I with adjuvant (s) or in composition, ranges from about 1% to about 5% by weight based on the total weight of the composition In some embodiments, the concentration of VP/VA in the composition is about 1-3% by weight based on the total weight of the composition. In some embodiments, the concentration of VP/VA in the composition is about 1.5% by weight based on the total weight of the composition.

In some embodiments, the concentration of PVP in the composition is about 0.5-1.5% % by weight based on the total weight of the composition. In some embodiments, the concentration of PVP in the composition is about 0.75-1.25% by weight based on the total weight of the composition.

In some embodiments, the concentration of siloxane polyalkyleneoxide copolymer in the composition is about 0.25-2.5% by weight based on the total weight of the composition. In some embodiments, the concentration of VP/VA in is about 0.1-2.0% by weight based on the total weight of the composition.

In some embodiments, the adjuvants in the multi adjuvant system have similar properties.

In some embodiments, the adjuvants in the multi adjuvant system have different properties.

In some embodiments, the adjuvant affects the leafs surface properties.

In some embodiments, the adjuvant affects the composition's physical properties.

In some embodiments, one adjuvant or multi adjuvant system/blend affect the surface tension of the drop/composition/composition after dilution; acts as a sticking agent; improve the spreading of the compound of Formula I on the leaf.

In some embodiment, the penetration of compound of Formula I is increased by reducing the surface tension of the composition, thus spreads the formulation on the leafs surface and enhances penetration.

In some embodiments, the adjuvant is used also as solvent, surfactant, wetting agent, dispersant and/or surfactant.

In some embodiments, the composition solvent, surfactant, wetting agent, dispersant and/or surfactant is used also as adjuvant.

In some embodiments, Agnique® ME 18 RD-F (fatty acids, C16-18 and C18-unsaturated, methyl esters) is a solvent and a built-in adjuvant.

In some embodiments. Genapol® x80 (isotridecyl alcohol polyglycol ether nonionic surfactant) is an emulsifier/surfactant and a built in adjuvant.

In some embodiments, Agnique® ME 18 RD-F (fatty acids, C16-18 and C18-unsaturated, methyl esters) is a solvent and a built-in adjuvant in an OD composition.

In some embodiments, Genapol® x80 (isotridecyl alcohol polyglycol ether nonionic surfactant) is an emulsifier/surfactant and a built-in adjuvant in an OD composition.

In some embodiments, solvent Agnique® ME 18 RD-F (fatty acids, C16-18 and C18-unsaturated, methyl esters) is also a built-in adjuvant.

In some embodiments, emulsifier/surfactant Genapol®: x80 (isotridecyl alcohol polyglycol ether nonionic surfactant) is also a built-in adjuvant.

In some embodiments, solvent Agnique® ME 18 RD-F (Fatty acids, C16-18 and C18-unsaturated, methyl esters) in an OD composition is also a built-in adjuvant.

In some embodiments, emulsifier/surfactant Genapol® x80 (isotridecyl alcohol polyglycol ether nonionic surfactant) in an OD composition is also a built-in adjuvant.

The compositions are prepared according to procedures which are conventional in the agricultural chemical art, but which are novel and important because of the presence therein of the disclosed mixture of compound (I) and adjuvant.

Concentrated compositions of the disclosed mixture can be dispersed in water, or another liquid, for application, or compositions can be dust-like or granular, which can then be applied without further treatment or can be dilute before application.

The compositions that are applied most often are aqueous suspensions or emulsions. Either such water-soluble, water-suspendable, or emulsifiable compositions are solids, usually known as wettable powders, or liquids, usually known as emulsifiable concentrates, aqueous suspensions, suspension concentrates or suspoemulsions. The present disclosure contemplates all vehicles by which the mixture can be formulated for delivery and use as a fungicide.

Additional Agrochemicals:

The mixtures and compositions of the present invention may further comprise one or more additional agrochemicals.

In some embodiments, the composition of the present invention further comprises at least one additional pesticide. In some embodiments, the pesticide is a fungicide, herbicide, insecticide, or nematicide.

In some embodiments, the composition of the present invention further comprises at least one additional fungicide. In some embodiments, the fungicidal mixture of the present invention further comprises at least one additional fungicide.

In some embodiments, the at least one additional fungicide is a fungicidal sterol biosynthesis inhibitor.

In some embodiments, the sterol biosynthesis inhibitor is selected from the group consisting of prothioconazole, epoxiconazole, cyproconazole, myclobutanil, prochloraz, metconazole, difenoconazole, tebuconazole, tetraconazole, fenbuconazole, propiconazole, fluquinconazole, flusilazole, flutriafol, and fenpropimorph.

In some embodiments, the sterol biosynthesis inhibitor is selected from the group consisting of prothioconazole, epoxiconazole, metconazole, difenoconazole, propiconazole, prochloraz, tetraconazole, tebuconazole, fenpropimorph, fenpropidin, ipconazole, triticonazole, spiroxamine, fenhexamid, and fenpyrazamine.

In some embodiments, the sterol biosynthesis inhibitor is prothioconazole. In some embodiments, the sterol biosynthesis inhibitor is epoxiconazole. In some embodiments, the sterol biosynthesis inhibitor is cyproconazole. In some embodiments, the sterol biosynthesis inhibitor is myclobutanil. In some embodiments, the sterol biosynthesis inhibitor is metconazole. In some embodiments, the sterol biosynthesis inhibitor is difenoconazole. In some embodiments, the sterol biosynthesis inhibitor is propiconazole. In some embodiments, the sterol biosynthesis inhibitor is prochloraz. In some embodiments, the sterol biosynthesis inhibitor is tetraconazole. In some embodiments, the sterol biosynthesis inhibitor is tebuconazole. In some embodiments, the sterol biosynthesis inhibitor is fluquinconazole. In some embodiments, the sterol biosynthesis inhibitor is flusilazole. In some embodiments, the sterol biosynthesis inhibitor is flutriafol. In some embodiments, the sterol biosynthesis inhibitor is fenpropimorph. In some embodiments, the sterol biosynthesis inhibitor is fenpropidin. In some embodiments, the sterol biosynthesis inhibitor is ipconazole. In some embodiments, the sterol biosynthesis inhibitor is triticonazole. In some embodiments, the sterol biosynthesis inhibitor is spiroxamin. In some embodiments, the sterol biosynthesis inhibitor is fenhexamid. In some embodiments, the sterol biosynthesis inhibitor is fenpyrazamine. In some embodiments, the sterol biosynthesis inhibitor is fenbuconazole.

In some embodiments, the at least one additional fungicide is a succinate dehydrogenase inhibitor.

In some embodiments, the succinate dehydrogenase inhibitor is selected from the group consisting of benzovindiflupyr, penthiopyrad, isopyrazam, fluxapyroxad, boscalid, fluopyram, bixafen, and penflufen.

In some embodiments, the succinate dehydrogenase inhibitor is benzovindiflupyr. In some embodiments, the succinate dehydrogenase inhibitor is penthiopyrad. In some embodiments, the succinate dehydrogenase inhibitor is isopyrazam. In some embodiments, the succinate dehydrogenase inhibitor is fluxapyroxad. In some embodiments, the succinate dehydrogenase inhibitor is boscalid. In some embodiments, the succinate dehydrogenase inhibitor is fluopyram. In some embodiments, the succinate dehydrogenase inhibitor is bixafen. In some embodiments, the succinate dehydrogenase inhibitor is penflufen.

In some embodiments, the at least one additional fungicide is a strobilurin fungicide.

In some embodiments, the strobilurin fungicide is selected from the group consisting of azoxystrobin, pyraclostrobin, picoxystrobin, fluoxastrobin, trifloxystrobin, kresoxim-methyl, dimoxystrobin, and orysastrobin.

In some embodiments, the strobilurin fungicide is selected from the group consisting of azoxystrobin, pyraclostrobin, picoxystrobin, fluoxastrobin, and trifloxystrobin.

In some embodiments, the strobilurin fungicide is azoxystrobin. In some embodiments, the strobilurin fungicide is pyraclostrobin. In some embodiments, the strobilurin fungicide is picoxystrobin. In some embodiments, the strobilurin fungicide is fluoxastrobin. In some embodiments, the strobilurin fungicide is trifloxystrobin. In some embodiments, the strobilurin fungicide is kresoxim-methyl. In some embodiments, the strobilurin fungicide is dimoxystrobin. In some embodiments, the strobilurin fungicide is orysastrobin.

In some embodiments, the at least one additional fungicide is a fungicidal multisite inhibitor.

In some embodiments, the fungicidal multisite inhibitor is selected from a group consisting of mancozeb, chlorothalonil, folpet, captan, metiram, maneb, propineb, copper hydroxide, copper octanoate, copper oxychloride, copper sulfate, copper sulfate (tribasic), mancopper, oxine-copper, copper bis(3-phenylsalicylate), copper zinc chromate, cuprous oxide, cupric hydrazinium sulfate, and cuprobam.

In some embodiments, the fungicidal multisite inhibitor is mancozeb. In some embodiments, the fungicidal multisite inhibitor is chlorothalonil. In some embodiments, the fungicidal multisite inhibitor is folpet. In some embodiments, the fungicidal multisite inhibitor is captan. In some embodiments, the fungicidal multisite inhibitor is metiram. In some embodiments, the fungicidal multisite inhibitor is maneb. In some embodiments, the fungicidal multisite inhibitor is propineb. In some embodiments, the fungicidal multisite inhibitor is copper hydroxide, copper octanoate, copper oxychloride, copper sulfate, copper sulfate (tribasic), mancopper, oxine-copper, copper bis(3-phenylsalicylate), copper zinc chromate, cuprous oxide, cupric hydrazinium sulfate, or cuprobam.

In some embodiments, the additional fungicide is selected from the group consisting of 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminum, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxium-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraowstrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp. *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxvethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril, benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate. Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate). OCH, phenylmercury dimethyldithiocarbamate, phenylmercury nitrate, phosdiphen, prothiocarb, prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Synergistic compositions comprising the compound of Formula I, and uses thereof, are described in U.S. Pat. No. 9,526,245 (issued Dec. 27, 2016), U.S. Pat. No. 10,045,533 (issued Aug. 14, 2018), U.S. Pat. No. 9,532,570 (issued Jan. 3, 2017), U.S. Pat. No. 10,045,534 (issued Aug. 14, 2018), U.S. Pat. No. 9,538,753 (issued Jan. 10, 2017), and U.S. Pat. No. 10,051,862 (issued Aug. 21, 2018), the entire content of each of which is hereby incorporated by reference.

In some embodiments, the composition of the present invention further comprises at least one plant health stimulator. In some embodiments, the fungicidal mixture of the present invention further comprises at least one plant health stimulator.

In some embodiments, the plant health stimulator is selected from the group consisting of organic compounds, inorganic fertilizers or micronutrient donors, biocontrol agents and inoculants.

Uses and Applications of the Compositions Described Herein:

The present invention also provides a method for the control and/or prevention of fungal pathogen attack on a plant comprising applying any one of the compositions or mixtures described herein to soil, plant, root, foliage, seed, locus of the fungus, and/or a locus in which the infestation is to be prevented so as to thereby control and/or prevent fungal pathogen attack on a plant.

The present invention also provides any one of the compositions or mixtures described herein for use in controlling and/or preventing fungal attack on a plant.

The present invention also provides use of any one of the compositions or mixtures described herein for controlling and/or preventing fungal attack on a plant.

The present invention also provides a method for the control and/or prevention of plant and/or soil fungal diseases comprising applying any one of the compositions or mixtures described herein to soil, plant, root, foliage, seed, locus of the fungus, and/or a locus in which the infestation is to be prevented so as to thereby control and/or prevent plant and/or soil fungal diseases.

The present invention also provides any one of the compositions or mixtures described herein for use in controlling and/or preventing plant and/or soil fungal diseases.

The present invention also provides use of any one of the compositions or mixtures described herein for controlling and/or preventing plant and/or soil fungal diseases.

In some embodiments, the composition or mixture is applied to a portion of a plant, an area adjacent to a plant, soil in contact with a plant, soil adjacent to a plant, any surface adjacent to a plant, any surface in contact with a plant, a seed, and/or equipment used in agriculture.

In some embodiments, the composition or mixture is applied at an amount in the range of 5 g/ha to 150 g/ha of the compound of Formula I. In some embodiments, the composition or mixture is applied at an amount of 6.25 g/ha of the compound of Formula I. In some embodiments, the composition or mixture is applied at an amount of 10 g/ha of the compound of Formula I. In some embodiments, the composition or mixture is applied at an amount of 12.5 g/ha of the compound of Formula I. In some embodiments, the composition or mixture is applied at an amount of 20 g/ha of the compound of Formula I. In some embodiments, the composition or mixture is applied at an amount of 75 g/ha of the compound of Formula I. In some embodiments, the composition or mixture is applied at an amount of 100 g/ha of the compound of Formula I. In some embodiments, the composition or mixture is applied at an amount of 125 g/ha of the compound of Formula I.

In some embodiments, the composition or mixture is applied at the time of planting.

In some embodiments, the composition or mixture is applied 1 to 60 day(s) after planting.

In some embodiments, the composition or mixture is applied 1 to 9 month(s) after planting.

In some embodiments, the composition or mixture is applied once during a growth season.

In some embodiments, the composition or mixture is applied at least one time during a growth season.

In some embodiments, the composition or mixture is applied two or more times during a growth season.

In some embodiments, the composition or mixture is applied as a foliar, seed treatment and/or a soil application.

The present invention also provides a method of controlling and/or preventing fungal pathogen attack on a plant comprising applying a fungicidally effective amount of a compound having Formula (I):

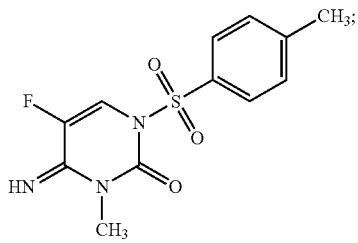

Formula I and at least one adjuvant to soil, plant, root, foliage, seed, locus of the fungus, and/or a locus in which the infestation is to be prevented so as to thereby control and/or prevent fungal pathogen attack on the plant, wherein the adjuvant is selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof; and
(v) sugar-based surfactants.

The present invention also provides a method of controlling and/or preventing plant and/or soil fungal diseases comprising applying a fungicidally effective amount of a compound having Formula (I):

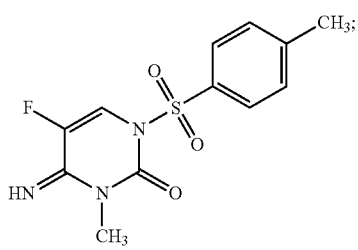

Formula I and at least one adjuvant to soil, plant, root, foliage, seed, locus of the fungus, and/or a locus in which the infestation is to be prevented so as to thereby control and/or prevent plant and/or soil fungal diseases, wherein the adjuvant is selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof: and
(v) sugar-based surfactants.

The present invention provides a method for improving biological activity of a compound of Formula I against fungal pathogen, the method comprising applying the compound of Formula I:

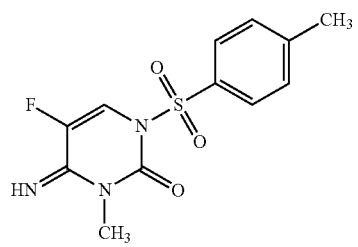

Formula I in presence of at least one adjuvant, wherein the adjuvant is selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof; and
(v) sugar-based surfactants
so as to thereby improve biological activity of the compound of Formula I.

In some embodiments, the compound of Formula I is applied in the presence of at least two adjuvants.

The present invention also provides use of a compound having Formula (I):

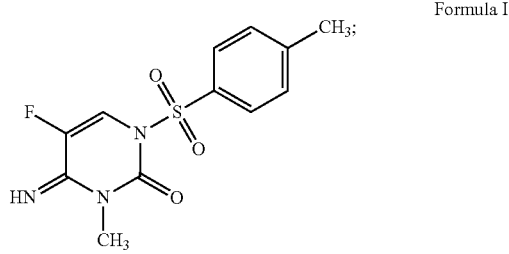 [SMILES: Cc1ccc(S(=O)(=O)n2cc(F)c(=N)n(C)c2=O)cc1]

Formula I and at least one adjuvant selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof; and
(v) sugar-based surfactants,
for (a) controlling and/or preventing fungal pathogen attack on a plant and/or (b) controlling and/or preventing plant and/or soil fungal diseases.

The present invention also provides a compound having Formula (I):

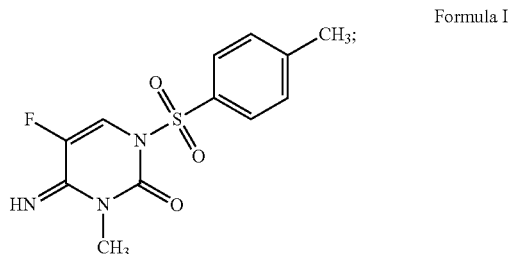

Formula I and at least one adjuvant selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof, and
(v) sugar-based surfactants,
for use in (a) controlling and/or preventing fungal pathogen attack on a plant and/or (b) controlling and/or preventing plant and/or soil fungal diseases.

The present invention provides use of at least one adjuvant selected from the group consisting of:
(i) polyalkylene oxide alkyl ether;
(ii) siloxane polyalkyleneoxide copolymer;
(iii) esters of fatty acid;

(iv) vinylpyrrolidones and derivatives thereof; and
(v) sugar-based surfactants
for improving the biological activity of the compound of Formula (I):

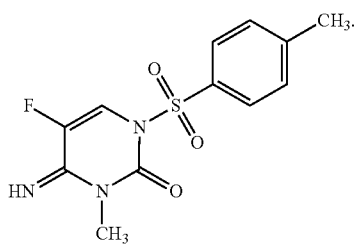
Formula I

The present invention provides an adjuvant selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof, and
(v) sugar-based surfactants
for use in improving the biological activity of the compound of Formula (I):

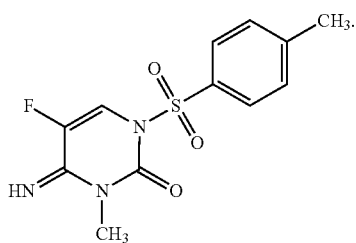
Formula I

Preferred adjuvants are described herein above.

In some embodiments, the compound of Formula I and the adjuvant are applied simultaneously. In some embodiments, the compound of Formula I and the adjuvant are applied sequentially.

In some embodiments, the compound of Formula I and the adjuvant(s) are applied separately. In some embodiments, the compound of Formula I and the adjuvant are applied together. In some embodiments, the compound of Formula I and the adjuvant are applied together as a tank mix. In some embodiments, the compound of Formula I and the adjuvant are formulated as a single composition. In some embodiments.

Adjuvants that are formulated with the compound of Formula I in a composition are built-in adjuvants. Adjuvants that are tank mixed with the compound of Formula I or applied separately, for example via separate spraying, are add-on adjuvants.

In some embodiments, two or more adjuvants are applied wherein at least one of the adjuvants is a built-in adjuvant and at least one of the adjuvants is an add-on adjuvant.

In some embodiments, the compound of Formula I is applied at an amount in the range of 5 g/ha to 150 g/ha. In some embodiments, the compound of Formula I is applied at an amount of 10 g/ha.

The compound of Formula I and compositions and mixtures comprising the compound of Formula I may be applied to control and/or prevent a variety of fungal pathogen and diseases associated therewith. In some embodiments, the fungal pathogen is one of Leaf Blotch of Wheat (*Mycosphaerella graminicola*; anamorph: *Zymoseptoria tritici*), Wheat Brown Rust (*Puccinia triticina*), Stripe Rust (*Puccinia striiformis* f. sp. *tritici*), Scab of Apple (*Venturia inaequalis*), Blister Smut of Maize (*Ustilago maydis*), Powdery Mildew of Grapevine (*Uncinula necator*), Barley scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f. sp. *hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*).

In some embodiments, the fungal pathogen is one of Leaf Blotch of Wheat (*Mycosphaerella graminicola*; anamorph: *Zymoseptoria tritici*), Wheat Brown Rust (*Puccinia triticina*), Stripe Rust (*Puccinia striiformis* f. sp. *tritici*), Scab of Apple (*Venturia inaequalis*), Blister Smut of Maize (*Ustilago maydis*). Powdery Mildew of Grapevine (*Uncinula necator*), Barley scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f. sp. *hordei*), Powdery Mildew of Cucurbits (*Erysiphe cichoracearum*), Anthracnose of Cucurbits (*Glomerella lagenarium*), Leaf Spot of Beet (*Cercospora heticola*), Early Blight of Tomato (*Alternaria solani*), and Net Blotch of Barley (*Pyrenophora teres*).

In some embodiments, the fungal pathogen is *Zymoseptoria tritici*.

In some embodiments, the plant or soil disease is one of *Septoria*, Brown rust, Yellow rust, Powdery Mildew, *Rhynchosporium, Pyrenophora, Microduchium majus, Sclerotinia*, Downy mildew, *Phytophthora, Cercosporea beticola, Ramularia*, ASR. Sigatoka negra.

The methods of the present invention refer to any crop plants, including but not limited to monocotyledons such as sugar cane cereals, rice, maize (corn), and/or; or dicotyledon crop such as beets (such as sugar beet or fodder beet); fruits (such as pomes, stone fruits, or soft fruits, for example apples, pears, plums, peaches, almonds, cherries, strawberries, raspberries, or blackberries); leguminous plants (such as beans, lentils, peas, or soybeans); oil plants (such as rape, mustard, poppy, olives, sunflowers, coconut, castor oil plants, cocoa beans, or groundnuts); cucumber plants (such as marrows, cucumbers or melons); fiber plants (such as cotton, flax, hemp, or jute); citrus fruits (such as oranges, lemons, grapefruit, or mandarins); vegetables (such as spinach, lettuce, cabbages, carrots, tomatoes, potatoes, cucurbits, or paprika): lauraceae (such as avocados, cinnamon, or camphor); tobacco: nuts; coffee; tea; vines: hops; durian; bananas; natural rubber plants; and ornamentals (such as flowers, shrubs, broad-leaved trees, or evergreens, for example conifers).

In some embodiments, the plants are monocotyledonous plants, more preferably, cereals. In a specific embodiment, the cereal crop is wheat. In another specific embodiment, the cereal crop is triticale. In another specific embodiment, the cereal crop is rye. In another specific embodiment, the cereal crop is oat. In a further embodiment, the cereal crop is barley. In another embodiment, the crop plants are rice plants. In still another embodiment, the crop plants are sugar cane plants. In yet another embodiment, the crop plants are corn plants.

In another embodiment, the crop plants are dicotyledonous plants.

In one embodiment, the crop plants are oil seed rape plants.

The compound of Formula I and compositions therefor may also be used as seed treatment to prevent or control phytopathogenic fungi as described in U.S. Patent Application Publication No. 2018-0000082 (published Jan. 4, 2018), the entire content of which is hereby incorporated by reference into this application.

The subject invention also provides a method for the control or prevention of fungal attack on a plant or protecting a plant from fungal attack, the method comprising applying any one of the compositions or mixtures disclosed herein to a seed adapted to produce the plant.

The subject invention also provides a method of treating a plant seed or seedling to produce a plant resistant to fungal attack, the method comprising applying any one of the compositions or mixtures disclosed herein to the plant seed or seedling.

The subject invention also provides a method of protecting a plant from fungal attack, the method comprising applying any one of the compositions or mixtures disclosed herein to the seedling environment.

The subject invention also provides a plant resistant to fungal attack, wherein the plant seed is treated with any one of the compositions or mixtures disclosed herein.

The subject invention also provides a plant seed or seedling adapted to produce a plant resistant to fungal attack, wherein the plant seed or seedling is treated with any one of the compositions or mixtures disclosed herein.

The subject invention also provides a package comprising any one of the compositions or mixtures disclosed herein.

The subject invention also provides use of any one of the mixtures disclosed herein for manufacturing a fungicidal composition. The subject invention also provides use of any one of the mixtures disclosed herein for manufacturing any one of the compositions disclosed herein.

Method of Increasing Stability of Liquid Compositions Comprising the Compound of Formula I:

The present invention also provides a method for increasing stability of a liquid composition comprising a compound of Formula I:

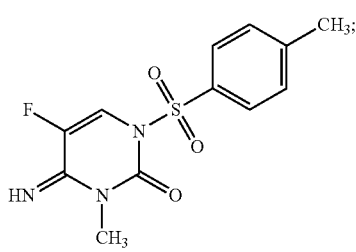

Formula I and a liquid carrier, wherein the method comprises;
a) selecting a liquid carrier wherein the solubility of the compound of Formula I in the liquid carrier is less than 5000 ppm,
b) maintaining the pH value of the composition in the range of 5 to 7.5,
c) maintaining the water content of the composition to less than 0.5% by weight based on the total weight of the composition,
d) adding (i) at least one stabilizing surfactant having crystal growth inhibiting property or (ii) a stabilizing system having a crystal growth inhibiting property to the liquid composition, and/or
e) formulating the composition to have a viscosity of at least 500 cP, so as to thereby increase stability of the composition comprising the compound of Formula I.

The present invention also provides a method for increasing stability of a liquid composition comprising a compound of Formula I:

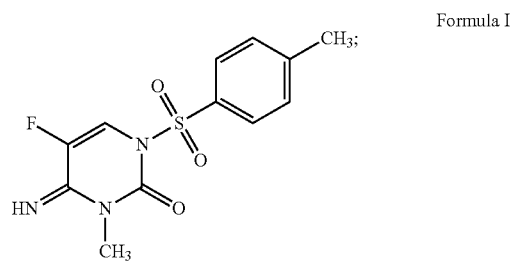 [SMILES: Cc1ccc(S(=O)(=O)n2cc(F)c(=N)n(C)c2=O)cc1]

Formula I and a liquid carrier, wherein the method comprises selecting a liquid carrier wherein the solubility of the compound of Formula I in the liquid carrier is less than 5000 ppm.

In some embodiments, the solubility of compound of Formula I in the liquid carrier is less than 1000 ppm. In some embodiments, the solubility of compound of Formula I in the liquid carrier is about 200 ppm. In some embodiments, the solubility of compound of Formula I in the liquid carrier is about 80 ppm.

The present invention also provides a method for increasing stability of a liquid composition comprising a compound of Formula I:

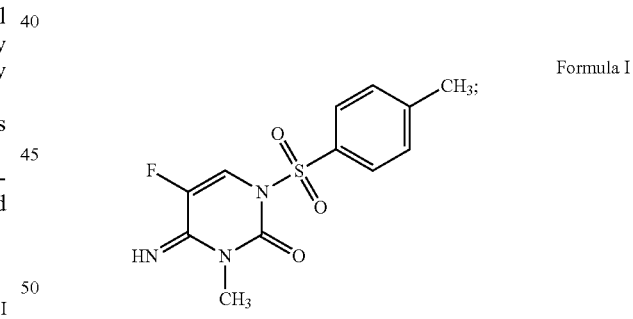

Formula I and a liquid carrier, wherein the method comprises maintaining the pH value of the composition in the range of 5 to 7.5.

In some embodiments, the pH of the composition is measured without further dilution or wetting. In some embodiments, the pH is measured after dilution or wetting with water.

In some embodiment, the pH of the composition is about 5. In some embodiments, the pH of the composition is about 5.5, in some embodiments, the pH of the composition is about 5.8. In some embodiments, the pH of the composition is about 6, In some embodiments, the pH of the composition is about 6.5, In some embodiments, the pH of the composition is about 7. In some embodiments, the pH of the composition is about 7.5.

In some embodiments, the method comprises adding a pH adjuster to the liquid composition.

The present invention also provides use of pH adjuster for increasing the stability of an aqueous suspension concentrate (SC) composition comprising a compound of Formula I:

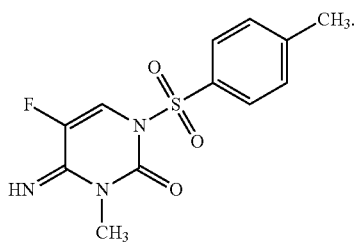

Formula I

The present invention also provides use of pH adjuster for increasing the stability of an aqueous suspoemulsion (SE) composition comprising a compound of Formula I:

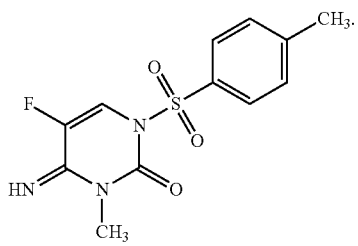

Formula I

The present invention also provides a method for increasing stability of a liquid composition comprising a compound of Formula I:

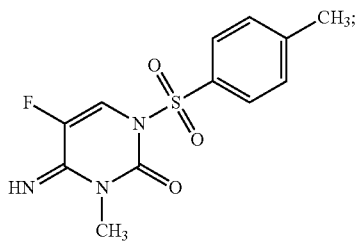

Formula I and a liquid carrier, wherein the method comprises maintaining the water content of the composition to less than 0.5% by weight based on the total weight of the composition.

The present invention also provides a method for increasing stability of a liquid composition comprising a compound of Formula I:

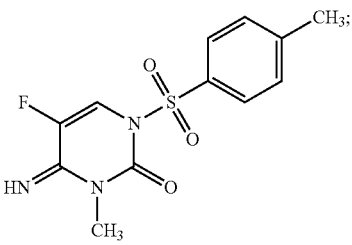

Formula I and a liquid carrier, wherein the method comprises adding (i) at least one stabilizing surfactant having crystal growth inhibiting property or (ii) a stabilizing system having a crystal growth inhibiting property to the liquid composition.

In some embodiments, the stabilizing surfactant is a nonionic derivative of polyalkylene oxide polyaryl ether. In some embodiments, the stabilizing surfactant is an anionic derivative of polyalkylene oxide polyaryl ether.

In some embodiments, at least two stabilizing surfactants are added. In some embodiments, the at least two stabilizing surfactants comprise at least one nonionic derivative of polyalkylene oxide polyaryl ether and at least one anionic derivative of polyalkylene oxide polyaryl ether.

The present invention also provides use of at least one stabilizing surfactant having structure of polyalkylene oxide polyaryl ether for controlling solubility and/or degradation of compound of Formula I:

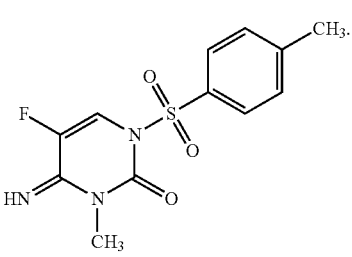

Formula I

In some embodiments, the stabilizing surfactant having structure of polyalkylene oxide polyaryl ether is a non-ionic derivative of polyalkylene oxide polyaryl ether. In some embodiments, the stabilizing surfactant having structure of polyalkylene oxide polyaryl ether is an anionic derivative of polyalkylene oxide polyaryl ether.

In some embodiments, the method further comprises selecting a liquid carrier wherein the solubility of the compound of Formula I in the liquid carrier is less than 5000 ppm.

In some embodiments, the method further comprises maintaining the pH value of the composition in the range of 5 to 7.5.

In some embodiments, the method further comprises maintaining the water content of the composition to less than 0.5% by weight based on the total weight of the composition.

In some embodiments, the method further comprises adding (i) at least one stabilizing surfactant having crystal growth inhibiting property or (ii) a stabilizing system having a crystal growth inhibiting property to the liquid composition.

The present invention also provides a method for increasing stability of a liquid composition comprising a compound of Formula I:

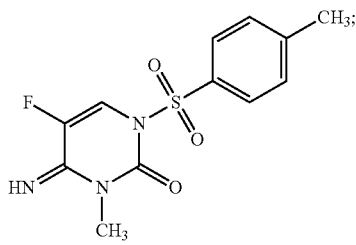

Formula I and a liquid carrier, wherein the method comprises formulating the composition to have a viscosity of at least 500 cP.

In some embodiments, the stable liquid composition is a suspension concentrate (SC) composition.

In some embodiments, the stable composition is a suspoemulsion (SE) composition.

In some embodiments, the stable liquid composition is an oil dispersion (OD) composition.

In some embodiments, the stable liquid composition is an emulsifiable concentrate (EC) composition.

In some embodiments, the mixture or composition is diluted before application. In some embodiments, the mixture or composition is diluted with water. The rate of application of the diluted mixture or composition depends on the concentration of active ingredient(s) in the mixture or composition prior to dilution. Generally, the diluted mixture or composition is applied at a rate of about 5 L/ha to about 120 L/ha.

Process of Phenamine Composition Comprising the Compound of Formula I

The present invention provides a process for preparing the suspension concentrate (SC) composition disclosed herein, the process comprises the steps:
(1) mixing the agriculturally acceptable inert additives and an aqueous liquid carrier to obtain a premix;
(2) adding the compound of Formula I to the premix obtained in step (1) to obtain a mixture: and
(3) milling the resulting mixture of step (2) to obtain the desired composition.

In some embodiments, the process comprises adding additional additive to the mixture of step (2) prior to milling the mixture.

The present invention provides a process for preparing the suspoemulsion (SE) composition disclosed herein, the process comprises the steps;
(1) mixing the agriculturally acceptable inert additives and an aqueous liquid carrier to obtain a premix;
(2) adding the compound of Formula I and at least one adjuvant to the premix obtained in step (1) to obtain a mixture: and
(3) milling the resulting mixture of step (2) to obtain the desired composition.

In some embodiments, step (1) comprises adding a non-aqueous liquid carrier. In some embodiments, step (2) comprises adding a non-aqueous liquid carrier. In some embodiments, the adjuvant added in step (2) is a non-aqueous liquid carrier.

The present invention provides a process for preparing the oil dispersion (OD) composition disclosed herein, the process comprises the steps:
(1) mixing the agriculturally acceptable inert additives and a non-aqueous liquid carrier to obtain a premix,
(2) adding the compound of Formula I to the premix obtained in step (1) to obtain a mixture; and
(3) milling the resulting mixture of step (2) to obtain the desired composition.

The present invention provides a process for preparing the emulsifiable concentrate (EC) composition disclosed herein, the process comprises the steps:
(1) mixing the agriculturally acceptable inert additives and a non-aqueous liquid carrier to obtain a premix;
(2) adding the compound of Formula I to the premix obtained in step (1) to obtain a mixture: and
(3) filtering the solution of step (2) to obtain the desired composition.

Each embodiment disclosed herein is contemplated as being applicable to each of the other disclosed embodiments. Thus, all combinations of the various elements described herein are within the scope of the invention. In addition, when lists are provided, the list is to be considered as a disclosure of any one member of the list.

This invention will be better understood by reference to the Experimental Details which follow, but those skilled in the art will readily appreciate that the specific experiments detailed are only illustrative of the invention as described more fully in the claims which follow thereafter. The invention is illustrated by the following examples without limiting it thereby.

EXPERIMENTAL SECTION

Compound of Formula I can be prepared as described in WO2015/103144 and WO2015/103142.

Preparing a stable composition comprising the compound of Formula I is challenging due to the high sensitivity of the compound. Numerous attempts were made to stabilize the composition. Some of the results are described below.

The compound of Formula I was combined with adjuvant(s) as tank mixes and/or as built-in compositions. Different types of adjuvants with different compositions were tested.

The adjuvants which were tested were polyvinylpyrrolidone (PVP), vinylpyrrolidone and vinyl acetate block copolymer (VP/VA), siloxane polyalkyleneoxide copolymer (Silwett® L-077), tridecyl alcohol ethoxylated 13/9 (Trycol®), alkoxylated alcohol (Agnique®, BP420) and fatty acid methyl ester (Agnique® ME 18 RDF).

Example 1: 450 SC Composition with No Adjuvant

A suspension concentrate (SC) formulation containing 450 g/L of the compound of Formula I and no adjuvant was prepared as follow:

Step I: Preparation of Agriculturally Acceptable Inert Additives Premix

Soft water and Van Gel® B were charged to the vessel and mixed (high shear) to form a solution. The content of the vessel was heated to 60° C. SOPROPHOR® TS/54 (TSP 54) was heated to 50-60° C., and added gradually to the vessel. Supragil® WP, Soprophor® 3D33, $KH_2PO_4$, $Na_2HPO_4$ and SAG 1572 were then added to the homogeneous solution.

Step II: Preparation of the Compound of Formula I

The compound of Formula I (40% W/W) was added to the premix with the surfactants inside, the suspension was milled in a bead mill (0.8-1.2 mm beads) until a particle size distribution of d90<5 μm was reached. The milled suspension was drained from the reactor to new vessel.

Step III: Finalization of the Composition

Propylene glycol was added to the milled suspension and mixed until a uniform suspension was obtained. Soft water and AgRH 23 2% solution were added to the suspension while mixing until a viscosity of 1600-2200 cP was reached.

Mixing was continued until a homogenous solution was obtained. Viscosity was measured by viscometer according to CIPAC method MT 192.

The composition is summarized in Table 1.

TABLE 1

450 SC composition of the compound of Formula I and no adjuvant

| Ingredient trade name | Chemical name and CAS No. | Amount for 1000 L (kg) |
|---|---|---|
| Compound of Formula I tech. as 100% of ADAMA Makhteshim LTD. | 5-fluoro-4-imino-3methyl-1-[4-methylphenyl)sulfonyl]-3,4-dohydropyrimidin-2(1H)-one CAS No. N/A | 450 kg (469 kg for 96%) |
| Supragil ® WP of Solvay or SURFOM ® HRB of OXITENO | Sodium Diisopropylnaphthalene sulphonate CAS No. 1322-93-6 | 5.9 Kg |
| Soprophor ® 3 D 33 of Solvay | POLYARYLPHENYL ETHER PHOSPHATE CAS No. 90093-37-1, 99734-09-5, 7664-38-2 | 47.0 kg |
| Emulsogen ® TS 540 of Clariant or SOPROPHOR ® TS/54 of Solvay | Tristyryl phenol-polyethylene glycol ether CAS No. 70559-25-0 (of Clariant) CAS No. 104376-75-2 (of Solvay) | 17.5 Kg |
| SAG ™ 1572 of Momentive Performance Materials GmbH | Polydimethylsiloxane emulsion CAS No. N/A, 56-81-5 (Glycerine) | 2.0 Kg |
| MPG-MPG USP of INEOS OXIDE or MPG Industrial TG of SHELL EASTERN CHEMICALS or Propylene Glycol Industrial Grade of DOW | 1,2-propanediol CAS No, 57-55-6 | 23.5 Kg |
| MKP (Mono potassium phosphate) of Rotem Amfert Negev Ltd., | $KH_2PO_4$ (Potassium dihydrogenorthophosphate) CAS No. 7778-77-0 | 1.7 Kg |
| Disodium Phosphate Anhydrous of Haifa Chemicals Ltd. | $Na_2HPO_4$ (Disodium Phosphate Anhydrous) CAS No, 7558-79-4 | 6.9 Kg |
| Van Gel ® B of Vanderbilt minerals, LLC. | Magnesium aluminum silicate, Smectite clay; CAS No. 12199-37-0 | 5.9 kg |
| AgRH 23 of Ametech | Xanthan gum CAS No, 11138-66-2 | 2.8 Kg |
| Soft Water | | Up to 1000 L (about 616 kg) |

Appearance: Off-white homogeneous suspension
Density, g/ml: 1.15-1.25
Stability Results:

The physical and chemical stability of composition of Example were tested under various conditions including CIPAC conditions. The stability results are summarized in Table 2.

TABLE 2

Stability results of the composition of Example 1

| Appearance | Start Off-white homogeneous suspension | Room Off-white homogeneous suspension | Oven 54° C. Off-white homogeneous suspension |
|---|---|---|---|
| Concentration of compound of Formula I | 40.80% | 40.4% | 40.2% |

TABLE 2-continued

Stability results of the composition of Example 1

| Appearance | Start Off-white homogeneous suspension | Room Off-white homogeneous suspension | Oven 54° C. Off-white homogeneous suspension |
|---|---|---|---|
| Density, g/ml | 1.18 | 1.21 | — |
| pH | 6.3 | 6.0 | 6.6 |
| Viscosity, sp. 62 at 12 rpm (cP) | 1790 (After 1 day) | 1000 | — |
| Particle size ($D_{90}$) | 6.326 | 6.326 | 10.14 |
| foaming 0.2% | — | 10 ml | 10 ml |
| foaming 1% | — | 25 ml | 25 ml |
| WSR (45 u/75 u) 10% | ok | ok | ok |
| Suspensibility, 0.2 % | — | 101 | 99.7 |
| Suspensibility, 1% | — | 102.8 | 101.6 |

The composition of Example 1 was stored for 2 weeks at 54° C. No crystal growth was observed. The concentration of the compound of Formula I was measured, and the concentration was higher than 95%.

Example 2: 450 SC Composition with a Mixture of Vinylpyrrolidone and Vinyl Acetate Copolymer (VA/VP)

A suspension concentrate (SC) formulation containing 450 g/L of compound of Formula I with 1 built-in adjuvant (VP/VA) was prepared as follow:

Step I: Preparation of Agriculturally Acceptable Inert Additives Premix

Soft water and Van Gel® B were charged to the vessel and mixed (high shear) to form a solution. The content of the vessel was heated to 60° C. SOPROPHOR® TS/54 (TSP 54) was heated to 50-60° C., and added gradually to the vessel. Supragil® WP, Soprophor® 3D33, $KH_2PO_4$, $Na_2HPO_4$ and SAG 1572 were added to the homogeneous solution.

Step II: Preparation of Compound of Formula I

Compound of Formula I (40% W/W) was added to the premix with the surfactants inside. The suspension was milled in a bead mill (0.8-1.2 mm beads) until a particle size of d90<5 μm was reached. The milled suspension was drained from the reactor to a new vessel.

Step III: Finalization of the Composition

Propylene glycol and VP/VA were added to the milled suspension until a uniform suspension was obtained. Soft water and AgRH 23 2% solution were added to the suspension while mixing until a viscosity of 1600-2200 cP was reached. Mixing was continued until a homogenous solution was obtained. Viscosity was measured by viscometer according to CIPAC method MT 192.

The composition is summarized in Table 3.

TABLE 3

450 SC composition with VP/VA

| Ingredient trade name | Chemical name and CAS | Amount for 1000 L (kg) |
|---|---|---|
| Compound of Formula I tech. as 100% of ADAMA Makhteshim LTD. | 5-fluoro-4-imino-3methyl-1-[4-methylphenyl)sulfonyl]-3,4-dohydropyrimidin-2(1H)-one CAS No. N/A | 450 kg (469 kg for 96%) |
| Supragil ® WP of Solvay or SURFOM ® HRB of OXITENO | Sodium Diisopropylnaphthalene sulphonate CAS No. 1322-93-6 | 5.9 Kg |

TABLE 3-continued

450 SC composition with VP/VA

| Ingredient trade name | Chemical name and CAS | Amount for 1000 L (kg) |
|---|---|---|
| Soprophor ® 3 D 33 of Solvay | POLYARYLPHENYL ETHER PHOSPHATE CAS No. 90093-37-1, 99734-09-5, 7664-38-2 | 47.0 kg |
| Emulsogen ® TS 540 of Clariant or SOPROPHOR ® TS/54 of Solvay | Tristyryl phenol-polyethylene glycol ether CAS No. 70559-25-0 (of Clariant), 104376-75-2 (of Solvay) | 17.5 Kg |
| Agrimer ™ VA 6 of Ashland or Sokalan ® VA 64 P of BASF | Mixture of vinylpyrrolidone and vinyl acetate copolymer CAS No. 25086-89-9 | 17.5 Kg |
| SAG ™ 1572 of Momentive Performance Materials GmbH | Polydimethylsiloxane emulsion CAS No, N/A, 56-81-5 (Glycerine) | 2.0 Kg |
| MPG-MPG USP of INEOS OXIDE or MPG Industrial TG of SHELL EASTERN CHEMICALS or Propylene Glycol Industrial Grade of DOW | 1,2-propanediol CAS No. 57-55-6 | 23.5 Kg |
| MKP (Mono potassium phosphate) of Rotem Amfert Negev Ltd., | $KH_2PO_4$ (Potassium dihydrogetiorthophosphate) CAS No. 7778-77-0 | 1.7 Kg |
| Disodium Phosphate Anhydrous of Haifa Chemicals Ltd. | $Na_2HPO_4$ (Disodium Phosphate Anhydrous) CAS No. 7558-79-4 | 6.9 Kg |
| Van Gel ® B of Vanderbilt minerals, LLC. | Magnesium aluminum silicate, Smectite clay; CAS No. 12199-37-0 | 5.9 kg |
| AgRH 23 of Ametech | Xanthan gum CAS No. 11138-66-2 | 2.8 Kg |
| Soft Water | | Up to 1000 L (about 599 kg) |

Appearance: Off-white homogeneous suspension
Density, g/ml: 1.15-1.25
Stability Results:

The composition of Example 2 was stored for 2 weeks at 54° C. No crystal growth was observed. The concentration of the compound of Formula I was measured, and the concentration was slightly less than 95%.

Example 3: 450 SC and 660 SC Compositions with a Mixture of Vinylpyrrolidone/Vinyl Acetate Copolymer and Silwet® L-077

Suspension concentrate (SC) formulations, one containing 450 g/L of the compound of Formula I and two built-in adjuvants (VP/VA and Silwet® L-077), and the other containing 660 g/L of the compound of Formula I and two built-in adjuvants (VP/VA and Silwet® L-077) were prepared as follow:

Step I: Preparation of Agriculturally Acceptable Inert Additives Premix

Soft water (and Van Gel® B for the 450 SC composition) were charged to the vessel and mixed (high shear) to form a solution. The content of the vessel was heated to 60° C. SOPROPHOR® TS/54 (TSP 54) was heated to 50-60° C., and added gradually to the vessel. Supragil® WP, Soprophor® 3D33, $KH_2PO_4$, $Na_2HPO_4$ and SAG 1572 were added to the homogeneous solution.

Step II: Preparation of Compound of Formula I

Compound of Formula I (40% W/W) was added to the premix with the surfactants inside. The suspension was milled in a bead mill (0.8-1.2 mm beads) until a particle size of d90<5 μm was reached. The milled suspension was drained from the reactor to a new vessel.

Step III: Finalization of the Composition

Propylene glycol and Silwet® L-077 were added to the milled suspension until a uniform suspension was obtained. Soft water and AgRH 23 2% solution were added to the suspension while mixing until a viscosity of 1500-2200 cP was reached. Mixing was continued until a homogenous solution was obtained. Viscosity was measured by viscometer according to CIPAC method MT 192.

The 450 SC composition is summarized in Table 4 and the 660) SC composition is summarized in Table 5.

TABLE 4

450 SC composition with VP/VA and Silwet ® L-077

| Ingredient trade name | Chemical name and CAS | Amount for 1000 L (kg) |
|---|---|---|
| Compound of Formula I tech. as 100% of ADAMA Makhteshim LTD. | 5-fluoro-4-imino-3methyl-1-[4-methylphenyl)sulfonyl]-3,4-dohydropyrimidin-2(1H)-one CAS No. N/A | 450 kg (469 kg for 96%) |
| Supragil ® WP of Solvay or SURFOM ® HRB of OXITENO | Sodium Diisopropylnaphthalene sulphonate CAS No. 1322-93-6 | 5.9 Kg |
| Soprophor ® 3 D 33 of Solvay | POLYARYLPHENYL ETHER PHOSPHATE CAS No. 90093-37-1 99734-09-5, 7664-38-2 | 47.0 kg |
| Emulsogen ® TS 540 of Clariant or SOPROPHOR ® TS/54 of Solvay | Tristyryl phenol-polyethylene glycol ether CAS No. 70559-25-0 (of Clariant), 104376-75-2 (of Solvay) | 17.5 Kg |
| Agrimer ™ VA 6 of Ashland or Sokalan ® VA 64 P of BASF | Mixture of vinylpyrrolidone and vinyl acetate copolymer CAS No. 25086-89-9 | 17.5 Kg |
| SAG ™ 1572 of Momentive Performance Materials GmbH | Polydimethylsiloxane emulsion CAS No. N/A, 56-81-5 (Glycerine) | 2.0 Kg |
| Silwet ® L-077 of Momentive | Polyalkyleneoxide modified Heptamethyltrisiloxane, CAS No. 27306-78-1 | 9.0 kg |
| MPG-MPG USP of INEOS OXIDE or MPG Industrial TG of SHELL EASTERN CHEMICALS or Propylene Glycol Industrial Grade of DOW | 1,2-propanediol CAS No. 57-55-6 | 23.5 Kg |
| MKP (Mono potassium phosphate) of Rotem Amfert Negev Ltd., | $KH_2PO_4$ (Potassium dihydrogetiorthophosphate) CAS No. 7778-77-0 | 1.7 Kg |
| Disodium Phosphate Anhydrous of Haifa Chemicals Ltd. | $Na_2HPO_4$ (Disodium Phosphate Anhydrous) CAS No. 7558-79-4 | 6.9 Kg |
| Van Gel ® B of Vanderbilt minerals, LLC. | Magnesium aluminum silicate, Smectite clay; CAS No. 12199-37-0 | 5.9 kg |

TABLE 4-continued

450 SC composition with VP/VA and Silwet ® L-077

| Ingredient trade name | Chemical name and CAS | Amount for 1000 L (kg) |
|---|---|---|
| AgRH 23 of Ametech | Xanthan gum CAS No. 11138-66-2 | 2.8 Kg |
| Soft Water | | Up to 1000 L (about 590 kg) |

Appearance: Off-white homogeneous suspension
Density, g/ml: 1.15-1.25
Stability Results:
The composition of Table 4 was stored for 2 weeks at 54° C. No crystal growth was observed. The concentration of the compound of Formula I was measured, and the concentration was slightly less than 95%.

TABLE 5

660 SC composition with VP/VA and Silwet ® L-077

| Ingredient trade name | Chemical name and CAS | Amount for 1000 L (kg) |
|---|---|---|
| Formula I tech. as 100% of ADAMA Makhteshim LTD. | 5-fluoro-4-imino-3methyl-1-[4-methylphenyl)sulfonyl]-3,4-dohydropyrimidin-2(1H)-one CAS No. N/A | 660 kg (687.5 kg for 96%) |
| Supragil ® WP of Solvay or SURFOM ® HRB of OXITENO | Sodium Diisopropylnaphthalene sulphonate CAS No. 1322-93-6 | 10.0 Kg |
| Soprophor ® 3 D 33 of Solvay | POLYARYLPHENYL ETHER PHOSPHATE CAS No. 90093-37-1 99734-09-5, 7664-38-2 | 56.25 kg |
| Emulsogen ® TS 540 of Clariant or SOPROPHOR ® TS/54 of Solvay | Tristyryl phenol-polyethylene glycol ether CAS No. 70559-25-0 (of Clariant), 104376-75-2 (of Solvay) | 21.25 Kg |
| Agrimer ™ VA 6 of Ashland or Sokalan ® VA 64 P of BASF | Mixture of vinylpyrrolidone and vinyl acetate copolymer CAS No. 25086-89-9 | 13.5 Kg |
| SAG ™ 1572 of Momentive Performance Materials GmbH | Polydimethylsiloxane emulsion CAS No. N/A, 56-81-5 (Glycerine) | 5.0 Kg |
| Silwet ® L-077 of Momentive | Polyalkyleneoxide modified Heptamethyltrisiloxane, CAS No. 27306-78-1 | 9.5 kg |
| MPG-MPG USP of INEOS OXIDE or MPG Industrial TG of SHELL EASTERN CHEMICALS or Propylene Glycol Industrial Grade of DOW | 1,2-propanediol CAS No. 57-55-6 | 37.5 Kg |
| MKP (Mono potassium phosphate) of Rotem Amfert Negev Ltd., | $KH_2PO_4$ (Potassium dihydrogetiorthophosphate) CAS No. 7778-77-0 | 2.5 Kg |
| Disodium Phosphate Anhydrous of Haifa Chemicals Ltd. | $Na_2HPO_4$ (Disodium Phosphate Anhydrous) CAS No. 7558-79-4 | 11.25 Kg |
| AgRH 23 of Ametech | Xanthan gum CAS No. 11138-66-2 | 0.25 Kg |
| Soft Water | | Up to 1000 L (about 423 kg) |

Appearance: Off-white homogeneous suspension
Density, g/ml; 1.15-1.35
Stability Results:
Stability results of the composition of Table 5 are summarized in Table 6 below.

TABLE 6

Stability Results

| | Start | Room after 2 weeks | Oven 54° C. after 2 weeks | Cold 4°C. after 2 weeks | Cold 10° C. after 2 weeks | Oven 40° C. after 8 weeks |
|---|---|---|---|---|---|---|
| Appearance | Off white suspension | Off white suspension | Light phase separation | Off white suspension | Off white suspension | Phase separation |
| Concentration of compound of Formula I | 57.10% | 56.5% | 55.2% | 56.3% | 56.3% | — |
| Density, g/ml | 1.314 | 1.275 | 1.215 | 1.27 | 1.252 | 1.279 |
| pH | 6.6 | 6.6 | 6.5 | 6.5 | 6.6 | 6.36 |
| Viscosity, 12 rpm, sp. 62 (cP) | 1400 | 1800 | 1040 | 690 | 1460 | 1410 |
| Particle size ($D_{90}$) | 4.7 | 4.95 | 5.76 | 4.8 | 4.84 | 5.43 |

Example 4: 450 SC Composition with Two Built-in Adjuvants

A suspension concentrate (SC) formulation containing 450 g/L of compound of Formula I and two built-in adjuvants (PVP and Silwet® L-077) was prepared as follow:

Step I: Preparation Agriculturally Acceptable Inert Additives Premix

Soft water and Van Gel® B were charged to a vessel, and the solutions were mixed (high shear). The content of the vessel was heated to 60° C. SOPROPHOR® TS/54 (TSP 54) was heated to 50-60° C., and added gradually to the vessel. Supragil® WP, Soprophor® 3D33, $KH_2PO_4$, $Na_2HPO_4$ and SAG were then added.

Step II: Preparation of the Compound of Formula I

The compound of Formula I (40% W/W) was added to the premix with the surfactants inside to form a suspension. The suspension was milled in a bead mill (0.8-1.2 mm beads) until a particle size of d90<5 µm was reached. The suspension was drain from the reactor to a new vessel.

Step III: Finalization of the Composition

Propylene glycol and PVP were added to the milled suspension and mixed until a uniform suspension was obtained. Soft water and Ag RH 23 2% solution were added while mixing until a viscosity of 1600-2200 cP was reached. Mixing was continued until the solution was homogenous. Viscosity was measured by viscometer according to CIPAC method MT 192.

The composition is summarized in Table 7 below.

TABLE 7

450 SC composition with PVP and Silwet ® L-077

| Chemical name and CAS | CAS No. | Amount for 1000 L (kg) |
|---|---|---|
| Compound of Formula I | | 450 kg (469 kg for 96%) |
| Sodium Diisopropylnaphthalene sulphonate | CAS No. 1322-93-6 (Supragil WP of Solvay or SURFOM HRB of OXITENO | 5.9 Kg |
| Soprophor ® 3 D 33 of Solvay POLYARYLPHENYL ETHER PHOSPHATE | CAS No. 90093-37-1, 99734-09-5, 7664-38-2 | 47.0 kg |
| Emulsogen ® TS 540 of Clariant or SOPROPHOR ® TS/54 of Solvay Tristyryl phenol-polyethylene glycol ether | CAS No. 70559-25-0 (of Clariant), 104376-75-2 (of Solvay) | 17.5 Kg |
| PVP K-30 of Ashland Vinylpyrrolidone polymer | CAS No. 9003-39-8 | 17.5 Kg |
| SAGT ™ 1572 of Momentive Performance Materials GmbH Polydimethylsiloxane emulsion | CAS No. N/A, 6-81-5 (Glycerine) | 2.0 Kg |
| Silwett ® L-077 of Momentive Polyalkyleneoxide modified Heptamethyltrisiloxane, | CAS No. 27306-78-1 | 9.0 kg |
| MPG-MPG USP of INEOS OXIDE or MPG Industrial TG of SHELL EASTERN CHEMICALS or Propylene Glycol Industrial Grade of DOW 1,2-propanediol | CAS No. 57-55-6 | 23.5 Kg |
| MKP (Mono potassium phosphate) of Rotem Amfert Negev Ltd., $KH_2PO_4$ (Potassium dihydrogenorthophosphate) | CAS No. 7778-77-0 | 1.7 Kg |
| Disodium Phosphate Anhydrous of Haifa Chemicals Ltd $Na_2HPO_4$ (Disodium Phosphate Anhydrous) | CAS No. 7558-79-4 | 6.9 Kg |
| Van Gel ® B of Vanderbilt minerals, LLC. Magnesium aluminum silicate, Smectite clay; | CAS No. 12199-37-0 | 5.9 kg |
| AgRH 23 of Ametech Xanthan gum | CAS No. 11138-66-2 | 2.8 Kg |
| Soft water | | Up to 1000 L (about 590 kg) |

Appearance: Off-white homogeneous suspension

Density, g/ml: 1.15-1.25

Example 5: 300 SE Composition with VP/VA, Agnique® BP 420 and Agnique® ME 18 RD-F A suspoemulsion (SE) composition containing 300 g/L of compound of Formula I and three built-in adjuvants (VP/VA, Agnique®, BP 420 and Agnique®, ME 18 RD-F) was prepared as follow:

Step I: Preparation of Agriculturally Acceptable Inert Additives Premix

Soft water and Van Gel® B were charged to the vessel and mix (high shear). The content of the vessel was heated to 60° C. SOPROPHOR® TS/54 (TSP 54) was heated to 50-60° C., and added gradually to the vessel. Supragil® WP, Soprophor® 3D33, $KH_2PO_4$, $Na_2HPO_4$ and SAG were added to the solution.

Step II: Preparation of Compound of Formula I

Compound of Formula I (40% W/W) was added to the premix with the surfactants inside to form a suspension. The suspension was milled in a bead mill (0.8-1.2 mm beads) until a particle size of d90<5 µm was reached. The milled suspension was drained from the reactor to new vessel.

Step III: Preparation of the Organic Phase

Agnique® ME RDF, Atlox™ 4914, Atlas™ G5002L, Genapol® X80 and Agnique® BP 420 were charged to the vessel and mixed until a homogeneous solution was obtained. Before adding the SE to the suspension, the content of the vessel was mixed (high shear) for at least 10 min until a droplet size of D90=10 µm was reached.

Step IV: Finalization of the Composition

Propylene glycol and VP/VA were added to the milled suspension and mixed until a uniform suspension was obtained. The SE solution was added gradually to the milled suspension in three doses. Between each dose, Atlox™ 4913, soft water and Ag RH 23 2% solution were added while mixing until a viscosity of 1600-2200 cP was reached. Mixing was continued until a homogenous solution was obtained. Viscosity was measured by viscometer according to CIPAC method MT 192.

The compositions are summarized in Table 8 below.

TABLE 8

300 SE composition with VP/VA, Agnique ® 420 and Agnique ® ME 18 RD-F

| Ingredient trade name | Chemical name and CAS | Function | Amount for 1000 L (kg) |
|---|---|---|---|
| Compound of Formula I | 5-fluoro-4-imino-3methyl-1-[4-methylphenyl)sulfonyl]-3,4-dohydropyrimidin-2(1H)-one CAS No. N/A | | 300 kg (312.5 kg for 96%) |
| Supragil ® WP of Solvay or SURFOM ® HRB of OXITENO | Sodium Diisopropylnaphthalene sulphonate CAS No. 1322-93-6 ( ) | | 4.0 Kg |
| Soprophor ® D 33 of Solvay | POLYARYLPHENYL ETHER PHOSPHATE CAS No. 90093-37-1, 99734-09-5, 7664-38-2 | | 31.5 kg |
| Emulsogen ® TS 540 of Clariant or SOPROPHOR ® TS/54 of Solvay | Tristyryl phenol-polyethylene glycol ether CAS No. 70559-25-0 (of Clariant), 104376-75-2 (of Solvay) | | 12.0 Kg |
| Agrimer ™ VA 6 of Ashland or Sokalan ® VA 64 P of BASF | Mixture of vinylpyrrolidone and vinyl acetate copolymer CAS No. 25086-89-9 | | 17.5 Kg |
| SAG ™ 1572 of Momentive Performance Materials GmbH | Polydimethylsiloxane emulsion CAS No. N/A, 56-81-5 (Glycerine) | | 2.0 Kg |
| MPG - MPG USP of INEOS OXIDE or MPG Industrial TG of SHELL EASTERN CHEMICALS or Propylene Glycol Industrial Grade of DOW | 1.2-propanediol CAS No. 57-55-6 | | 23.5 Kg |
| MKP (Mono potassium phosphate) of Rotem Amfert Negev Ltd. | KH$_2$PO$_4$ (Potassium dihydrogenorthophosphate) CAS No. 7778-77-0 | | 1.2 Kg |
| Disodium Phosphate Anhydrous of Haifa Chemicals Ltd. | Na$_2$HPO$_4$ (Disodium Phosphate Anhydrous) CAS No. 7558-79-4 | | 4.6 Kg |
| Van Gel ® B of Vanderbilt minerals, LLC. | Magnesium aluminum silicate, Smectite clay; CAS No. 12199-37-0 | | 4.0 kg |
| Agnique ® ME 18 RD-F | Rapeseed oil fatty acid methyl ester. CAS No. 67762-38-3 | | 64.5 kg |
| Atlox ™ 4914 of Croda | Random copolymer (alkyd-PEG resin). CAS No. N/A | | 9.5 kg |
| Atlas ™ G5002L of Croda | Polyalkylene oxide block copolymer. CAS No. N/A | | 29.0 kg |
| Genapol ® X80 of Croda | A fatty alcohol polyglycol ether. CAS No. 9043-30-5 | | 13.0 kg |
| Agnique ® BP 420 of BASF | Alcohols, C16-18, ethoxylated propoxylated. CAS No. 68002-96-0 | | 97.0 kg |
| Atlox ™ 4913 of Croda | Methyl ether methacrylate copolymer. CAS No. N/A. Propylene glycol. CAS No. 57-55-6 | | 35.0 kg |

TABLE 8-continued

300 SE composition with VP/VA, Agnique ® 420 and Agnique ® ME 18 RD-F

| Ingredient trade name | Chemical name and CAS | Function | Amount for 1000 L (kg) |
|---|---|---|---|
| AgRH 23 of Ametech | Xanthan gum CAS No. 11138-66-2 | | 1.0 Kg |
| Soft Water | | | Up to 1000 L (about 511.0 kg) |

Appearance: Off-white homogeneous suspension
Density, g/ml: 1.14-1.25

Example 6: 300 SE Composition with PVP, Agnique® BP 420 and Agnique® ME 18 RD-F

SE composition containing 300 g/L of compound of Formula I and three built-in adjuvants (PVP, Agnique® BP 420 and Agnique® ME 18 RD-F) was prepared as follow:

Step I: Preparation of Agriculturally Acceptable Inert Additives Premix

Soft water and Van Gel® B were charged to the vessel and mixed (high shear). The content of the vessel was heated to 60° C. SOPROPHOR® TS/54 (TSP 54) was heated to 50-60° C., and added gradually to the vessel. Supragil®10 WP, Soprophor® 3D33, KH$_2$PO$_4$, Na$_2$HPO$_4$ and SAG were added to the solution.

Step II: Preparation of Compound of Formula I

Compound of Formula I (40% W/W) was added to the premix with the surfactants inside to form a suspension. The suspension was milled in a bead mill (0.8-1.2 mm beads) until a particle size of d90<5 µm was reached. The milled suspension was drained from the reactor to new vessel.

Step III: Preparation of the Organic Phase

Agnique® ME RDF, Atlox™ 4914, Atlas®1. G5002L, Genapol® X80 and Agnique® BP 420 were charged to the vessel and mixed until a homogeneous solution was obtained. Before adding the SE to the suspension, the content of the vessel was mixed (high shear) for at least 10 min until a droplet size of D90=10 µm was reached.

Step IV: Finalization of the Composition

Propylene glycol and PVP were added to the milled suspension and mixed until a uniform suspension was obtained. The SE solution was added gradually to the milled suspension in three doses. Between each dose, Atlox™ 4913, soft water and Ag RH 23 2% solution were added while mixing until a viscosity of 1600-2200 cP was reached. Mixing was continued until a homogenous solution was obtained. Viscosity was measured by viscometer according to CIPAC method MT 192.

The compositions are summarized in Table 9 below.

TABLE 9

300 SE Composition with PVP, Agnique ® BP 420 and Agnique ® ME 18 RD-F

| Ingredient trade name | Chemical name and CAS | Amount for 1000 L (kg) |
|---|---|---|
| Compound of Formula I. | 5-fluoro-4-imino-3methyl-1-[4-methylphenyl)sulfonyl]-3,4-dohy-dropyrimidin-2(1H)-one CAS No. N/A | 300 kg (312.5 kg for 96%) |

TABLE 9-continued

300 SE Composition with PVP, Agnique ® BP 420 and Agnique ® ME 18 RD-F

| Ingredient trade name | Chemical name and CAS | Amount for 1000 L (kg) |
|---|---|---|
| Supragil ® WP of Solvay or SURFOM ® HRB of OXITENO | Sodium Diisopropylnaphthalene sulphonate CAS No. 1322-93-6 | 4.0 Kg |
| Soprophor ® 3 D 33 of Solvay | POLYARYLPHENYL ETHER PHOSPHATE CAS No. 90093-37-1, 99734-09-5, 7664-38-2 | 31.5 kg |
| Emulsogen ® TS 540 of Clariant or SOPROPHOR ® TS/54 of Solvay | Tristyryl phenol-polyethylene glycol ether CAS No. 70559-25-0 (of Clariant), 104376-75-2 (of Solvay) | 12.0 Kg |
| PVP K-30 of Ashland or | Vinylpyrrolidone polymer CAS No. 9003-39-8 | 17.5 Kg |
| SAG ™ 1572 of Momentive Performance Materials GmbH | Polydimethylsiloxane emulsion CAS No. N/A, 56-81-5 (Glycerine) | 2.0 Kg |
| MPG - MPG USP of INEOS OXIDE or MPG Industrial TG of SHELL EASTERN CHEMICALS or Propylene Glycol Industrial Grade of DOW | 1,2-propanediol CAS No. 57-55-6 | 23.5 Kg |
| MKP (Mono potassium phosphate) of Rotem Amfert Negev Ltd., | $KH_2PO_4$ (Potassium dihydrogenortho-phosphate) CAS No. 7778-77-0 | 1.2 Kg |
| Disodium Phosphate Anhydrous of Haifa Chemicals Ltd. | $Na_2HPO_4$ (Disodium Phosphate Anhydrous) CAS No. 7558-79-4 | 4.6 Kg |
| Van Gel ® B of Vanderbilt minerals, LLC. | Magnesium aluminum silicate, Smectite clay; CAS No. 12199-37-0 | 4.0 kg |
| Agnique ® ME 18 RD-F | Rapeseed oil fatty acid methyl ester. CAS No. 67762-38-3 | 64.5 kg |
| Atlox ™ 4914 of Croda | Random copolymer (alkyd-PEG resin). CAS No. N/A | 9.5 kg |
| Atlas ™ G5002L of Croda | Polyalkylene oxide block copolymer. CAS No. N/A | 29.0 kg |
| Genapol ® X80 of Croda | A fatty alcohol polyglycol ether. CAS No. 9043-30-5 | 13.0 kg |
| Agnique ® BP 420 of BASF | Alcohols, C16-18, ethoxylated propoxylated, CAS No. 68002-96-0 | 97.0 kg |
| Atlox ™ 4913 of Croda | Methyl ether methacrylate copolymer. CAS No. N/A. Propylene glycol. CAS No. 57-55-6 | 35.0 kg |
| AgRH 23 of Ametech | Xanthan gum CAS No. 11138-66-2 | 1.0 Kg |
| Soft Water | | Up to 1000 L (about 511.0 kg) |

Appearance: Off-white homogeneous suspension
Density, g/ml: 1.14-1.25

Example 7: Suspension Concentrate (SC) Composition without Stabilizing Surfactant at pH of Approx. 7

A suspension concentrate (SC) formulation containing 450 g/L of the compound of Formula I and no stabilizing surfactant was prepared as follows; In water, 4% Atlox™ 4913, 2% Ethylan™ NS 500 LQ/Antarox® B 848, 0.5% Supragil® WP and 0.1% antifoam (SAG™ 1572) were added and mixed until a homogeneous solution was obtained.

Compound of Formula I was added while mixing (high sheer). Mixing was performed for 5 minutes. The mixture was put in the Tinky with a few beads for 20 minutes.

The rest of the materials were inserted into the suspension and mixed, divided to vials and put in the room and oven.

The formulation is summarized in Table 10.

TABLE 10

450 SC composition of the compound of Formula I with pH approx. = 7

| Raw Material | CAS No. | Quantity for 1000 Liters (up to 1180 kg with 1.18 gr/ml density) |
|---|---|---|
| Compound of Formula I, tech. as 100% | | 450 kg (469 kg for 96%) |
| 4% Atlox ™ 4913 | 1322-93-6 | 47 |
| 2% Ethylan ™ NS 500 LQ/Antarox ® B 848 | 90093-37-1 | 24 |
| 0.5% Supragil ® WP | 70559-25-0 | 59 |
| Propylene Glycol | 57-55-6 | 24 |
| SAG ™ 1572 (Polydimethylsiloxane antifoam emulsion) | Trade secret | 30 |
| Xantan Gum AG RH 2.0% | 11138-66-2 | 118 |
| $KH_2PO_4$ (Monopotassium phosphate) | 7778-77-0 | 1.7 |
| $Na_2HPO_4$ (Disodium phosphate) | 7558-79-4 | 6.9 |
| water DI | | Up to 1000 L (about 419.4 kg) |

Stability Results

The SC composition was placed in room temperature and in oven (54° C.) for 24 hours and the concentration was checked. Crystalline particle was observed and the degradation of the compound of Formula I was measured. The results showed that there was more than 5% decrease in concentration of the compound of Formula I.

Example 8: Suspension Concentrate Composition with Stabilizing Surfactants at pH 3.5

A suspension concentrate (SC) formulation containing 450 g/L of compound of Formula I and two stabilizing surfactants (Soprophor® 3D33 and Soprophor® TS/54) was prepared as follow:

Step I: Preparation of Agriculturally Acceptable Inert Additives Premix

Soft water was added gradually to a vessel containing preheated SOPROPHOR® TS/54 (TSP 54). The content of the vessel was mixed and heated to 50-65° C., until a homogeneous solution was obtained. Supragil® WP, Soprophor® 3D33, $KH_2PO_4$, $Na_2HPO_4$ and SAG™ 1572 were added to the solution.

Step II: Preparation of the Compound of Formula I

Compound of Formula I (40% W/W) was added to the premix with the surfactants inside to form a suspension. The suspension was milled in a bead mill (0.8-1.2 mm beads) until a particle size of d90<5 μm was reached. The milled suspension was drained from the reactor to a new vessel.

Step III: Finalization of the Composition

Propylene glycol was added to the milled suspension and mixed until a uniform suspension was obtained. Soft water and AgRH 23 2% solution were added to the suspension while mixing until a viscosity of 1600-2200 cP was reached. Mixing was continued until a homogenous solution was obtained. Viscosity was measured by viscometer according to CIPAC method MT 192.

The composition is summarized in Table 11.

TABLE 11

450 SC composition of compound Formula I with pH = 3.5

| Ingredient trade name | Chemical name and CAS No. | Amount for 1000 L (kg) |
|---|---|---|
| Compound of Formula I, tech. as 100% of ADAMA Makhteshim LTD. | 5-fluoro-4-imino-3meth-yl-1-[4-methylphen-yl)sulfonyl]-3,4-dohydro-pyrimidin-2(1H)-one CAS No. N/A | 450 kg (469 kg for 96%) |
| Supragil ® WP of Solvay or SURFOM ® HRB of OXITENO | Sodium Diisopropylnaphthalene sulphonate CAS No. 1322-93-6 | 5.9 Kg |
| Soprophor ® D 33 of Solvay | POLYARYLPHENYL ETHER PHOSPHATE CAS No. 90093-37-1, 99734-09-5, 7664-38-2 | 47.0 kg |
| Emulsogen™ TS 540 of Clariant or SOPROPHOR ® TS/54 of Solvay | Tristyryl phenol-polyethylene glycol ether CAS No. 70559-25-0 (of Clariant), 104376-75-2 (of Solvay) | 17.5 Kg |
| SAG ™ 1572 of Momentive Performance Materials GmbH | Polydimethylsiloxane emulsion CAS No. N/A, 56-81-5 (Glycerine) | 2.0 Kg |
| MPG - MPG USP of INEOS OXIDE or MPG Industrial TG of SHELL | 1,2-propanediol CAS No. 57-55-6 | 23.5 Kg |
| EASTERN CHEMICALS or Propylene Glycol Industrial Grade of DOW | | |
| AgRH 23 of Ametech | Xanthan gum CAS No. 11138-66-2 | 2.8 Kg |
| Soft Water | | Up to 1000 L (about 621 kg) |

Stability Results:

The concentration in the accelerated storage after 2 weeks in the oven at 54° C., decreased in 6%. A small amount of crystalline particles was observed. However, the concentration of compound of Formula I was reduced.

Accordingly, the pH of the composition must be maintained within the range of 5.0-7.5 in order to have a stable SC formulation.

Example 9: Suspension Concentrate Compositions with Stabilizing Surfactants at pH 4 and 8

Table 12 shows two SC compositions (BN 161213-5-Sop3d_TSP54_PG and BN 161213-6-Sop3d_TSP54_PG) each containing two stabilizing surfactants (Soprophor® 3D33 and Soprophor® TS/54). BN 161213-5-Sop3d_TSP54_PG has a low pH of 4 and BN 161213-6-Sop3d_TSP54_PG has a high pH of 8.

Neither composition was stable. The concentration decreased in the oven in the first composition and major viscosity elevation was observed for the second composition. Viscosity was measured by viscometer according to CIPAC method MT 192.

TABLE 12

Comparison of SC compositions at pH 4 and 8

| Composition: | BN 161213-5-Sop3d_TSP54_PG PH4 | | | BN 161213-6-Sop3d_TSP54_PG PH8 | | |
|---|---|---|---|---|---|---|
| | % W/W | g/1L | g/2.5 | % W/W | g/1L | g/2.5 |
| Compound of formula I | 44.51 | 489.58 | 1223.96 | 44.51 | 489.58 | 1223.96 |
| Supragil ® WP | 0.50 | 5.50 | 13.75 | 0.50 | 5.50 | 13.75 |
| Soprophor ® 3d33 | 4.00 | 44.00 | 110.00 | 4.00 | 44.00 | 110.00 |
| TSP54 | 1.50 | 16.50 | 41.25 | 1.50 | 16.50 | 41.25 |
| SAG ™1572 | 0.15 | 1.65 | 4.13 | 0.15 | 1.65 | 4.13 |
| Water | 32.24 | 354.67 | 886.67 | 31.84 | 350.27 | 875.67 |
| sub total | 82.90 | 911.90 | 2279.75 | 82.50 | 907.50 | 2268.75 |

Milling parameters: 5 cycles, the first two at 2500-3000 rpm, the third at 3100 rpm and the final two at 3500-3600 rpm (temp. 24-28° C.)

After milling, the milled solution is split into batches

| Total milled formulation: 2000 gr | | | | | | |
|---|---|---|---|---|---|---|
| | | | 200.00 | | | 200.00 |
| Factor | | | 0.09 | | | 0.09 |
| Xantan gum Ag/RH 2% | 12.00 | 132.00 | 28.95 | 12.00 | 132.00 | 28.95 |

TABLE 12-continued

Comparison of SC compositions at pH 4 and 8

|  | BN 161213-5-Sop3d_TSP54_PG PH4 | | | BN 161213-6-Sop3d_TSP54_PG PH8 | | |
|---|---|---|---|---|---|---|
| Composition: | % W/W | g/1L | g/2.5 | % W/W | g/1L | g/2.5 |
| Propylene glycol | 5.00 | 55.00 | 12.06 | 5.00 | 55.00 | 12.06 |
| Citric acid | 0.10 | 1.10 | 0.24 | 0.00 | 0.00 | 0.00 |
| Trisodium citrate |  |  |  | 0.50 | 5.50 | 1.21 |
| Urea | 0.00 | 0.00 | 0.00 | 0.00 | 0.00 | 0.00 |
| Total | 100.0 | 1100.00 | 241.25 | 100.0 | 1100.00 | 242.22 |

|  | BN 161213-5-Sop3d_TSP54_PG PH4 | BN 161213-6-Sop3d_TSP54_PG PH8 |
|---|---|---|
| PH | 4 | 8 |
| Viscosity (cP) 12 rpm S62 | 1440 | 1610 |
| Concentration of compound of formula I (%) | 44.4 | 37.7 |
| Concentration of compound of formula I (%) oven 2W 54° C. (%) | 36.4 | 38 |
| Comments | Viscosity elevation, occurred and crystallization | Viscosity elevation aggregation and crystallization occurred. |

When pH is low, i.e. pH 4, there is degradation of the compound for Formula I. In Example 12, the amount of the compound of Formula I in the composition decreased from 44.4% by weight based on the total weight of the composition to 31.1% by weight based on the total weight of the composition. When pH is high, the physical stability of the composition decreases. In Example 12, the composition became inhomogeneous and viscosity elevated.

As a conclusion, there is a need to maintain the pH of the composition in the range of 5.0-7.5 in order to have a stable SC formulation.

Example 10: 250 OD Composition with Agnique ME 18 RD-F (OD Composition A)

An oil dispersion (OD) composition containing 250 g/L of compound of Formula I was prepared as follows:

Step I: Preparation of Agriculturally Acceptable Inert Additives Premix in Non-Aqueous Carrier (Fatty Acid Ester)

Bentone SD®-1 was added to Agnique® ME 18 RD-F under high shear (3000 rpm) using a large round hole Silverson mixer and mixed for 5 minutes.

The mixture was milled in a colloid mill (IKA MagicLab) until the viscosity at 10 s$^{-1}$ was no longer significantly increasing (50 passes). Viscosity was measured by viscometer according to CIPAC method MT 192.

Agnique® ME 18 RD-F was added to a suitable vessel and the pre-gel was added and mixed for 5 minutes.

Emulsifiers and dispersants were added and mixed for 15 minutes until homogenous.

Step II: Preparation of Compound of Formula I

Compound of Formula I was added under agitation and mixed until homogenous. Once all active ingredients were added, it was mixed for 15 minutes.

Step III: Finalization of the Composition

The sample was milled in Eiger mini motor mill (80% 0.75 mm-1.0 mm bead charge at 4000 rpm) for 15 minutes.

The formulation is summarized in Table 13.

TABLE 13

| 250 OD composition of the compound of Formula I (A) | |
|---|---|
| Ingredient | % w/w |
| compound of Formula I | 25 |
| Atlox ™ 4912 | 5 |
| Atlox ™ 4915 | 2 |
| Rhodocal ® 70/B | 5 |
| Genapol ® X 080 | 4 |
| Genapol ® X 050 | 8 |
| Bentone SD ®-1 | 1.5 |
| Agnique ® ME 18 RD-F | up to 100% (49.5) |

Density 1 gr/ml

Example 11: 250 OD Composition with Agnique® ME 18 RD-F (OD Composition B)

An oil dispersion (OD) composition containing 250 g/L of compound of Formula I was prepared as follows:

Step I: Preparation of Agriculturally Acceptable Inert Additives Premix in Non-Aqueous Carrier (Fatty Acid Ester)

Bentone SD®-1 was added to Agnique® ME 18 RD-F under high shear (3000 rpm) using a large round hole Silverson mixer and mixed for 5 minutes.

The mixture was milled in a colloid mill (IKA MagicLab) until the viscosity at 10 s$^{-1}$ was no longer significantly increasing (50 passes). Viscosity was measured by viscometer according to CIPAC method MT 192.

Agnique® ME 18 RD-F was added to a suitable vessel and the pre-gel was added and mixed for 5 minutes.

Emulsifiers and dispersants were added and mixed for 15 minutes until homogenous.

Step II: Preparation of Compound of Formula I

Compound of Formula I was added under agitation and mixed until homogenous. Once all active ingredients were added, it was mixed for 15 minutes.

Step III: Finalization of the Composition

The sample was milled in Eiger mini motor mill (80% 0.75 mm-1.0 mm bead charge at 4000 rpm) for 15 minutes. The formulation is summarized in Table 14.

TABLE 14

250 OD composition of the compound of Formula I (B)

| Ingredient | % w/w |
|---|---|
| Compound of Formula I | 25 |
| Atlox ™ 4912 | 2 |
| Atlox ™ 4915 | 1.25 |
| Aerosol ® OT-SE | 5 |
| Genapol ® x80 | 5 |
| Rhodasurf ® LA30 | 5 |
| Bentone SD ®-1 | 1.25 |
| Agnique ® ME 18-RD-F (solvent/adjuvant) | 55.5 |

The composition of Example 11 was physically stable (phase separation was observed, however it was homogeneous after mixing). Chemical degradation was observed after 2 weeks of storage at 54° C. (<10% of the compound of Formula I degraded).

Example 12: 250 OD Composition with Agnique® ME 18 RD-F (OD Composition C)

An oil dispersion (OD) composition containing 250 g/L of compound of Formula I was prepared using a process similar to Example 10 and 11.

The formulation is summarized in Table 15.

TABLE 15

250 OD composition of the compound of Formula I (C)

| Component | WEIGHT |
|---|---|
| Compound of Formula I (100% purity) | 250 |
| Atlox ™ 4912 | 30 |
| Atlox ™ 4915 | 20 |
| Genapol ® X080 | 37.5 |
| Genapol ® X050 | 75 |
| Bentone SD ®-1 | 5 |
| Attagel ® 50 | 5 |
| Rhodacal ® 70/B | 50 |
| Agnique ® ME 18 RD-F | TO 1 LITER (~527.5) |

The composition of Example 12 was stored for 2 weeks at 54° C., and no significant degradation of the compound of Formula I was observed Example 13: 250 OD Composition with Agnique® ME 18 RD-F (OD Composition D)

Step I: Preparation of Agriculturally Acceptable Inert Additives Premix in Non-Aqueous Carrier (Fatty Acid Ester)

Agnique® ME 18 RD-F was added to a suitable vessel and the pre-gel was added and mixed for 5 minutes.

Emulsifiers and dispersants were added and mixed for 15 minutes until homogenous.

Step II: Preparation of Compound of Formula I

Compound of Formula I was added under agitation and mixed until homogenous. Once all active ingredients were added, it was mixed for 15 minutes.

The mixture was milled in a colloid mill (IKA MagicLab) until the viscosity at 10 $s^{-1}$ was no longer significantly increasing (50 passes). Viscosity was measured by viscometer according to CIPAC method MT 192.

Step III: Finalization of the Composition

The sample was milled in Eiger mini motor mill (80% 0.75 mm-1.0 mm bead charge at 4000 rpm) for 15 minutes.

TABLE 16

250 OD composition of the compound of Formula I (D)

| Ingredient | % w/w |
|---|---|
| compound of Formula I | 25 |
| Atlox ™ 4912 | 3 |
| Atlox ™ 4915 | 2 |
| Rhodocal ® 70/B or Aerosol ® OT-SE* | 6 |
| Alkamuls ® BR or Atlas ™ G5002L* | 6 |
| Genapolt ® X 050 | 3 |
| Agnique ® ME 18 RD-F | up to 100% (55) |

*The actual formulation was prepared with Rhodocal ® 70/B and Alkamuls ® BR. The Aerosol ® OT-SE and Atlas ™ G5002 are written as an additional option, however they were not tested.

TABLE 17

Compound of Formula I—250 g/L OD formulation specification

| Characteristic | Specification |
|---|---|
| Appearance | Brown to White, homogenous liquid |
| Persistent Foam (CIPAC MT 47.3) | <60 mL after 1 minute |
| pH (1% deionized water, CIPAC MT 75.3) | 4-9 |
| Viscosity at 10 $s^{-1}$ | >500 mPa · s |
| Yield Stress | >1 Pa |
| Dispersion Stability (CIPAC MT 180) | <2 mL separation after 30 minutes |
| Wet Sieve (CIPAC MT 185) | <2% reside on 75 μm sieve |
| Particle Size (CIPAC MT 187) | D(50) μm: <4, D(90) μm: <20 |
| Density (gr/ml) | 0.96-1.04 |

Example 14: EC Compositions Comprising the Compound of Formula I

Three emulsifiable concentrate (EC) compositions (A. B and C) each containing 50 g/L of the compound of Formula I were prepared.

The process of preparing composition C is summarized below. (Compositions A and B may be prepared using a similar process.)

1. Alkamuls® 14/1R (CO60) was melted in a hot bath/oven at 50° C.;
2, benzyl acetate and propylene carbonate were charged to the vessel and heated to 50° C.;
3, the compound of Formula I was added to the reactor while mixing until a clear solution was obtained;
4. Ninate® 60. TSP16 and molten Alkamuls® 14/R (4) were added gradually to the reactor while mixing until clear solution was obtained;
5, mixing was continued for 1 hour while the reactor was cooled to room temperature; and
6, the solution was discharged from the reactor through a filter (5 μm).

Compositions A, B and C are summarized in Tables 18, 19 and 20, respectively. The stability results for compositions B and C are summarized in Tables 21 and 22.

TABLE 18

EC Formulation A

| Raw Material | Manufacture | CAS No. | Function | Quantity for 1000 Liters |
|---|---|---|---|---|
| Compound of Formula I | | | A.I. | 50 kg (52 kg for 96%) |
| JEFFSOL ® AG 1705 benzyl acetate | Hunstman | 140-11-4 | Solvent | 730 kg |
| Nansa ® EVM 70/2E Calcium dodecyl benzene sulphonate | Hunstman | 90194-25-6 | Surfactant | 78 kg |
| Toximul ® 8320 eo/po block copolymer | Stepan | 9038-95-5 | Surfactant | 46.8 kg |
| Synperonic ® 13/10 tridecyl alcohol ethoxylated | Croda | 24938-91-8 | Surfactant | 31.2 |
| Hallcomid ® M-8-10 dimethyl fatty acid amide | Stepan | 45280-17 | Solvent | 104 |

Density, g/ml: 1.00-1.08

Crystal formation was observed in this formulation after a week in 0° C., and after a few weeks at room temperature.

TABLE 19

EC Formulation B

| Raw Material | manufacturer | CAS No. | Function | Quantity for 1000 Liters |
|---|---|---|---|---|
| Compound of Formula I | | | A.I. | 50 kg (52 kg for 96%) |
| JEFTSOL ® AG 1705 benzyl acetate | Hunstman | 140-11-4 | Solvent | 834.0 kg |
| Genagen ® NBP N butyl pyrrolidone | Clariant | 3470-98-2 | Co-solvent | 104 kg |
| Castor oil ethylene oxide (20) | Akzo Nobel | 61791-12-6 | Surfactant | 26 kg |
| Castor oil ethylene oxide (60) | Akzo Nobel | 61791-12-6 | Surfactant | 26 kg |

TABLE 20

Stability Results of Formulation B

| Appearance | Yellowish solution |
|---|---|
| Density, g/ml | 1.04 |
| pH (1%) | 5.2 |
| Emulsion stability (0.2%, 1%) | Max. 0.2 ml separation after 2 hours. |
| Cold test | no crystal growth |

TABLE 21

EC Formulation C

| Ingredient trade name | Chemical name and CAS No. | Amount for 1000 L (kg) |
|---|---|---|
| Compound of Formula I tech. as 100% of ADAMA Makhteshim LTD. | 5-fluoro-4-imino-3methyl-1-[4-methylphenyl)sulfonyl]-3,4-dohydropyrimidin-2(1H)-one CAS No. N/A | 50 kg (52.1 kg for 96%) |
| ALKAMULS ® 14/R of Solvay | ETHOXYLATED CASTOR OIL CAS No. 61791-12-6 | 10.4 Kg |
| RHODACAL ® 60/BE of Solvay or AGNIQUE ® ABS 60 C-EH of Cognis or NANSA ® EVN 70/2E of Innospec | Benzenesulfonic acid, C10-13-(linear)alkyl derivs., calcium salt CAS No. 104-76-7 (2-ethylhexan-1-ol), 57-55-6 (Propylene glycol, only for NANSA) | 34.6 Kg |
| SUPROPHOR ® TS/16 of Solvay or EMULSOGEN ® TS 160 of Clariant or Agnique ® TSP 16 of BASF | Tristyryl phenol-polyethylene glycol ether CAS No. 104376-75-2 (Only for Solvay), 99734-09-5 (Only for Solvay and BASF), 70559-25-0 (Only for Clariont) | 69.2 Kg |
| Propylene carbonate of BASF | Propylene carbonate CAS No. 108-32-7 | 87.3 Kg |
| Benzyl acetate of Huntsman or Benzyl acetate of Tennants fine chemicals LTD | ACETIC ACID PHENYL METHYL ESTER CAS No. 140-11-4 | Up to 1000 L (about 788.5 kg) |

Density, g/ml: 1.00-1.08

TABLE 22

Stability Results of Composition C

| | Start | Room | Oven 54° C. | Oven 40° C. | Cold 10° C. | Cold 4° C. |
|---|---|---|---|---|---|---|
| Appearance | Clear yellowish solution | Clear yellowish solution | Clear yellowish solution, little turbid at the bottom | | no crystal growth | Not crystal growth |
| Concentration Compound of Formula I | 5.00% | 4.869% (reduction 2.62%) | 4.814% (reduction 3.72%) | | | |
| Emulsion stability, 0.2% (Water D, 2 hr.) | | ok | ok | | | |
| Emulsion stability 1.0% (Water D, 2 hr.) | | ok | ok | | | |
| Density (gr/mL) | | 1.0821 | 1.0823 | | | |

TABLE 22-continued

Stability Results of Composition C

|  | Start | Room | Oven 54° C. | Oven 40° C. | Cold 10° C. | Cold 4° C. |
|---|---|---|---|---|---|---|
| pH (1%) |  | 6.65 | 6.64 |  |  |  |
| Foaming 0.2% (Water D, 2 hr.) |  | 60 ml | 60 ml |  |  |  |
| Foaming 1% (Water D, 2 hr.) |  | 10 ml | 10 ml |  |  |  |

Example 15: Tank Mix of Compositions Comprising the Compound of Formula I and Adjuvant(s)

Example 15(a): SC Composition Tank Mixed with Adjuvant

Wheat crop (Winter wheat plants cv. Alixan (Limagrain) at the BBCH 12 growth stage) was treated with compositions comprising the compound of Formula I and adjuvants in different concentrations as built-in composition and/or as tank mix application.

All the tested compositions and mixtures were prepared in a volume of water corresponding to 200 L/ha and used 3 hours after preparation.

The SC composition of Example 1 was mixed with Trycol® (0.2 or 0.4 L per hectare) or Silwet (0.01 L per hectare) which were added as tank mix in 200 L volume of water.

The compositions and mixtures were applied with a hand sprayer at operating pressure of 2 bars. Three replicates (pots) of 6 wheat plants each were used for each condition tested.

After treatment, wheat plants were left to dry at room temperature for 1 hour and then incubated in a climatic chamber: Temperature of 24° C., day/18° C., night—Photoperiod of 16 h light/8 h dark and a Relative Humidity of 65%.

Fragments of the first leaf are cut and transferred in Petri dish containing adapted water agar (6 leaf fragments per Petri dish). Fragments are inoculated with a calibrated pycnospores suspension of Z. tritici strain Mg Tri-R6.

After inoculation, the Petri dishes are incubated in a climatic chamber: Temperature of 20° C., day/17° C., night—Photoperiod of 16 h light/8 h dark and controlled Relative Humidity.

After incubation time of 21 days, the intensity of the infection, which is the surface of colonized leaf by Z. tritici strain, is assessed (quantitative criteria). The fungicidal efficacy on each composition is then determined in percent of the untreated control. All data are treated by statistical software (XL STAT). The expected output of this step is the biological fungicidal efficiency ranking of the compound of Formula I in presence of different adjuvants.

Disease assessments were carried out 21 days post inoculation (dpi) by measuring the length of the necrosis of the leaf fragment. The intensity of infection was then determined in percent of the total length of the leaf fragment.

The efficacy was calculated based on the Area Under the Disease Progress Curve (AUDPC) which is a quantitative measure of disease intensity over time. The most commonly used method for estimating the AUDPC, the trapezoidal method, was performed by multiplying the average disease intensity between each pair of adjacent time points by the time interval corresponding and this for each interval time.

The fungicide efficacies were determined from the AUDPC values and expressed in percent of the untreated control.

Results and Discussion

All adjuvants were tested alone towards Zymoseptoria tritici strain MG Tri-R6. None of the adjuvants tested alone had any significant fungicidal activity against Z. tritici strain Mg Tri-R6 in controlled conditions.

Results are summarized in FIG. 1 to 6.

Results show that adding adjuvant(s) increase the efficacy of compound of Formula I towards Zymoseptoria tritici strain MG Tri-R6.

Figure 2:
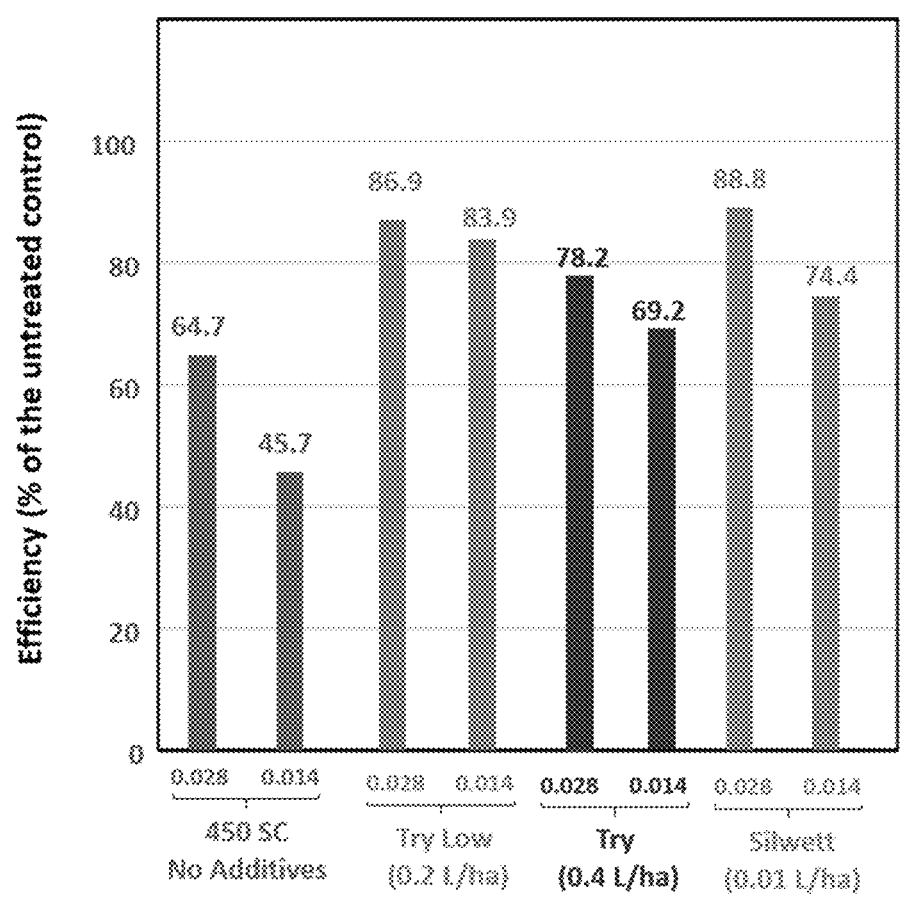
FIG. 2. Effect of Trycol® low (refers to 0.2 L/ha), Trycol® (refers to 0.4 L/ha) or Silwett adjuvant on the activity of compound of Formula I. Comparison of the fungicide efficacy, obtained from AUDPC values, of compound of Formula I 450 suspension concentrate composition used at 2 rates (0.028 and 0.014 L/ha) alone (no adjuvant) or with an adjuvant (Trycol® low, Trycol® or Silwett®) as used at 1 rate towards $Z.$ $tritici$ strain Mg Tri-R6 moderately resistant to DMI and Highly resistant to QoI fungicides in controlled conditions.
Figure 3:
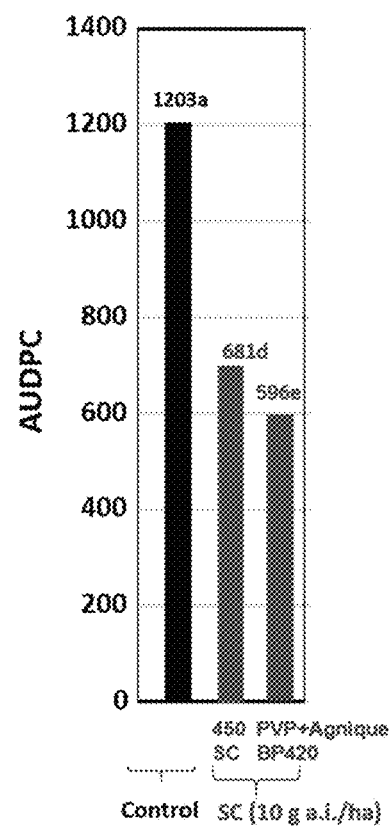
FIG. 3. Effect of combination of two adjuvants. PVP and AGNIQUE BP420 as built-in composition on the activity of compound of Formula I. Comparison of the Area Under Disease Progress Curve (AUDPC) determined from the intensity of infection measured 21 dpi of $Z.$ $tritici$ strain Mg Tri-R6 moderately resistant to DMI fungicides and highly resistant to QoI fungicides of wheat plants cv. Alixan untreated or treated with compound of Formula I 450 suspension concentrate composition used at rate of 10 g a.i./ha alone (no adjuvant) or with the adjuvants. Values of the same timing of observation followed by the same letter are not significantly different according to the Newman and Keuls test ($p<0.05$).

As shown in FIGS. 1 and 2, adding one adjuvant, Trycol® or Silwet® (even in low amount) increased the efficacy and the effective fungicidal activity of compound of Formula I compared to the application without adjuvant.

The results showed that the addition of Trycol® or Silwet® to compound of Formula I SC in a tank mix significantly improved fungicidal efficacy of the composition.

Without wishing to be bound by any theory, it is hypothesized that Silwet® L-077 and Trycol improved fungicidal efficacy of the composition (this adjuvant's concentration is up to 3% by weight based on the total weight of the composition) by lowering the surface tension of the leafs surface.

Figure 4:
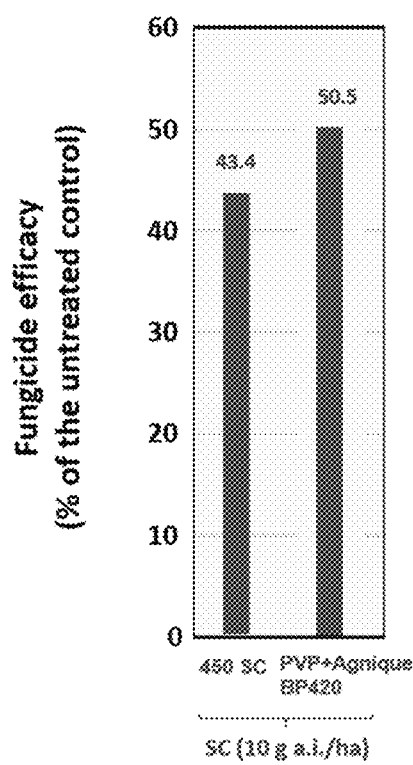
FIG. 4. Effect of combination of two adjuvants, PVP and AGNIQUE® BP420 as built-in composition on the activity of compound of Formula I. Comparison of the fungicide efficacy, obtained from the AUDPC values, of suspension concentrate composition, of compound of Formula I at 10 g a.i/ha towards $Zymoseptoria$ $tritici$ strain Mg Tri-R6 moderately resistant to DMI and highly resistant to QoI fungicides in controlled conditions.
Figure 5:
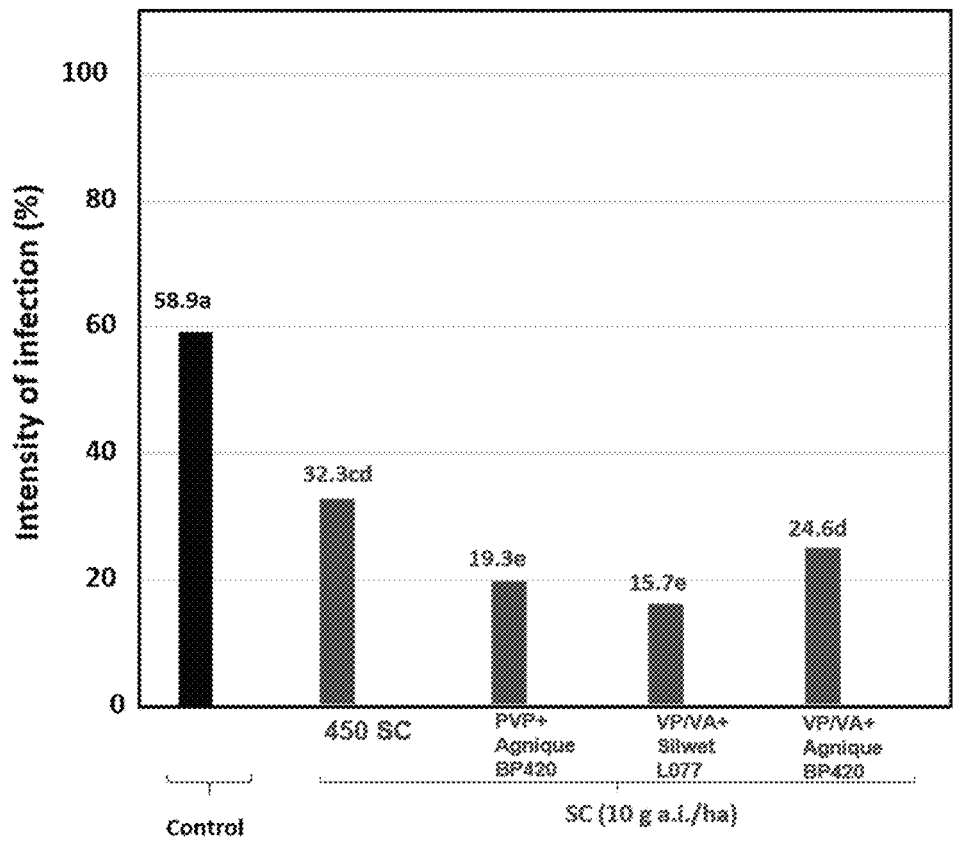
FIG. 5. Effect of three combinations of adjuvants, combination of PVP and AGNIQUE® BP420, combination of VP/VA and Silwett and combination of VP/VA and AGNIQUE®) BP420 as built-in compositions (450 suspension concentrate composition) on the activity of compound of Formula I. Disease assessment (intensity of infection) on the first leaf of wheat plantlets cv. Alixan untreated or treated with suspension concentrate composition of compound of Formula I at 10 g a.i./ha 21 days post inoculation with pycnospores of the $Zymoseptoria$ $tritici$ strain Mg Tri-R6 moderately resistant to DMI and Highly resistant to QoI fungicides in controlled conditions. Values of the same timing of observation followed by the same letter are not significantly different according to the Newman and Keuls test ($P<0.05$).
Figure 6:
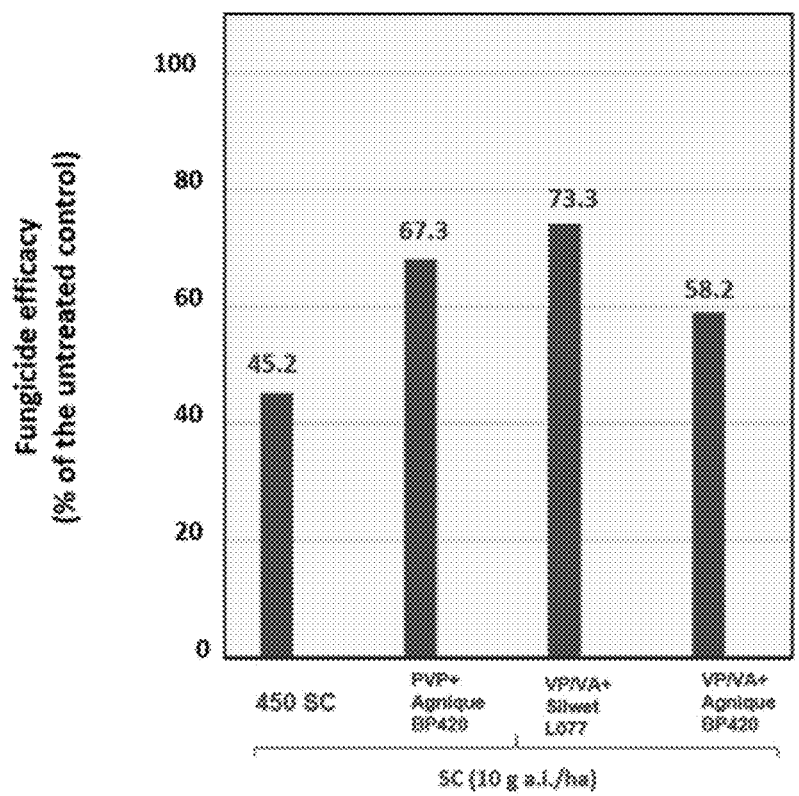
FIG. 6. Effect of three combinations of adjuvants, combination of PVP and AGNIQUE®, BP420, combination of VP/VA and Silwett® and combination of VP/VA and AGNIQUE® BP420 as built-in compositions on the activity of compound of Formula I compound of Formula I (450 suspension concentrate composition). Fungicide efficacy obtained from the intensity of infection determined 21 dpi and suspension concentrate composition of compound of Formula I at 10 g a.i./ha towards *Zymoseptoria tritici* strain Mg Tri-R6 moderately resistant to DMI and Highly resistant to QoI fungicides in controlled conditions.

As shown in FIGS. 4, 5 and 6, adding two adjuvants, Silwet® or Agnique® BP 420 with PVP or VP/VA increased the efficacy and the effective fungicidal activity of compound of Formula I compared to the application without adjuvant.

The efficacy of compound of Formula I in presence of PVP or VP/VA in combination with Agnique® BP 420 (Alcohol ethoxylate propoxylate C16 C18) or Silwet®1) was increased compared to application of the compound of Formula I without adjuvant.

Without wishing to be bound by any theory, it is hypothesized that Silwet® L-077 (Siloxane polyalkyleneoxide copolymer) in combination with VP/VA (this adjuvant's concentration is up to 2% by weight based on the total weight of the composition) increased the efficacy and the effective fungicidal activity of compound of Formula I by lowering the surface tension, thus, spreading the composition on leafs surface. In other words, the deposit of the composition on the leaf surface is more spread out and stays more time on the leaf, thus has rain fastness properties.

Example 15(b): EC Composition Tank Mixed with Adjuvant

The EC formulation and the adjuvants were mixed only prior the experiment (e.g. as tank mix).

All the fungicides are prepared in a volume of water or S-solutions (S-solution refers to the diluted solution of the compositions) corresponding to 200 L/ha and used 3 hours after preparation.

TABLE 23

Compound of Formula I 50 EC formulation

| A.I/ha (gr) | Number of Treatment | Treatment | Formulation (L/ha) | Adjuvant (L/ha) | Water (L/ha) |
|---|---|---|---|---|---|
| 12.5 | 1 | Formulation A – No adjuvant | 0.25 | 0 | 200 |
| 6.25 | 2 | Formulation A – No adjuvant | 0.125 | 0 | 200 |
| 12.5 | 3 | Formulation A + Trycol ® | 0.25 | 0.4 | 200 |
| 6.25 | 4 | Formulation A + Trycol ® | 0.125 | 0.4 | 200 |
| 12.5 | 5 | Formulation B – No adjuvant | 0.25 | 0 | 200 |
| 6.25 | 6 | Formulation B – No adjuvant | 0.125 | 0 | 200 |
| 12.5 | 7 | Formulation B + Trycol ® low | 0.25 | 0.2 | 200 |
| 6.25 | 8 | Formulation B + Trycol ® low | 0.125 | 0.2 | 200 |
| 12.5 | 9 | Formulation B + Trycol ® | 0.25 | 0.4 | 200 |
| 6.25 | 10 | Formulation B + Trycol ® | 0.125 | 0.4 | 200 |
| 12.5 | 11 | Formulation B + SOC | 0.25 | 1 | 200 |
| 6.25 | 12 | Formulation B + SOC | 0.125 | 1 | 200 |

Figure 7:
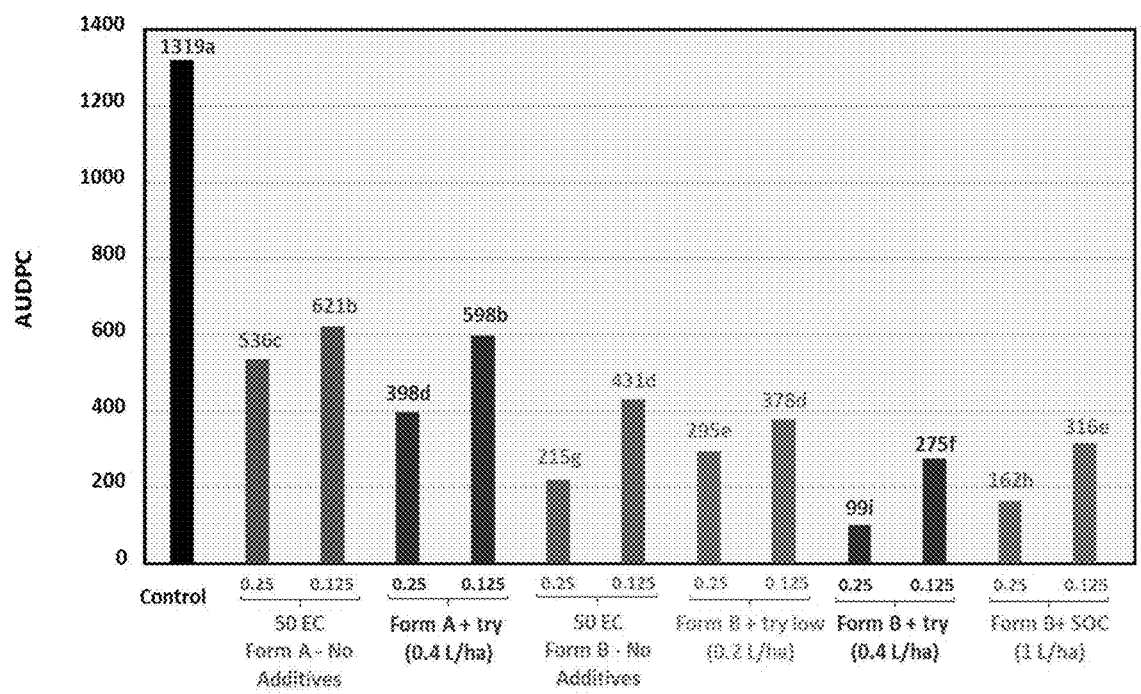
FIG. 7. Comparison of the Area Under Disease Progress Curve (AUDPC) determined from the intensity of infection measured 21 and 28 dpi of *Z, tritici* strain Mg Tri-R6 moderately resistant o DMI fungicides and highly resistant to QoI fungicides of wheat plants cv. Alixan untreated or treated with the compound of Formula I 50 emulsifiable concentrate compositions at 2 rates (0.25 and 0.125 L/ha) composition A alone (no adjuvant/additive) or with an adjuvant (Trycol®) and composition B alone|(no adjuvant/additive) or with an adjuvant (Trycol® low, Trycol®, Synergen® SOC) Values of the same timing of observation followed by the same letter are not significantly different according to the Newman and Keuls test ($p<0.05$).
Figure 8:
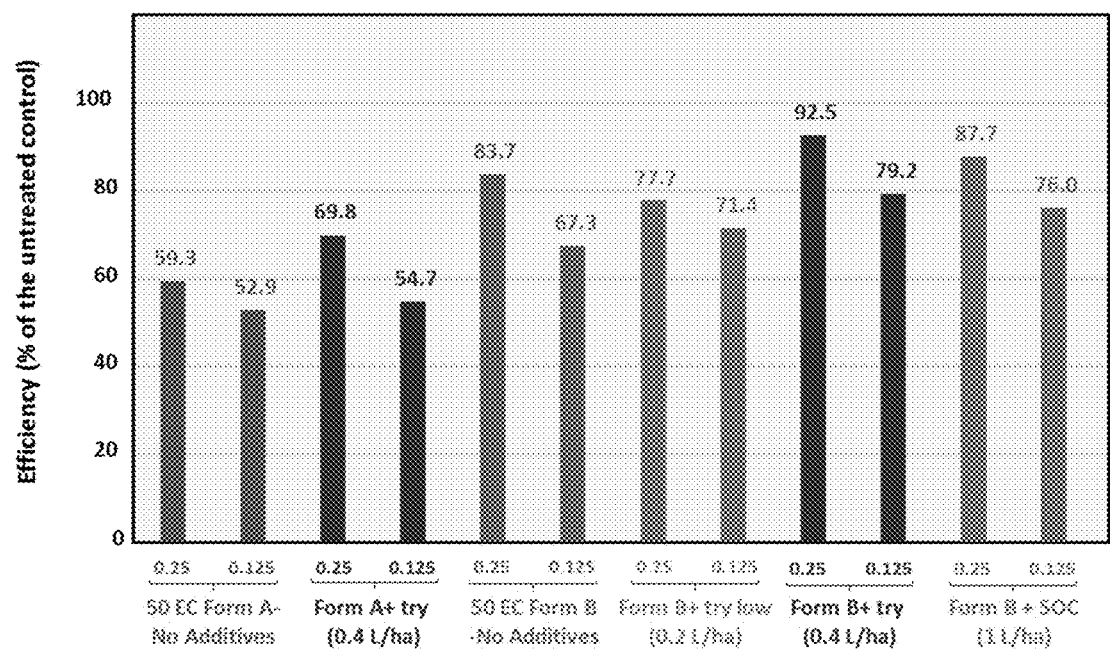
FIG. 8. Comparison of the fungicide efficacy, obtained from AUDPC values, of the compound of Formula I 50 emulsifiable concentrate compositions at 2 rates (0.25 and 0.125 L/ha) composition A alone (no adjuvant) or with an adjuvant (Trycol®) and composition B alone|(no adjuvant/additive) or with an adjuvant (Trycol® low, Trycol®, Synergen® SOC) towards *Z, tritici* strain Mg Tri-R6 moderately resistant to DMI and Highly resistant to QoI fungicides in controlled conditions.

The results are summarized in FIGS. 7 and 8.

Example 16: OD Composition

To assess the fungicidal activity of OD composition containing compound of Formula I, an OD composition (from Example 10, Table 13) was prepared in a volume of water or S-solutions (S-solution refers to the diluted solution of the compositions) corresponding to 200 L/ha and used 3 hours after preparation.

The first leaf of wheat plantlets cv. Alixan were untreated or treated with the OD formulation of Compound of Formula I Prototype A (from Example 10, Table 13) at 10 g a.i./ha and 20 g a.i./ha at 21 days post inoculation with pycnospores of the Zymoseptoria tritici strain Mg Tri-R6 (moderately resistant to DMI and highly resistant to QoI fungicides in controlled conditions). Disease was assessed using intensity of infection.

Figure 9:
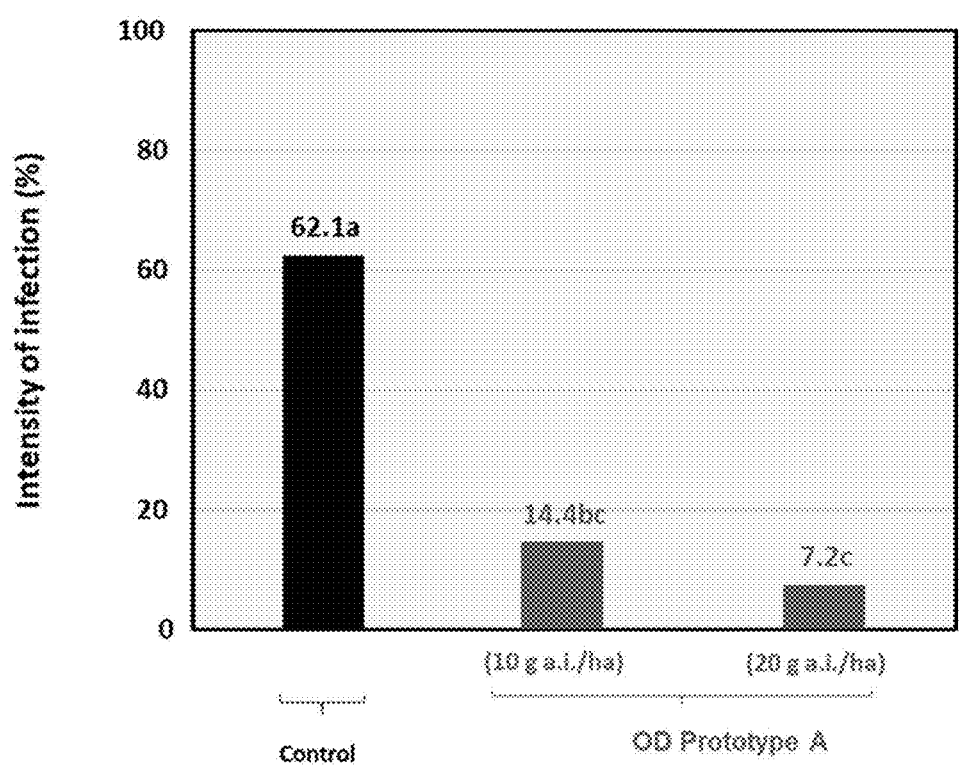
FIG. 9. Disease assessment (intensity of infection) on the first leaf of wheat plantlets cv. Alixan untreated or treated with OD formulation of Compound of Formula I Prototype A at 10 g a.i./ha and 20 g a.i./ha, 21 days post inoculation with pycnospores of the *Zymoseptoria tritici* strain Mg Tri-R6 moderately resistant to DMI and Highly resistant to QoI fungicides in controlled conditions.

The results are shown in FIG. 9.

Example 17: OD Composition and EC Composition with Adjuvant

To assess the fungicidal activity of OD composition and EC composition with adjuvant containing the compound of Formula I on potato late blight (Phytophthora infestans), An OD composition (from Example 10, Table 13) was prepared in a volume of in a volume of water or S-solutions corresponding to 300 L/ha and was applied by knap-sack sprayer: with horizontal boom flat fan nozzles (six weekly applications). The EC composition used is EC Composition C (Example 14, Table 21).

Figure 10:
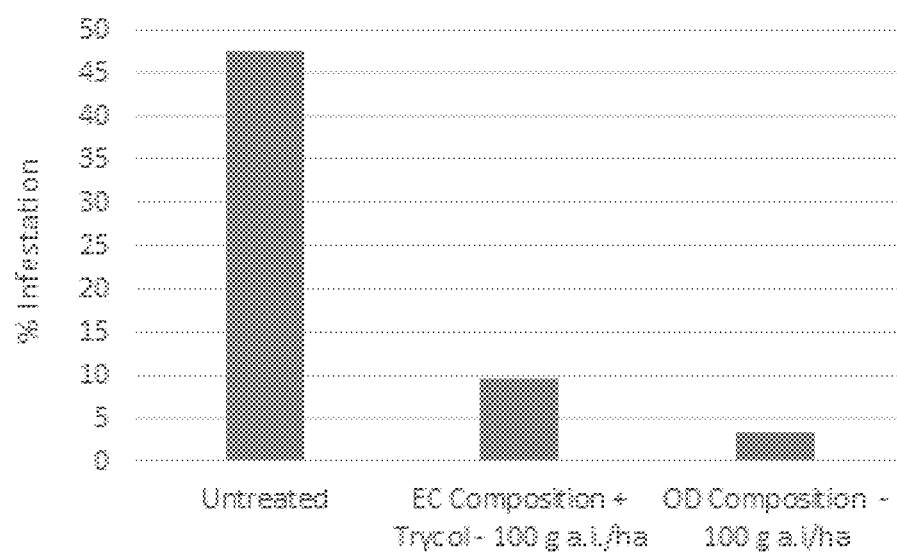
FIG. 10. Disease assessment (% of infection) on potato late blight (*Phytophthora infestans*). Field trial assessment after six weekly applications.

Disease was assessed using percent of infection. The results are shown in FIG. 10.

The invention claimed is:
1. A stable, liquid composition comprising:
(a) a fungicidally effective amount of a compound of Formula I:

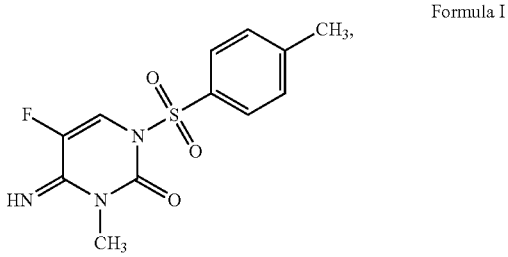 [SMILES: Cc1ccc(S(=O)(=O)n2cc(F)c(=N)n(C)c2=O)cc1]

and
(b) a liquid carrier, wherein:
(i) when the liquid carrier is an aqueous liquid carrier, then the pH of the composition is between 5 to 7.5, the composition comprises a stabilizing surfactant, and the concentration of the compound of Formula I in the stable liquid composition is 150 g/L to 750 g/L; and
(ii) when the liquid carrier is a non-aqueous carrier, then the composition has a water content of less than 0.5% by weight based on the total weight of the composition, and the concentration of the compound of Formula I in the stable liquid composition is 50 g/L to 750 g/L.

2. The stable, liquid composition of claim 1, wherein the composition further comprises at least one adjuvant selected from the group consisting of:
(i) polyalkylene oxide alkyl ether;
(ii) siloxane polyalkyleneoxide copolymer;
(iii) esters of fatty acid;
(iv) vinylpyrrolidones and derivatives thereof; and
(v) sugar-based surfactants.

3. A method for the control and/or prevention of (i) fungal pathogen attack on a plant or (ii) plant and/or soil fungal disease, wherein the method comprises applying the composition of claim 1 to soil, plant, root, foliage, seed, locus of the fungus, and/or a locus in which the infestation is to be prevented so as to thereby control and/or prevent fungal pathogen attack on a plant or plant and/or soil fungal disease.

4. The method of claim 3, wherein:
a) the compound of Formula I is applied at an amount in the range of 5 g/ha to 150 g/ha,
b) the fungal pathogen is one of Leaf Blotch of Wheat (Mycosphaerella graminicola; anamorph: Zymoseptoria tritici), Wheat Brown Rust (Puccinia triticina), Stripe Rust (Puccinia striiformis f. sp. tritici), Scab of Apple (Venturia inaequalis), Blister Smut of Maize (Ustilago maydis), Powdery Mildew of Grapevine (Uncinula necator), Barley scald (Rhynchosporium secalis), Blast of Rice (Magnaporthe grisea), Rust of Soybean (Phakopsora pachyrhizi), Glume Blotch of Wheat (Leptosphaeria nodorum), Powdery Mildew of Wheat (Blumeria graminis f. sp. tritici), Powdery Mildew of Barley (Blumeria graminis f. sp. hordei), Powdery Mildew of Cucurbits (Erysiphe cichoracearum), Anthracnose of Cucurbits (Glomerella lagenarium), Leaf Spot of Beet (Cercospora beticola), Early Blight of Tomato (Alternaria solani), and Net Blotch of Barley (Pyrenophora teres), and/or
c) the plant or soil fungal disease is one of Septoria, Brown rust, Yellow rust, Powdery Mildew, Rhyncospo-

81 rium, *Pyrenophora, Microduchium majus, Sclerotinia,* Downy mildew, *Phythopthora, Cercosporea beticola, Ramularia,* ASR. Sigatoka negra.

5. A method for increasing stability of a liquid composition comprising a compound of Formula I:

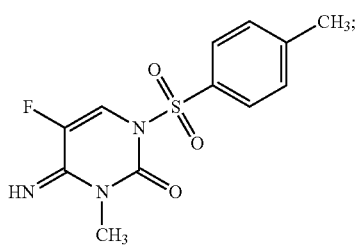

and a liquid carrier, wherein
(i) when the liquid carrier is an aqueous carrier, the method comprises maintaining the pH value of the composition in the range of 5 to 7.5, and adding at least one stabilizing surfactant to the composition; and
(ii) when the liquid carrier is a non-aqueous carrier, the concentration of compound of Formula I in the composition is 50 g/L to 750 g/L, and the method comprises maintaining the water content of the composition to less than 0.5% by weight based on the total weight of the composition,
so as to thereby increase stability of the composition comprising the compound of Formula I.

6. A method for:
(a) (i) the control or prevention of fungal attack on a plant or (ii) protecting a plant from fungal attack comprising applying the composition of claim 1 to a seed adapted to produce the plant,
(b) treating a plant seed or seedling to produce a plant resistant to fungal attack comprising applying the composition of claim 1 to the plant seed or seedling, or
c) protecting a plant from fungal attack comprising applying the composition of claim 1 to the seedling environment.

7. A plant resistant to fungal attack wherein the seed of the plant is treated with the composition of claim 1.

8. A plant seed or seedling adapted to produce a plant resistant to fungal attack, wherein the plant seed or seedling is treated with the composition of claim 1.

9. A package comprising the stable, liquid composition of claim 1.

10. The stable, liquid composition of claim 1, wherein the liquid carrier is an aqueous liquid carrier.

11. The stable, liquid composition of claim 10, wherein:
a) the pH of the composition is in the range of 6 to 7.5,
b) the composition comprises a pH adjuster,
c) the composition comprises from 30% to 70% by weight of the aqueous liquid carrier based on the total weight of the composition,
d) the concentration of the compound of Formula I in the stable, liquid composition is 150 g/L to 750 g/L,
e) the composition is a suspension concentrate (SC) composition wherein the compound of Formula I is suspended in the aqueous carrier, or the composition is a suspoemulsion (SE) composition wherein the compound of Formula I is suspended in the aqueous carrier and the composition comprises a non-aqueous liquid component in the aqueous carrier, and/or

82 f) the stabilizing surfactant is a combination of a non-ionic stabilizing surfactant and an anionic stabilizing surfactant.

12. The stable, liquid composition of claim 10, wherein the stabilizing surfactant structure of polyalkylene oxide polyaryl ether.

13. The stable, liquid composition of claim 10, wherein:
a) the stabilizing surfactant is tristyrylphenol ethoxylate phosphate ester, 2,4,6-Tri-(1-phenylethyl)-phenol polyglycol ether with 54 EO, or ethoxylated tristyrylphenol, or any combination thereof, or
b) the composition comprises two stabilizing surfactants and the stabilizing surfactants are tristyrylphenol ethoxylate phosphate ester and ethoxylated tristyrylphenol.

14. The stable, liquid composition of claim 1, wherein the liquid carrier is a non-aqueous liquid carrier.

15. The stable, liquid composition of claim 14, wherein:
a) the non-aqueous liquid carrier selected from the group consisting of aromatic hydrocarbons, paraffins, petroleum, diesel, mineral oil, ester and/or amide of fatty acids, tall oil fatty acids, polyalkylene oxide alkyl ether, siloxane polyalkyleneoxide copolymer, esters of fatty acid, vinylpyrrolidones and derivatives thereof, sugar-based surfactants, and any combination thereof,
b) the composition comprises from 30% to 80% by weight of the non-aqueous liquid carrier based on the total weight of the composition,
c) the composition has a water content of less than 0.2% by weight based on the total weight of the composition,
d) the composition comprises a stabilizing surfactant,
e) the composition is free of phosphoric acid, urea, propyl gallate, dimethyl sulfoxide (DMSO), morpholine and/or N-methyl pyrrolidone, and/or
f) the composition is an oil dispersion (OD) composition wherein solid particles of the compound of Formula I is suspended in the non-aqueous carrier, or the composition is an emulsifiable concentrate (EC) composition wherein the compound of Formula I is dissolved in the non-aqueous carrier.

16. The stable, liquid composition of claim 1, wherein:
a) the solubility of the compound of Formula I in the liquid carrier is less than 5000 ppm,
b) the composition has a viscosity of 500 cP-3000 cP,
c) the composition comprises an agriculturally acceptable inert additive wherein the agriculturally acceptable inert additive is selected from the group consisting of surfactants, dispersants, emulsifiers, wetting agents, antifoams, solvents, co-solvent, light stabilizers, UV absorbers, radical scavengers and antioxidants, adhesives, neutralizers, thickeners, binders, sequestrates, biocides, buffers preservatives, and anti-freeze agents,
d) the composition further comprises a solid diluent, a liquid diluent, a wetting agent, an adhesive, a thickening agent, an anti-foaming agent, a preservative, an anti-oxidation agent, a binder, a fertilizer, an anti-freeze agent, an additional pesticide, a safener, or any combination thereof, and/or
e) the composition is free of phosphoric acid, urea, propyl gallate, dimethyl sulfoxide (DMSO), morpholine and/or N-methyl pyrrolidone.

17. The stable, liquid composition of claim 2, wherein the composition comprises iso-tridecyl alcohol polyglycol ether, ethoxylate propoxylate alcohol, or C16-C18 alcohol ethoxylate propoxylate ether.

18. The stable, liquid composition of claim 2, wherein the composition comprises a block copolymer of vinylpyrrolidone and vinyl acetate (VP/VA), and wherein:
  a) the amount of VP/VA in the mixture is 0.5-3% by weight based on the total weight of the mixture, or
  b) the composition is a suspension concentrate composition and the concentration of VP/VA in the suspension concentrate composition is 0.5-2.5% by weight based on the total weight of the composition.

19. A process for preparing the stable, liquid composition of claim 1, wherein:
  a) the stable, liquid composition is a suspension concentrate (SC) composition and the process comprises the steps:
    (1) mixing agriculturally acceptable inert additives and an aqueous liquid carrier to obtain a premix;
    (2) adding the compound of Formula I to the premix obtained in step (1) to obtain a mixture; and
    (3) milling the resulting mixture of step (2) to obtain the desired composition;
  b) the stable, liquid composition is a suspoemulsion (SE) composition and the process comprises the steps:
    (1) mixing agriculturally acceptable inert additives and an aqueous liquid carrier to obtain a premix;
    (2) adding the compound of Formula I and at least one adjuvant to the premix obtained in step (1) to obtain a mixture; and
    (3) milling the resulting mixture of step (2) to obtain the desired composition;
  c) the stable, liquid composition is an oil dispersion (OD) composition and the process comprises the steps:
    (1) mixing agriculturally acceptable inert additives and a non-aqueous liquid carrier to obtain a premix;
    (2) adding the compound of Formula I to the premix obtained in step (1) to obtain a mixture; and
    (3) milling the resulting mixture of step (2) to obtain the desired composition; or
  d) the stable, liquid composition is an emulsifiable concentrate (EC) composition and the process comprises the steps:
    (1) mixing the agriculturally acceptable inert additives and a non-aqueous liquid carrier to obtain a premix;
    (2) adding the compound of Formula I to the premix obtained in step (1) to obtain a mixture; and
    (3) filtering the solution of step (2) to obtain the desired composition.

20. The stable, liquid composition of claim 17, wherein the composition comprises C16-C18 alcohol ethoxylate propoxylate ether.

\* \* \* \* \*